United States Patent [19]
Pieken et al.

[11] Patent Number: 6,001,966
[45] Date of Patent: *Dec. 14, 1999

[54] METHOD FOR SOLUTION PHASE SYNTHESIS OF OLIGONUCLEOTIDES AND PEPTIDES

[75] Inventors: Wolfgang Pieken; Larry Gold, both of Boulder, Colo.

[73] Assignee: Proligo LLC, Boulder, Colo.

[ * ] Notice: This patent is subject to a terminal disclaimer.

[21] Appl. No.: 09/130,232

[22] Filed: Aug. 6, 1998

Related U.S. Application Data

[63] Continuation of application No. 08/780,517, Jan. 8, 1997, Pat. No. 5,874,532, which is a continuation-in-part of application No. PCT/US96/16668, Oct. 17, 1996.

[51] Int. Cl.$^6$ .............................. C07K 1/00; C07K 3/00; C12H 15/00
[52] U.S. Cl. .................. 530/338; 530/300; 536/25.3; 536/25.33; 536/25.34; 536/23.1
[58] Field of Search ................................ 536/25.3, 25.33, 536/25.34, 23.1; 530/338, 300

[56] References Cited

U.S. PATENT DOCUMENTS

| | | |
|---|---|---|
| 2,871,225 | 1/1959 | Bortnick et al. . |
| 3,137,684 | 6/1964 | Bodanszky . |
| 5,539,082 | 7/1996 | Nielsen et al. ........................... 530/300 |
| 5,580,697 | 12/1996 | Keana et al. . |
| 5,874,532 | 2/1998 | Pieken et al. ........................... 530/338 |

FOREIGN PATENT DOCUMENTS

WO92/20702 11/1992 WIPO .

OTHER PUBLICATIONS

Barton et al. (1970) J. Chem. Soc. (D) 939.
Beaucage and Iyer (1992) Tetrahedron 48:2223.
Bonora et al. (1993) Nucleic Acids Res. 21:1213.
Bonora (1987) Gazzetta Chimica Italiana 117:379.
Bonora et al. (1990) Nucleic Acids Res. 18:3155.
Bonora et al. (1991) Nucleosides & Nucleotides 10:269.
Bonora (1995) Applied Biochemistry and Biotechnology 54:3.
Bonora and Scremin (1992) *Innovation Prespec. Solid Phase Synth. Collect. Paol, Int. Symp., 2nd*, "Large Scale Synthesis of Oligonucleotides. The *HELP* Method: Results and Perspectives", pp. 355–358, published by Intercept, Andover, UK.
Carpino and El–Faham (1995) J. Am. Chem. Soc. 117:5401.
Carpino et al. (1990) J. Am. Chem. Soc. 112:9651.
colonna et al., (1991) Tetrahedron Lett. 32:3251.
Cookson et al. (1967) J. Chem. Soc.(C) 1905.
Cookson et al. (1971) Org. Syn. 51:121.
Gausepohl et al. (1990) Chemical Abstract, vol. 112, p. 674, col. 2, abstract No. 235812m.
Keanna et al. (1983) J. Org. Chem. 48:2654.
Matteucci and Caruthers (1981) J. Am. Chem. Soc. 103:3185.
Merrigield (1963) J. Am. Chem. Soc. 85:2149.
Mitchell et al. (1978) J. Org. Chem. 43:2845.
Ravikumar et al. (1995) Tetrahedron Lett. 36:6587.
Schaller et al. (1963) J. Am. Chem. Soc. 85:3821.
Scremin and Bonora (1993) Tetrahedron Lett. 34:4663.
Seliger and Schmidt (1987) Journal of Chromatography 397:141.
Sundram and Griffin (1995) J. Org. Chem. 60:1102.
Wright et al. (1993 ) Tetrahedron Lett. 34:3373.
Zaramella and Bonora (1995) Nucleosides & Nucleotides 14:809.
Zon and Geiser (1991) Anti–Cancer Drug Design 6:539.
Xie et al. BBRC 177(1):252–258, 1991.

*Primary Examiner*—Gary L. Kunz
*Attorney, Agent, or Firm*—Swanson & Bratschun LLC

[57] ABSTRACT

This invention discloses an improved method for the sequential solution phase synthesis of oligonucleotides and peptides. The method lends itself to automation and is ideally suited for large scale manufacture oligonucleotides with high efficiency.

14 Claims, 7 Drawing Sheets

METHOD FOR SOLUTION PHASE SYNTHESIS OF OLIGONUCLEOTIDES AND PEPTIDES

RELATED APPLICATIONS

This application is a continuation of U.S. patent application Ser. No. 08/780,517, filed Jan. 8, 1997, entitled "Method for Solution Phase Synthesis of Oligonucleotides and Peptides," which is a continuation-in-part of PCT Application Serial No. PCT/US96/16668, filed on Oct. 17, 1996 designating the United States, entitled "Method for Solution Phase Synthesis of Oligonucleotides."

FIELD OF THE INVENTION

This invention relates to the fields of nucleic acid and peptide chemistry. Specifically, this invention describes a novel method for preparing oligonucleotides and peptides. The method utilized herein for preparing said oligonucleotides and peptides is called PASS, an acronym for Product Anchored Sequential Synthesis.

BACKGROUND OF THE INVENTION

Until quite recently, the consideration of oligonucleotides in any capacity other than strictly informational was unheard of. Despite the fact that certain oligonucleotides were known to have interesting structural possibilities (e.g., t-RNAs) and other oligonucleotides were bound specifically by polypeptides in nature, very little attention had been focused on the non-informational capacities of oligonucleotides. For this reason, among others, little consideration had been given to using oligonucleotides as pharmaceutical compounds.

There are currently at least three areas of exploration that have led to extensive studies regarding the use of oligonucleotides as pharmaceutical compounds. In the most advanced field, antisense oligonucleotides are used to bind to certain coding regions in an organism to prevent the expression of proteins or to block various cell functions. Additionally, the discovery of RNA species with catalytic functions—ribozymes—has led to the study of RNA species that serve to perform intracellular reactions that will achieve desired effects. And lastly, the discovery of the SELEX process (Systematic Evolution of Ligands by Eponential Enrichment) (Tuerk and Gold (1990) Science 249:505) has shown that oligonucleotides can be identified that will bind to almost any biologically interesting target.

SELEX is a method for identifying and producing nucleic acid ligands, termed "nucleic acid antibodies", e.g., nucleic acids that interact with target molecules (Tuerk and Gold (1990) Science 249:505). The method involves selection from a mixture of candidate oligonucleotides and step-wise iterations of binding, partitioning and amplification, using the same general selection theme, to achieve virtually any desired criterion of binding affinity and selectivity.

The use of antisense oligonucleotides as a means for controlling gene expression and the potential for using oligonucleotides as possible pharmaceutical agents has prompted investigations into the introduction of a number of chemical modifications into oligonucleotides to increase their therapeutic activity and stability. Such modifications are designed to increase cell penetration of the oligonucleotides, to stabilize them from nucleases and other enzymes that degrade or interfere with the structure or activity of the oligonucleotide analogs in the body, to enhance their binding to targeted RNA, to provide a mode of disruption (terminating event) once sequence-specifically bound to targeted RNA and to improve their pharmacokinetic properties.

Recent research has shown that RNA secondary and tertiary structures can have important biological functions (Tinoco et al. (1987) Cold Spring Harb. Symp. Quant. Biol. 52:135; Larson et al. (1987) Mol. Cell. Biochem. 74:5; Tuerk et al. (1988) Proc. Natl. Acad. Sci. USA 85:1364; Resnekov et al. (1989) J. Biol. Chem. 264:9953). PCT Patent Application Publication WO 91/14436, entitled "Reagents and Methods for Modulating Gene Expression Through RNA Mimicry," describes oligonucleotides or oligonucleotide analogs which mimic a portion of RNA able to interact with one or more proteins. The oligonucleotides contain modified internucleoside linkages rendering them nuclease-resistant, have enhanced ability to penetrate cells, and are capable of binding target oligonucleotide sequences.

Although there has been a fair amount of activity in the development of modified oligonucleotides for use as pharmaceuticals, little attention has been paid to the preparation and isolation of these compounds on a scale that allows clinical development. The conventional laboratory scale 1 $\mu$mole automated oligonucleotide synthesis does not provide a sufficient amount of the compound of interest to enable clinical development. For clinical development oligonucleotides must be produced in gram-scale to multigram scale amounts at a minimum. Although there are reports of large-scale oligoribonucleotide syntheses in the literature, the term "large-scale" has been applied to the 1 to 10 $\mu$mole scale, rather than gram-scale or kilogram-scale amounts. (Iwai et al. (1990) Tetrahedron 46:6673–6688).

The current state of the art in oligonucleotide synthesis is automated solid phase synthesis of oligonucleotides by the phosphoramidite method, which is illustrated in Scheme 1. (Beaucage and Iyer (1992) Tetrahedron 48:2223–2311; Zon and Geiser (1991) Anti-Cancer Drug Design 6:539–568; Matteucci and Caruthers (1981) J. Am. Chem. Soc. 103:3185–3191). Briefly, the 3'-terminal nucleoside of the oligonucleotide to be synthesized is attached to a solid support and the oligonucleotide is synthesized by addition of one nucleotide at a time while remaining attached to the support. As depicted in Scheme 1 a nucleoside monomer is protected ($P_1$) and the phosphoramidite is prepared (1). The phosphoramidite (referred to as the 5'-protected monomer unit) is then covalently attached to the growing oligonucleotide chain (2), via a phosphite triester linkage, through the 5'-hydroxy group of the ribose ring of the growing oligonucleotide chain to yield the oligonucleotide product (3), in which the majority of the growing oligonucleotide chain has been extended by one nucleotide, but a significant percent of chains are not extended. The product (3) is then oxidized to yield the phosphate triester (4). Prior to the addition of the next base to the growing nucleotide chain, the 5'-hydroxyl group must be deprotected. As can be seen in Scheme 1 (compound 4), however, not all of the reactive sites on the solid support react with the 5'-protected monomer. These unreacted sites (referred to as failure sequences) must, therefore, be protected (referred to as capping) (5) prior to deprotection of the 5'-hydroxyl group (6). Subsequent monomers, which have also been protected and converted to the phosphoramidite, are then sequentially added by coupling the 5'-end of the growing oligomer to the 3'-end of the monomer. Each coupling reaction extends the oligonucleotide by one monomer via a phosphite triester linkage. At each step—and in the case of the initial reaction with the solid support—there are reactive sites that fail to react with the 5'-protected monomer, which results in oligonucleotides that have not been extended by one nucleotide monomer (failure sequences). When the synthesis is complete the desired oligonucleotide (6(n+1 sequence)) is deprotected and cleaved from the resin, together with all of the failure sequences (n, n-x).

The yield of conventional solid phase oligonucleotide synthesis decreases exponentially with the number of monomers coupled. This increases the difficulty of purifying the crude product away from the failure sequences. Additionally, even after high resolution purification has been achieved, it remains very difficult to verify the sequence and composition of the product, especially if it contains non-standard nucleotides.

highly homologous byproducts, which must be carried through to the final crude product (see Scheme 1, structure 6 (n, n-x)). As a result, purification of crude synthetic oligonucleotides to a state acceptable for clinical studies is extremely cumbersome and inefficient. To minimize the percent of failure sequences, a large excess of monomer (approximately 16 fold) is used.

A method to scale-up solid phase oligonucleotide synthesis using a higher loaded polystyrene support was reported by Montserrat et al. (1994) Tetrahedron 50:2617–2622. This method, however, does not overcome the primary problem associated with solid phase synthesis, in that a considerable

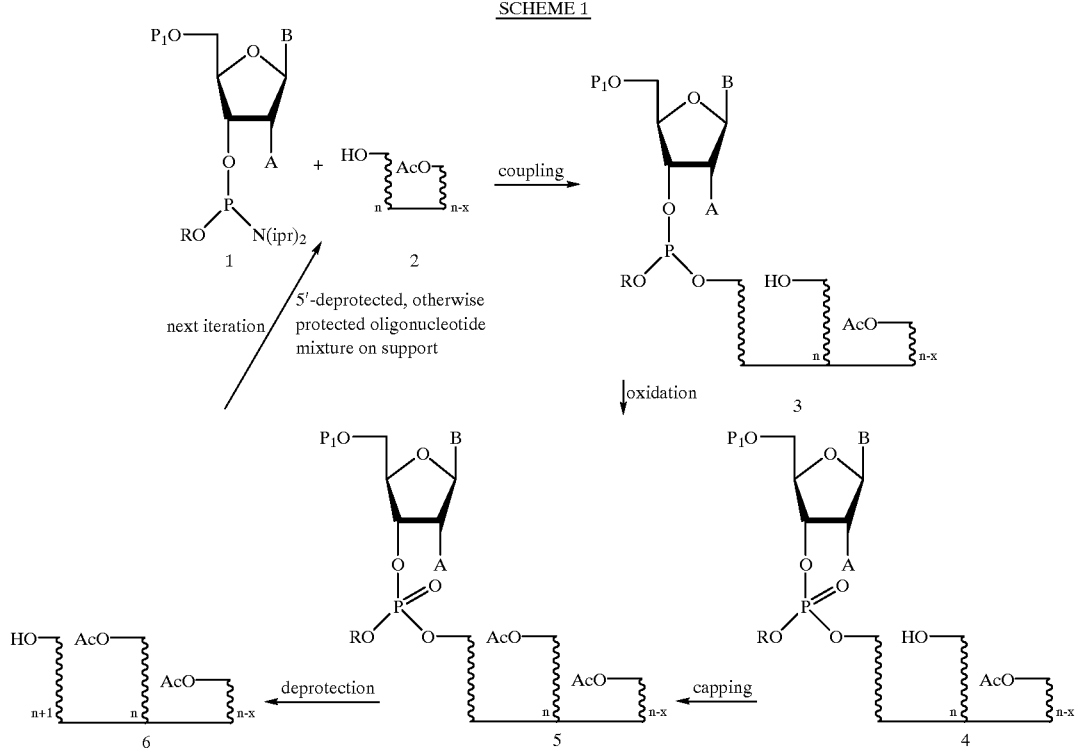

SCHEME 1

Automated oligonucleotide synthesis on solid supports is very efficient for the preparation of small amounts, 0.001 to 0.01 mmol, of a variety of sequences in a minimum amount of time with reasonable yield. It is, however, a highly inefficient process in terms of overall process yield based on input monomer. Typically a 16 fold excess of phosphoramidite is necessary per monomer addition. It has been recognized that the automated solid phase synthesis approach does not readily lend itself to be scaled to a level that allows efficient manufacture of oligonucleotide pharmaceuticals. (Zon and Geiser (1991) Anti-Cancer Drug Design 6:539–568).

The inefficiency of the solid phase synthesis is created to a large extent by the heterophase monomer coupling reaction and by the covalent attachment of both unreacted failure sequences and reaction product to the same support bead. In each cycle, 1–5% of the nucleotide bound to the support does not react with the activated monomer. These unreacted compounds, referred to as failure sequences, as discussed above, must be blocked or capped in order to prevent the subsequent addition of monomers to incomplete oligonucleotides. The generation of failure sequences at every step of the synthesis produces a crude product contaminated with monomer excess is still required to minimize failure sequences. Additionally, the method does not provide consistently satisfactory yields.

In an attempt to decrease the excess of monomer needed to achieve coupling and to achieve easy scaleability, Bonora et al. (1993) Nucleic Acids Res. 21:1213–1217, have investigated using polyethylene glycol (PEG) as a 3'-support that is soluble in the monomer coupling reaction. This method has been used to prepare oligonucleotides by phosphoramidite coupling, H-phosphonate condensation and phosphotriester condensation. (See Bonora (1987) Gazzetta Chimica Italiana 117:379; Bonora et al (1990) Nucleic Acids Res. 18:3155; Bonora et al. (1991) Nucleosides & Nucleotides 10:269; Colonna et al. (1991) Tetrahedron Lett. 32:3251–3254; Bonora and Scremin (1992) Innovation Perspect. Solid Phase Synth. Collect. Pap., Int. Symp., 2nd, "Large Scale Synthesis of Oligonucleotides. The HELP Method: Results and Perspectives", pp. 355–358, published by Intercept, Andover, UK; Scremin and Bonora (1993) Tetrahedron Lett. 34:4663; Bonora (1995) Applied Biochemistry and Biotechnology 54:3; Zaramella and Bonora (1995) Nucleosides & Nucleotides 14:809). The weakness of this approach is the unacceptably low recovery of support bound oligonucleotide after each reaction step. Additionally, this method does not address the problem of failure sequences that must be capped and carried through to the final product.

A polyethylene glycol-polystyrene copolymer support has also been used for the scale-up of oligonucleotide synthesis. (Wright et al. (1993) Tetrahedron Lett. 34:3373–3376). At the 1 mmol scale a 96.6% coupling efficiency per monomer addition was reported for an 18mer DNA. Again, this method does not address the problem of failure sequences bound to the resin.

Zon et al. have suggested a block approach to the synthesis of oligonucleotides, in which a library of dimer or multimer oligonucleotide fragments are prepared in solution and then coupled to each other. (Zon and Geiser (1991) Anti-Cancer Drug Design 6:539–568). The fragments are activated for coupling by differential 5'-deprotection and 3'-phosphorylation. Phosphotriester coupling has been suggested for fragment preparation. (Bonora et al. (1993) Nucleic Acids Res. 21:1213–1217). Due to the comparatively low yield of phosphotriester coupling this approach has not been widely accepted.

In conventional oligonucleotide synthesis, the 5'-protecting group serves to prevent reaction of the 5'-hydroxyl group of one monomer with the phosphoramidite group of a second monomer during the coupling step. The 4,4'-dimethoxytrityl (DMT) group is commonly used as the 5'-protecting group (Schaller et al. (1963) J. Am. Chem. Soc. 85:3821) of the 5'-protected monomer unit added during oligonucleotide synthesis. This group is chosen because of the ease and selectivity with which it can be removed from the 5'-oxygen of the oligonucleotide product prior to addition of the next 5'-protected monomer unit (for a review see: Beaucage and Iyer (1992) Tetrahedron 48:2223–2311). In solution, deprotection of the 5'-DMT group is impaired by the reversibility of acid induced detritylation. In order to drive this reaction to completion, a scavenger of the free trityl cation is added for solution-phase detritylation (Ravikumar et al. (1995) Tetrahedron Lett. 36:6587). It has been recognized that the final 5'-terminal DMT group may serve as a hydrophobic handle which allows separation of the full-length product oligonucleotide from shorter failure sequences by reverse phase chromatography. Additionally, highly hydrophobic analogs of the DMT group have been prepared to enhance the resolution of the separation of full length deprotected oligonucleotide product from failure sequences after complete solid phase synthesis (Seliger and Schmidt (1987) Journal of Chromatography 397:141). In another approach, a fluorescent trityl analog has been used for the 5'-terminal protecting group during oligonucleotide synthesis to allow facile detection of full-length product in crude deprotected oligonucleotide (Fourrey et al. (1987) Tetrahedron Lett. 28:5157). Colored trityl groups were devised to allow monitoring of specific monomer additions during solid phase oligonucleotide synthesis (Fisher and Caruthers (1983) Nucleic Acids Res. 11:1589). Other modified trityl groups have been prepared for the purpose of changing or enhancing the selectivity with which the trityl group can be removed from the oligonucleotide during solid phase oligonucleotide synthesis (for a review, see: Beaucage and Iyer (1992) Tetrahedron 48:2223–2311).

To date, trityl groups which allow anchoring of the product to a resin or membrane during oligonucleotide synthesis in solution have not been designed. Additionally, trityl groups which can covalently react with a derivatized resin, membrane or soluble polymer have not been reported.

Proteins and peptides play a critical role in virtually all biological processes, functioning as enzymes, hormones, antibodies, growth factors, ion carriers, antibiotics, toxins, and neuropeptides. Biologically active proteins and peptides, therefore, have been a major target for chemical synthesis. Chemical synthesis is used to verify structure and to study the relationship between structure and function, with the goal of designing novel compounds for potential therapeutic use. Synthetic peptides comprise a prominent class of pharmaceuticals.

There are currently two basic methods for synthesizing proteins and peptides: solution phase synthesis in which the chemistry is carried out in solution and solid phase synthesis in which the chemistry is carried out on a solid support. A major disadvantage of solution phase synthesis of peptides is the poor solubility of the protected peptide intermediates in organic solvents. Additionally, purifications are difficult and time consuming. Solid phase synthesis overcomes these problems and has become the method of choice in synthesizing peptides and proteins. (See, Merrifield (1963) J. Am. Chem. Soc. 8:2149; Mitchell et al. (1978) J. Org. Chem. 43:2845–2852; Bodansky (1984) in *Principles of Peptide Synthesis,* (Springer Verlag Berlin); Stewart and Young (1984) in *Solid Phase Peptide Synthesis,* sec. ed., Pierce Chemical Company, Illinois pp. 88–95).

Generally, solid phase peptide synthesis proceeds from the C-terminal to the N-terminal amino acid. Briefly, the carboxy-terminal amino acid of the peptide to be synthesized is protected and covalently attached to a solid support, typically a resin. The subsequent amino acids (which have been N-protected and side-chain protected) are then sequentially added either as the free carboxylic acid or in the form of an activated ester derivative. The two most frequently used protecting groups for the N-terminal amino group are Fmoc (Fmoc-9-fluorenylmethyl carbonyl; Carpino and Han (1972) J. Org. Chem. 37:3404) and Boc (Boc-tert-butoxycarbonyl; Sheppard (1986) Science 33:9; Pulley and Hegedus (1993) J. Am. Chem. Soc. 115:9037–9047). When the synthesis is complete the peptide is deprotected, cleaved from the resin and purified.

Increasing the efficiency of solution phase preparation of peptides continues to be an active field of investigation. Introduction of the N-Fmoc protected amino acid fluorides and subsequent in situ generation of these monomers allows efficient solution phase preparation of peptides with minimal racemization. (Carpino et al. (1990) J. Am. Chem. Soc. 112:9651–9652; Carpino and El-Faham (1995) J. Am. Chem. Soc. 117:5401–5402). This method has been applied to the preparation of the antibiotic vancomycin carboxamide derivatives. (Sundram and Griffin (1995) J. Org. Chem. 60:1102–1103).

Although there have been continuous improvements in the methods for peptide synthesis, typical yields for synthetic peptides remain rather moderate. This necessitates lengthy downstream processing procedures to obtain pure product.

The Diels-Alder reaction is a cycloaddition reaction between a conjugated diene and an unsaturated molecule to form a cyclic compound with the $\pi$-electrons being used to form the new $\sigma$ bonds. The Diels-Alder reaction is an example of a [4+2] cycloaddition reaction, as it involves a system of $4\pi$ electrons (the diene) and a system of $2$-$\pi$ electrons (the dienophile). The reaction can be made to occur very rapidly, under mild conditions, and for a wide variety of reactants. The Diels-Alder reaction is broad in scope and is well known to those knowledgeable in the art. A review of the Diels-Alder reaction can be found in "Advanced Organic Chemistry" (March, J., ed.) 761–798 (1977) McGraw Hill, NY, which is incorporated herein by reference.

To date, although a number of attempts have been made, there still remains a need for a method to produce oligonucleotides in large quantities, in continuous operations, at low cost and without laborious purification.

BRIEF SUMMARY OF THE INVENTION

The present invention includes methods for the sequential solution phase synthesis of oligonucleotides that increase reaction yields and allow for scale-up possibilities. As opposed to traditional schemes in which the 3'-end of the growing oligonucleotide is bound to a solid support, the present invention is characterized by use of an anchor group attached to the 5'-end of the growing oligonucleotide that allows successfully coupled product to be separated from unreacted starting materials. In one embodiment, the anchor group also serves as the 5'—OH protecting group and the coupling reaction occurs in solution. The successfully reacted oligomer will contain the protecting group, while the unreacted oligomer will not, and the materials can be partitioned based on the presence of the anchor/protecting group. In a preferred embodiment, the anchor group reacts covalently with a derivatized solid support, such as a resin, membrane or polymer.

In a preferred embodiment of the invention, the monomer unit consists of a 5'-protected phosphoramidite or H-phosphonate, wherein the protecting group is a substituted trityl group, levulinic acid group, or silyl ether group. In one embodiment, the unreacted oligonucleotide starting material (failure sequence) may be separated from the reacted oligonucleotide product based on the affinity of the protecting group for a chromatography resin. In a preferred embodiment, the unreacted oligonucleotide starting material may be separated from the reacted oligonucleotide product based on the specific reaction of the protecting group with a derivatized solid support, such as a resin, membrane or polymer. In a preferred aspect of the invention the partitioning method to remove unreacted oligonucleotide serves to allow for isolation and reuse of the unreacted oligonucleotide and also will allow the reacted oligonucleotide to be deprotected in preparation for the subsequent addition of the next 5'-protected monomer unit.

The method of this invention is not limited to phosphoramidite coupling chemistry, but is compatible with other coupling reactions such as H-phosphonate or phosphate triester coupling chemistry. This method also lends itself to automation and is ideally suited for the large scale manufacture of oligonucleotides with high efficiency.

The present invention includes a method and apparatus to automatically separate the product from the unreacted 5'-protected monomer unit and the starting material. In one embodiment the apparatus is comprised of an extraction vessel and a chromatography resin filtration chamber, which contains a solid support. Upon completion of a monomer addition reaction, the reaction mixture is pumped into the extraction chamber, extracted and then eluted through the solid support, which retains only the 5'-protected monomer unit. The product is then separated from the starting material by eluting through a solid support that retains only the product. In a second embodiment the chromatography resin filtration chamber contains a solid support which covalently reacts with both the 5'-protected monomer unit and the product. The starting material is eluted from the solid support and the monomer and product are then released from the solid support with a dilute acid. The product is then separated from the 5'-protected monomer unit by passage through an ultrafiltration membrane.

A material cost analysis reveals that the 5'-protected phosphoramidite is the most costly reaction component in oligonucleotide synthesis. The cost of the remaining materials are trivial in comparison. Therefore, it would be desirable to make the monomer the limiting reagent. Furthermore, a particular intermediate oligonucleotide sequence which failed to add to the incoming monomer could serve as an intermediate in a subsequent synthesis. Using the method of this invention, verification of the sequence and composition of oligonucleotide product becomes trivial. After every monomer addition cycle, a fully protected, neutral intermediate is obtained, which is easily analyzed by mass spectrometry without tedious sample preparation. Over the course of an oligonucleotide synthesis a library of analytical data for every sequential monomer addition can be obtained. Thus, product analysis becomes an integral part of the process.

The present invention also includes methods for the sequential solution phase synthesis of peptides. This embodiment of the invention is characterized by use of an anchor group attached to the N-terminal protecting group of the growing peptide that allows successfully coupled product to be separated from unreacted starting materials. The successfully reacted peptide will contain the anchor group, while the unreacted peptide will not, and the materials can be partitioned based on the presence of the anchor/protecting group. In a preferred embodiment, the anchor group reacts covalently with a derivatized solid support, such as a resin, membrane or polymer. The invention provides a method for the solution phase synthesis of a wide variety of peptides and modified peptides.

The methods of the present invention can be extended to all sequential polymerization reactions and thus to the sequential synthesis of any polymer, including but not limited to peptide nucleic acids (PNAs) and carbohydrates.

DETAILED DESCRIPTION OF THE INVENTION

Figure 1:
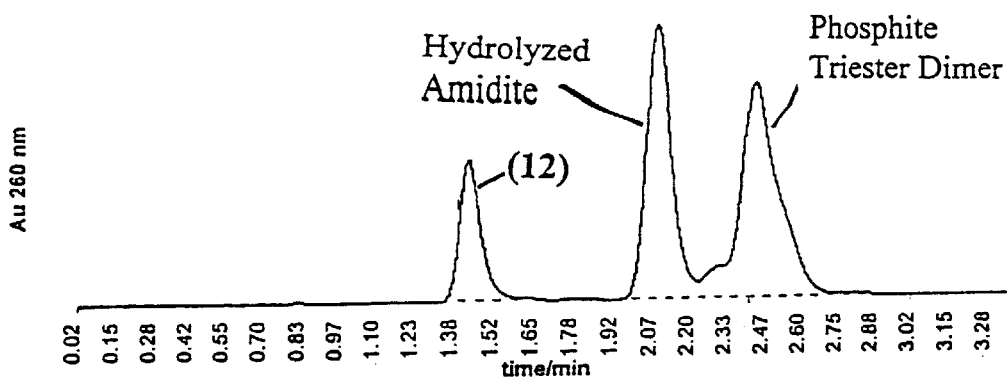
FIG. 1 illustrates the reverse phase High Pressure Liquid Chromatography (HPLC) trace of the phosphoramidite coupling reaction mixture set forth in Example 1 prior to oxidation.

The present invention includes methods for the solution phase synthesis of oligonucleotides, referred to herein as Product Anchored Sequential Synthesis (PASS). Unlike traditional schemes where the 3'-end of the growing oligonucleotide is bound to a solid support, the present invention is characterized by utilization of an anchor group attached to the 5'-end of the growing oligonucleotide product that allows successfully coupled product to be separated from unreacted starting materials. In a preferred embodiment the anchor group also serves as the 5'-OH protecting group. The successfully reacted oligonucleotide product will contain the protecting group, while the unreacted oligonucleotide starting material will not, and the product can be partitioned away from the starting material based on the presence of the blocking/protecting group. Unreacted starting material is recovered and can be reused in a subsequent synthesis batch of the same oligonucleotide. Thus, in contrast to conventional solid phase synthesis, the improved method for oligonucleotide synthesis described herein does not employ a solid support for anchoring of the 3'-end of the growing oligonucleotide chain.

Specifically, the invention provides a method for the solution phase synthesis of a wide variety of oligonucleotides and modified oligonucleotides comprising reaction of a 5'-protected monomer unit with the 5'-end of a growing oligonucleotide chain in solution. Performing these reactions in solution, rather than on solid supports, provides for better reaction kinetics. In an additional aspect of the invention, following reaction between the 5'-protected monomer unit and the growing oligonucleotide, the unreacted 5'-protected monomer unit may be activated and oxidized to form a charged species that may be easily partitioned from the remainder of the reaction medium. In the preferred embodiments of the invention the monomer units are phosphoramidites, that upon oxidation can be easily converted to phosphate diesters. The charged phosphate species can be easily partitioned from the remainder of the reaction medium. Additionally, in a preferred embodiment the oxidation may be performed in situ.

When using a H-phosphonate as the 5'-protected monomer unit, which is a charged species (Example 2, Scheme 5), the oxidization of H-phosphonate is deferred until after the addition of the final monomer. The charged H-phosphonate monomers, produce neutral H-phosphonate diester products after coupling, and the charged monomer species are readily removed by anion exchange filtration or extraction. In addition, the recovered H-phosphonate monomers are reusable.

The 5'-protecting group that is utilized can be selected from any class of chemical functionalities that meets the basic requirements of the invention. The protecting group must be of a type that can be used to differentiate the product of the reaction from the remainder of the reaction mixture in order to effect a separation. Preferably, the protecting group will have a strong affinity for or a reactivity with a particular phase or solid support and it must be easily cleaved or removed from the phase or solid support with high selectivity. The oligonucleotide product may be separated from unreacted oligonucleotide starting material using standard methods known to those skilled in the art including, but not limited to, centrifugation, separation on a resin, silica gel based separation, separation based on affinity for a metal, separation based on a magnetic force or electromagnetic force or separation based upon covalent attachment to a suitable solid support.

In a preferred aspect of the invention the partitioning method to remove unreacted oligonucleotide starting material serves to both allow for the isolation for reuse of the unreacted oligonucleotide and also will result in a resin-bound oligonucleotide product which is easily deprotected in preparation for the subsequent addition of the next 5'-protected monomer unit. Most preferably, the protecting group will covalently react with a derivatized solid support, such as a resin, membrane or polymer, to give a covalently anchored protecting group which may easily be cleaved from the oligonucleotide with high selectivity.

In the most preferred embodiment of the invention, the monomer unit consists of a 5'-protected phosphoramidite or H-phosphonate, wherein the protecting group is a substituted trityl group, levulinic acid group or silyl ether group. The preferred substitution on the protecting group is a diene functionality, which can react, via a Diels-Alder reaction, with a solid support, such as a resin, membrane or polymer that has been derivatized with a dienophile. In this embodiment, the unreacted oligonucleotide starting material is separated from the reacted nucleotide product based on the selective or specific covalent reaction of the 5'-protecting group with a derivatized resin.

The present invention also includes methods for the solution phase synthesis of peptides by PASS. This method is characterized by utilization of an anchor group attached to the N-terminal amino acid end of the growing peptide product that allows successfully coupled product to be separated from unreacted starting materials. In a preferred embodiment the anchor group also serves as the N-protecting group. The successfully reacted peptide product will contain the anchor group, while the unreacted peptide starting material will not, and the product can be partitioned away from the starting material based on the presence of the anchor group. Unreacted starting material is recovered and can be reused in a subsequent synthesis batch of the same peptide. Thus, in contrast to conventional solid phase synthesis, the improved method for peptide synthesis described herein does not employ a solid support for anchoring of the carboxy-terminal end of the growing peptide chain.

Specifically, the invention provides a method for the solution phase synthesis of a wide variety of peptides and modified peptides comprising reaction of an N-protected amino acid monomer unit with the N-terminal end of a growing peptide chain in solution. The method for peptide synthesis described herein is designed to introduce highly efficient and scalable preparation of peptides with unprecedented purity. This is achieved by exploiting the N-terminal monomer protecting group to function as a handle which allows selective and efficient isolation of the peptide product at each amino acid addition step (Product Anchored Sequential Synthesis, PASS).

The N-terminal protecting group that is utilized can be selected from any class of chemical functionalities that meets the basic requirements of the invention. The protecting group must be of a type that can be used to differentiate the product of the reaction from the remainder of the reaction mixture in order to effect a separation. Preferably, the protecting group will have a strong affinity for or a reactivity with a particular phase or solid support and it must be easily cleaved or removed from the phase or solid support with high selectivity. The protecting group must also be compatible with conventional peptide synthesis steps. The peptide product may be separated from unreacted peptide starting material using standard methods known to those skilled in the art including, but not limited to, centrifugation, separation on a resin, silica gel based separation, separation based on affinity for a metal, separation based on a magnetic force or electromagnetic force or separation based upon covalent attachment to a suitable solid support.

In a preferred aspect of the invention the partitioning method to remove unreacted peptide starting material serves to both allow for the isolation for reuse of the unreacted peptide and also will result in a resin-bound peptide product which is easily deprotected in preparation for the subsequent addition of the next N-terminal protected amino acid monomer unit. Most preferably, the protecting group will covalently react with a derivatized solid support, such as a resin, membrane or polymer, to give a covalently anchored protecting group which may easily be cleaved from the peptide with high selectivity.

Certain terms used to describe the invention herein are defined as follows:

"Nucleoside" means either a deoxyribonucleoside or a ribonucleoside or any chemical modifications thereof. Modifications of the nucleosides include, but are not limited to, 2'-position sugar modifications, 5-position pyrimidine modifications, 8-position purine modifications, modifications at cytosine exocyclic amines, substitution of 5-bromouracil, and the like.

"Oligonucleotide" refers to either DNA or RNA or any chemical modifications thereof. The oligonucleotides synthesized by the method of this invention are depicted generally as follows:

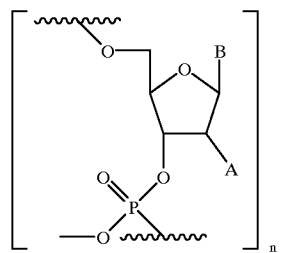

where n=1–1,000, A is a 2'-sugar substituent as defined below and B is a nucleobase as defined below.

A "solid support" as used herein refers to a resin, membrane, phase, polymer, polymer precursor, or soluble polymer that can undergo phase transition. A solid support also refers to a resin, membrane, phase, polymer, polymer precursor, or soluble polymer that has been derivatized with a D group or a Y group, as defined below. The term resin and solid support are used interchangeably and one of ordinary skill in the art will recognize what is intended by the term resin. Examples of solid supports include, but are not limited to, maleimide derivatized polystyrene, polystyrene derivatized with D or Y groups, as defined below, dienophile or diene derivatized polystyrene, Tentagel™ derivatized with a D or Y groups, as defined below, dienophile or diene derivatized Tentagel™, dienophile or diene derivatized ultrafiltration membranes, dienophile or diene derivatized polyethylene glycol, diene or dienophile derivatized inorganic oxides, such as silica gel, alumina, controlled pore glass and zeolites, other dienophile or diene derivatized polymers, hydrophobic reverse phase resins, such as C2 to C18 polystyrene, thiopropyl Sepharose (Pharmacia Biotech), mercurated resin, agarose adipic acid hydrazide (Pharmacia Biotech), or avidin resin.

A "dienophile" is defined as a molecule bearing an alkene group, or a double bond between a carbon and a heteroatom, or a double bond between two heteroatoms, which can undergo a [2+4] cycloaddition reaction with a suitable diene.

A "diene" is defined as a molecule bearing two adjacent double bonds, where the atoms forming these double bonds can be carbon or a heteroatom, which can undergo a [2+4] cycloaddition reaction with a dienophile.

The dienophile can be any group, including but not limited to, a substituted or unsubstituted alkene, or a substituted or unsubstituted alkyne. Typically, the dienophile is a substituted alkene of the formula C=C—Z or Z'—C=C—Z, wherein Z and Z' are electron withdrawing groups independently selected from CHO, COR, COOH, COCl, COAr, CN, $NO_2$, Ar, $CH_2OH$, $CH_2Cl$, $CH_2NH_2$, $CH_2CN$, $CH_2COOH$, halogen, or C=C.

A "dienophile derivatized solid support" refers to a solid support that has been functionalized with a dienophile and a "diene derivatized solid support" refers to a solid support that has been functionalized with a diene. Preferred solid supports are inorganic oxides selected from the group consisting of silica, alumina, zeolites, controlled pore glass, that have hydroxyl groups that are capable of being functionalized, or organic supports such as polystyrene, as illustrated in Schemes 13 and 14. In a preferred embodiment the dienophile is maleimide and the diene is 3,5-hexadiene.

The "5'-protected monomer units" of this invention are generally depicted as follows including the conventional numbering for the ribose ring:

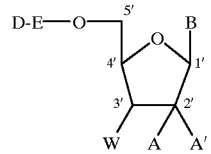

B is a nucleobase;
A and A' are 2'-sugar substituents;
W is independently selected from the group consisting of a phosphoramidite, H-phosphonate, phosphotriester, phosphoramidate, protected oligonucleotide and methylphosphonate; and
D-E is an alcohol protecting group(s) which serves as an anchor for partitioning the successfully reacted oligonucleotide product away from the unreacted oligonucleotide starting material.

Other obvious substitutions for the substituents described above are also included within the scope of this invention, which is not limited to the specific, but rather the generalized formula of reaction.

In a preferred embodiment of the invention:
W is a phosphoramidite or H-phosphonate;
A and A' are independently selected from the group consisting of H, $^2H$, $^3H$, Cl, F,
OH, $NHOR^1$, $NHOR^3$, $NHNHR^3$, $NHR^3$, =NH, CHCN, $CHCl_2$, SH, $SR^3$, $CFH_2$, $CF_2H$, $CR^2_2Br$, —$(OCH_2CH_2)_n$ $OCH_3$, $OR^4$ and imidazole (see U.S. patent application Ser. No. 08/264,029, filed Jun. 22, 1994, entitled "Novel Method of Preparation of 2'Modified Pyrimidines Intramolecular Nucleophilic Displacement," which is incorporated herein by reference);

$R^1$ is selected from the group consisting of H and an alcohol protecting group;

$R^2$ is selected from the group consisting of =O, =S, H, OH, $CCl_3$, $CF_3$, halide, optionally substituted $C_1$–$C_{20}$ alkyl (including cyclic, straight chain, and branched), alkenyl, aryl, $C_1$–$C_{20}$ acyl, benzoyl, $OR^4$ and esters;

$R^3$ is selected from the group consisting of $R^2$, $R^4$, CN, $C(O)NH_2$, $C(S)NH_2$, $C(O)CF_3$, $SO_2R^4$, amino acid, peptide and mixtures thereof;

$R^4$ is selected from the group consisting of an optionally substituted hydrocarbon ($C_1$–$C_{20}$ alkyl, $C_2$–$C_{20}$ alkenyl, $C_2$–$C_{20}$ alkynyl), an optionally substituted heterocycle, t-butyldimethylsilyl ether, triisopropylsilyl ether, nucleoside, carbohydrate, fluorescent label and phosphate; most preferably A is selected from the group consisting of H, OH, $NH_2$, Cl, F, $NHOR^3$, $OR^4$, $OSiR^4{}_3$. (See U.S. patent application Ser. No. 08/264,029, filed Jun. 22, 1994, entitled "Novel Method of Preparation of 2'Modified Pyrimidines Intramolecular Nucleophilic Displacement," filed Jun. 22, 1994);

D-E can be any group that enables the partitioning of the "growing oligonucleotide chain" or "oligonucleotide product" away from unwanted side products and starting materials. The partitioning can be done by any suitable method, including but not limited to, silica gel based chromatography, centrifugation, or any other means known by those in the art for partitioning materials. The preferred method for partitioning is by binding to a resin. The most preferred method for partitioning is by covalent reaction between D and a derivatized solid support, such as a derivatized resin, polymer, or membrane. The protecting group D-E, therefore, is preferably designed such that D has a strong affinity for a particular resin or phase, and E is designed such that the 5'-oxygen-E bond is easily cleaved with high selectivity. In cases where E shows high affinity for a resin or phase, D may be omitted. Most preferably the protecting group D-E is designed such that D can selectively or specifically form a covalent bond to a particular derivatized resin, polymer, or membrane.

E includes, but is not limited to, the trityl group or the levulinic acid group or a silyl ether group, as depicted below.

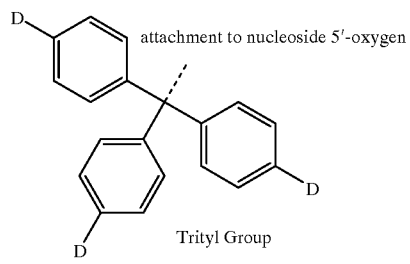

Trityl Group

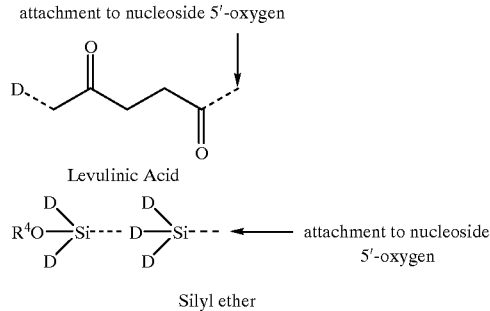

Levulinic Acid

Silyl ether

D includes, but is not limited to, groups independently selected from H, $OR^4$, an alkyl or substituted alkyl group bearing a conjugated diene unit, an alkoxy or substituted alkoxy group bearing a conjugated diene unit, $CH_2$=CHCH=$CHCH_2CH_2O$—, maleimide substituted alkoxy groups, dienophile substituted alkoxy groups, alkoxy groups, an alkylamino or substituted alkylamino group bearing a conjugated diene unit, maleimide substituted alkylamino groups or substituted alkylamino groups, an alkylamino group or substituted alkylamino group bearing a dienophile moiety, disulfides, aldehydes, and metal chelators, some examples of which are depicted below. The alkyl groups on the above listed substituents can have between 1–50 carbons, preferably 1–30 carbons.

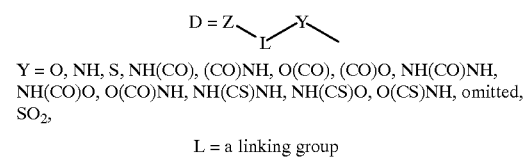

Y = O, NH, S, NH(CO), (CO)NH, O(CO), (CO)O, NH(CO)NH, NH(CO)O, O(CO)NH, NH(CS)NH, NH(CS)O, O(CS)NH, omitted, $SO_2$, L = a linking group X = electron withdrawing group or electron donating group

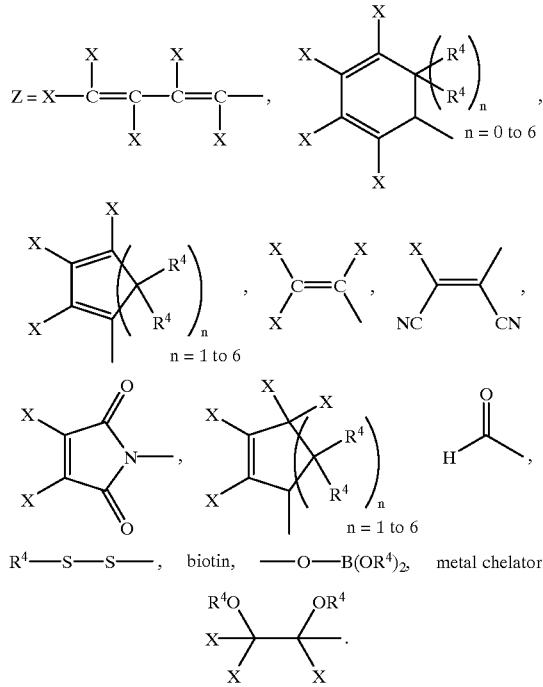

For the purposes of this invention "nucleobase" will have the following definition. A nucleobase is a purine or a pyrimidine base. Nucleobase includes all purines and pyrimidines currently known to those skilled in the art or any chemical modifications thereof. The purines are attached to the ribose ring through the nitrogen in the 9 position of the purine ring and the pyrimidines are attached to the ribose ring through the nitrogen in the 1 position of the pyrimidine ring. The pyrimidine can be modified at the 5- or 6- position of the pyrimidine ring and the purine can be modified at positions 2-, 6- or 8- of the purine ring. Certain modifications are described in copending U.S. patent applications Ser. Nos. 08/264,029, filed Jun. 22, 1994, entitled "Novel Method of Preparation of Known and Novel 2'Modified Pyrimidines Intramolecular Nucleophilic Displacement" and 08/458,421, filed Jun. 2, 1994, entitled "Palladium Catalyzed Nucleoside Modifications—Methods Using Nucleophiles and Carbon Monoxide" and U.S. Pat. No. 5,428,149, entitled "Method for Palladium Catalyzed Carbon-Carbon Coupling and Productions" which are herein incorporated by reference. More specifically a nucleobase includes, but is not limited to, uracil, cytosine, N4-protected cytosine, 4-thiouracil, isocytosine, 5-methyluracil (thymine), 5-substituted uracils, adenine, N6-protected adenine, guanine, N2-protected guanine 2,6-diaminopurine, halogenated purines as well as heterocycles meant to mimic the purine or pyrimidine ring, such as imidazole.

The term "peptide" as used herein refers to a polymer of amino acids chemically bound by amide linkages (CONH). An "amino acid" is defined as an organic molecule containing both an amino group ($NH_2$) and a carboxylic acid (COOH). Specifically an "amino acid" is any compound of the general formula $R^5CH(NH_2)COOH$ (α-amino acid), wherein $R^5$ is selected from the group consisting of H or any suitably protected known amino acid side chain. Suitable protection for amino acid side chains is known to those skilled in the art. As used herein the term "peptide" includes peptides, polypeptides and proteins. The peptides synthesized by the method of this invention are depicted generally as follows:

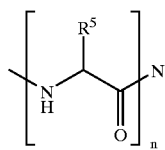

wherein n=1–500, and $R^5$ is as defined above.

The "N-protected amino acid monomer units" of this invention are generally depicted as follows:

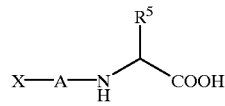

wherein $R^5$ is as defined above; and
A-X is a nitrogen protecting group(s) which serves as an anchor for partitioning the successfully reacted peptide product away from the unreacted peptide starting material. A-X can be any group that enables the partitioning of the "growing peptide chain" or "peptide product" away from unwanted side products and starting materials and is compatible with conventional peptide synthesis. In a preferred embodiment A is selected from the many reported N-protecting groups which are known to those in the art, including but not limited to urethanes, such as Fmoc and Boc, benzyl groups, acyl groups, or triphenylmethyl groups. X is designed to react with a substituent Y on a resin with high selectivity. X is selected from groups such as dienes, in particular 3,5-hexadienoxy or sorbic amide, dienophiles, in particular maleimide, alkynes, silylether protected diols and disulfides. The corresponding substituent Y is chosen to be a selective covalent reaction partner for substituent X, such as a dienophile, diene, mercaptane, or borate.

"Starting material" as used herein refers to the compound that is reacted with the 5'-protected monomer unit during each cycle of PASS to produce an oligomer that has been extended by one or more nucleotides. The starting material can be designed to produce a [5',3'] linkage between nucleotides or a [3',3'] linkage between nucleotides, depending on the desired oligonucleotide product. In the first instance the starting material is a 5'-deprotected otherwise protected oligonucleotide of length n, in the second case the starting material is a 3'-deprotected otherwise protected oligonucleotide of length n. Typically the starting material is a 5'-deprotected otherwise protected oligonucleotide of length n, wherein n is an integer from 1–1000. The starting material is 2',3'-protected by protecting groups, such as base labile groups, that are compatible with the reaction of the 5'-protected monomer units with the starting material and with 5'-deprotection reactions. Additionally, because the PASS process consists of the controlled and sequential polymerization of an oligonucleotide, the starting material of one PASS cycle is typically the deprotected product from the previous PASS cycle. Because the PASS process does not require that the 3'-terminal nucleotide be anchored to a solid support, the starting material can include non-nucleoside modifications. Non-nucleoside modifications can be introduced to the 3'-terminus which would not ordinarily be possible by solid phase synthesis. Non-nucleoside modifications to the 3'-terminus of the starting material include, but are not limited to, the use of polyethylene glycol mono-methylether (molecular weight 5,000 to 100,000) (PEG) or other high molecular weight non-imnmunogenic units as the 3'-terminal monomer for preparation of oligonucleotides with improved pharmacokinetic properties.

"Peptide starting material" refers to the compound that is reacted with N-protected amino acid monomer unit during each cycle of PASS to produce a peptide product that has been extended by one or more amino acids. In this instance starting material is an N-terminal deprotected otherwise protected peptide of length n, wherein n is an integer from 1–500. Additionally, because the PASS process consists of the controlled and sequential polymerization of a peptide, the starting material of one PASS cycle is typically the deprotected product from the previous PASS cycle. The peptide is protected using protecting groups and methods known to those reasonably skilled in the art. The carboxy terminal protecting group can be selected from a standard protecting group, a soluble polymer or a diagnostic detector.

"Product" as used herein refers to an oligonucleotide that is produced by the covalent reaction of the 5'-protected monomer unit with the starting material during each PASS cycle. As stated above, if the starting material is a 5'-deprotected oligonucleotide of length n and the 5'-monomer unit is a single nucleotide, the product of the reaction will be a 5'-protected oligonucleotide of length n+1. If the 5'-protected monomer unit is an oligonucleotide block of length m the product of the reaction will be a 5-protected oligonucleotide of length n+m. The product from a particular PASS cycle is then 5'-deprotected and becomes the starting material for the next cycle.

"Peptide Product" as used herein refers to a peptide that is produced by the covalent reaction of the N-protected amino acid monomer unit with the peptide starting material during each PASS cycle. If the peptide starting material is a N-terminal deprotected peptide of length n and the N-protected amino acid monomer unit is a single amino acid, the product of the reaction will be an N-terminal protected peptide of length n+1. If the N-protected amino acid monomer unit is a peptide block of length m the product of the reaction will be an N-terminal protected peptide of length n+m. The product from a particular PASS cycle is then N-deprotected and becomes the starting material for the next cycle.

A "failure sequence" refers to the starting material from a particular PASS cycle that fails to react with the 5'-protected monomer unit or N-protected amino acid monomer unit during that cycle.

"Growing oligonucleotide chain" refers to either a 5'-deprotected oligonucleotide chain or a 5'-protected oligonucleotide chain that has been prepared by the sequential addition of nucleotides (N) beginning with the 3'-terminal nucleotide of the desired nucleotide using the method of this invention. After each reaction cycle of the PASS process the growing oligonucleotide increases in length by at least one oligonucleotide, and becomes the starting material for the next reaction cycle. As used herein the term can refer to either starting material or product and one of ordinary skill in the art will recognize what is intended by the term in a particular context.

Scheme 2 generally illustrates the method of this invention. A 5'-protected monomer unit, such as phosphoramidite 7, is added to a starting material 8 in solution, in the presence of an activator, such as tetrazole or preferably 4,5-dicyanoimidazole (DCI) (see U.S. patent application Ser. No. —, filed Oct. 15, 1996, entitled "Improved Coupling Activators for Oligonucleotide Synthesis"), to yield a product 9 to which one nucleotide has been added via a phosphite triester linkage. As depicted in this figure the starting material 8 is a 5'-deprotected otherwise protected oligonucleotide of length n, wherein n is an integer between 1 and 1000, and the product is a 5'-protected oligonucleotide of length n+1. The 5'-deprotected oligonucleotide starting material 8 is not anchored to a solid support, but rather, using standard methods, is simply 2', 3'-protected by protecting groups, such as base labile groups, that are compatible with the reaction of the 5'-protected monomer units with the starting material and with 5'-deprotection reactions. The elimination of 3'-anchoring to a solid support enhances the scope of the 3'-modifications that can be incorporated into oligonucleotides. Additionally, the 3'-terminal nucleotide no longer has the requirement of bearing the hydroxyl substituent needed for support anchoring. Thus, modifications can be introduced to the 3'-terminus which are not possible by solid phase synthesis. This includes, but is not limited to, the use of polyethylene glycol mono-methylether (molecular weight 5,000 to 100,000) or other high molecular weight non-immunogenic units as the 3'-terminal monomer for preparation of oligonucleotides with improved pharmacokinetic properties. (See U.S. patent application Ser. No. 08/434,465, filed May 4, 1995, entitled "Nucleic Acid Ligand Complexes," which is incorporated herein by reference).

After completion of the reaction between the 5'-protected monomer unit 7 and starting material 8, the reaction mixture contains three species: unreacted 5'-protected monomer unit 7, unreacted starting material 8, and the product of the reaction, compound 9, which is a 5'-protected oligonucleotide of length n+1. As discussed above any of the starting material 8 (a 5'-deprotected oligonucleotide of length n) which fails to react with the 5'-protected monomer unit 7 is referred to as the failure sequence, as this sequence was not extended. The product of the reaction, compound 9, is a 5'-protected oligonucleotide chain extended by one nucleotide (length n+1), by the covalent reaction of the 5'-hydroxy group of starting material 8, an oligonucleotide of length n with the 3'-phosphoramidite group of the 5'-protected monomer unit 7. The product, compound 9, is the major component and the 5'-protected monomer unit 7 and the starting material 8 that did not react are present only in minor amounts.

At this stage of the process it is necessary to remove the unreacted 5'-protected monomer unit from the reaction mixture, both to purify the materials and to recover the monomer starting material. According to this embodiment, non-reacted monomer is reacted to form an easily removable ionic species. Oxidation of the phosphite triester to phosphate triester may be carried out in the same reaction flask simply by addition of an oxidizing agent. In situ oxidation gives the desired oligonucleotide product 9, the phosphate salt 10 of monomer 7, as well as unreacted oligonucleotide starting material 8. The monomer phosphate salt 10 is the only free salt in the reaction mixture and thus is easily removed by techniques known to those in the art, including but not limited to, filtration through an anion exchange resin or membrane or extraction with an aqueous phase. In an alternate variation of this embodiment of the invention, the 3'-terminal monomer is a polyethylene glycol mono-methylether of molecular weight 5,000 to 100,000, preferably 20,000. In this case, a simple molecular weight cut-off membrane can be used to remove monomer 10.

After the unreacted monomer has been removed from the reaction mixture, the remaining filtrate may then be partitioned in any manner suitable to separate the "oligonucleotide product" from the "failure sequence." In one embodiment, the filtrate is applied to a material designed to interact selectively or specifically with the 5'-protecting group (D-E), such as a reverse phase resin. The product is captured or retained on the solid support by affinity of the 5'-protecting group constituent D with the resin. In a preferred embodiment, the filtrate is applied to a material designed to covalently react with the 5'-protecting group (D-E), such as a dienophile derivatized resin where D contains a diene unit. The product is captured or retained on the solid support by covalent reaction of the 5'-protecting group constituent D with the resin. The unreacted oligonucleotide starting material 8, which does not carry the 5'-protecting group D, is washed away. The unreacted starting material may be isolated and stored to be used as an intermediate in a subsequent synthesis. The retained oligonucleotide product 9 is then released from the resin according to well known procedures. In certain embodiments, the oligonucleotide product is released by cleavage of the bond between the 5'-oxygen and the protecting group D-E. For example, when the 5'-protecting group is a trityl derivative, a reagent such as dilute dichloroacetic acid (DCA) may be used to cleave the trityl group, thereby releasing the oligonucleotide coupling product. The liberated 5'-deprotected oligonucleotide coupling product 11 can then be used as the starting material in an additional coupling reaction.

SCHEME 2

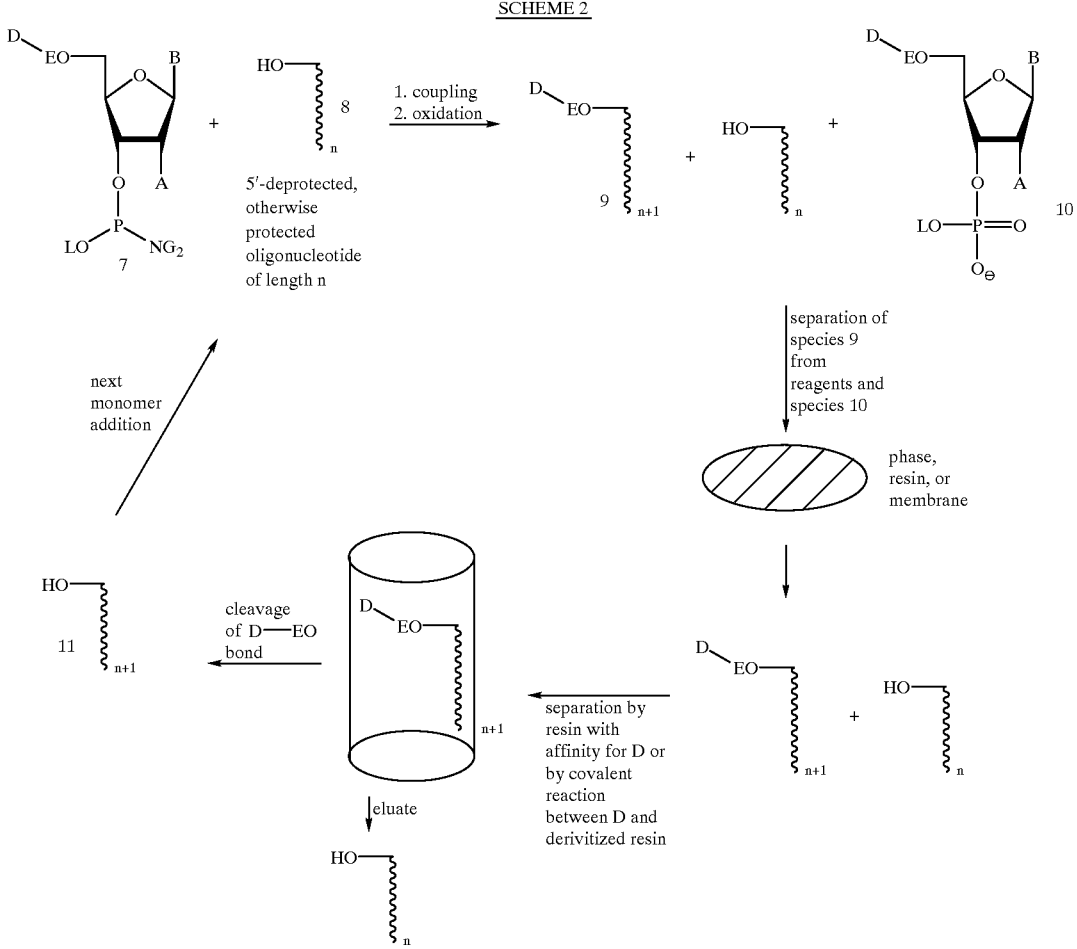

It is not a requirement of the present invention that the steps in the monomer addition cycle depicted in Scheme 2 occur in the exact sequence described above. Alternatively, coupling and oxidation in situ can be followed by covalent or affinity capture of the product and of monomer 10 on a resin. Subsequent cleavage of the 5'-protecting group liberates both the product and the monomer. At this stage an extraction or membrane-based filtration easily removes the unwanted monomer byproduct.

Utilization of the 5'-protecting group for anchoring of the oligonucleotide product allows for the possibility of using a wide variety of 3'-terminal modifications. These can be groups designed to facilitate separation of the product of the reaction from the 5'-protected monomer unit, such as a polymer of sufficient molecular weight to exploit molecular weight cut-off membranes for this separation, or a metal chelator to effect selective precipitation of the product. In such a case these groups contain a cleavable linker between the 3'-terminus of the oligonucleotide and the modifying group, such as a succinate linker. Alternatively, nonnucleoside 3'-terminal substituents may enhance pharmacokinetic properties of oligonucleotide products, such as a polyethylene glycol mono-methylether or a distearyl glycerol. (See U.S. patent application Ser. No. 08/434,465, filed May 4, 1995, entitled "Nucleic Acid Ligand Complexes," which is incorporated herein by reference). The 3'-terminal monomer may also serve as a detector for diagnostic applications of oligonucleotides, such as a chelator designed to retain Tc99m for in vivo imaging. (See Patent Application No. WO 96/02274, published Feb. 1, 1996, entitled "Conjugates Made of Metal Complexes and Oligonucleotides, Agents Containing the Conjugates, Their Use in Radiodiagnosis as well as Process for Their Production," which is incorporated herein by reference). In conventional solid phase oligonucleotide synthesis the 3'-terminus is not accessible for introduction of such constituents since it is utilized to anchor the growing chain to the solid support.

In contrast to the conventional solid phase synthesis process, the oligonucleotide product is preferably separated from unreacted starting material each time a new coupling reaction is performed. Thus, the final oligonucleotide product is obtained in essentially pure form and the cumbersome removal of highly homologous failure sequences is eliminated. Additionally, because the reaction is performed in the solution phase, the yields of the reaction of the monomer with the oligonucleotide starting material are also significantly increased. Furthermore, a capping step becomes superfluous in this scheme, since only successful oligonucleotide coupling products enter the next step of the process. The elimination of the capping step amounts to another efficiency gain compared to the conventional process. The oligonucleotide starting material that failed to undergo reaction with the 5'-protected monomer unit (failure sequence) is instead isolated and may be reused. Each time a failure sequence is reisolated during a PASS iteration, it can be blended into the starting material at the same step or iteration in a subsequent synthesis of the same oligomer, or of an oligomer that shares the same 3'-terminal fragment. (See Scheme 3). Failure sequences, therefore, become useful sequential building blocks for the subsequent manufacture of oligonucleotides. This not only increases the efficiency of the process, it also dramatically increases the purity of the final crude product. It further allows using the monomer as the limiting reagent and thus, dramatically increases process efficiency.

oligonucleotide batch either after every monomer addition (in solution phase oligonucleotide synthesis processes) or after cleavage of the crude oligonucleotide from the solid support (in conventional solid phase oligonucleotide synthesis processes). In yet another application, the reaction of a diene modified trityl group with a dienophile modified resin allows facile preparation of cation exchange resins.

A dimer of 2'-fluoropyrimidine modified RNA oligonucleotides is assembled by the PASS process in Example 1

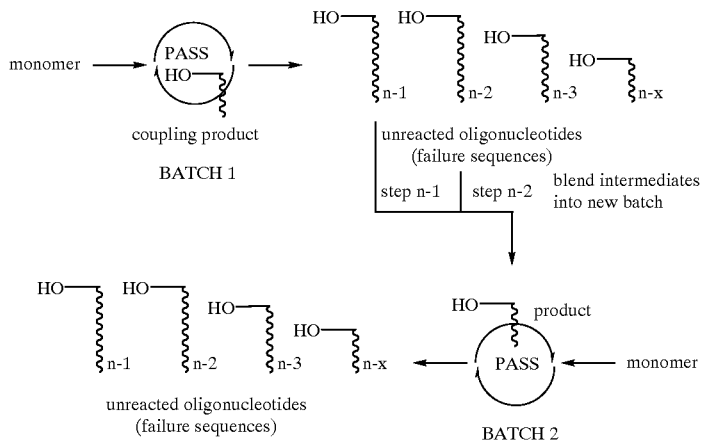

SCHEME 3

The outlined synthetic scheme, which exploits the 5'-protecting group as the anchor for separation of product from starting materials and allows failure sequences to become intermediates for subsequent syntheses, is not limited to phosphoramidite coupling chemistry. It is compatible with other coupling reactions, such as, H-phosphonate or phosphate triester coupling chemistry. (See Gaffney and Jones (1988) Tetrahedron Lett. 29:2619–2622). This scheme also lends itself to automation of oligonucleotide synthesis and is ideally suited for the large scale manufacture of oligonucleotides with high efficiency.

Aspects of the technology described here have applications beyond the PASS synthesis process. For instance, the covalent capture of desired or unwanted species in oligonucleotide synthesis can also be applied to a high resolution, single-step purification method in conventional solid phase or solution phase processes. If only the terminal monomer bears a diene modified trityl group at its 5'-terminus, then selective anchoring of the full length product on a dienophile derivatized resin or membrane removes all major failure sequences from the crude mixture. (See Scheme 1). In another application, if a capping reagent is used which contains a moiety suitable for covalent capture (all D groups described above apply), such as a diene-modified acetic anhydride (or generally a D-modified acetic anhydride) or diene modified silyl chloride, such as 3,5-hexadienoxyacetic anhydride or tri-(3,5-hexadienoxy)silyl chloride, then all capped failure sequences can be removed from a crude (Scheme 4). In the first reaction phosphoramidite coupling chemistry is employed to form a 3',3'-phosphodiester linkage. Oligonucleotides are often protected against 3'- to 5'-exonucleolytic degradation by incorporation of a 3',3'-phosphodiester linkage at the 3'-terminus. After coupling, the reaction mixture is oxidized in situ to produce unreacted thymidine starting material 12, oxidized amidite monomer 15, and oxidized dimer product 14.

Figure 3:
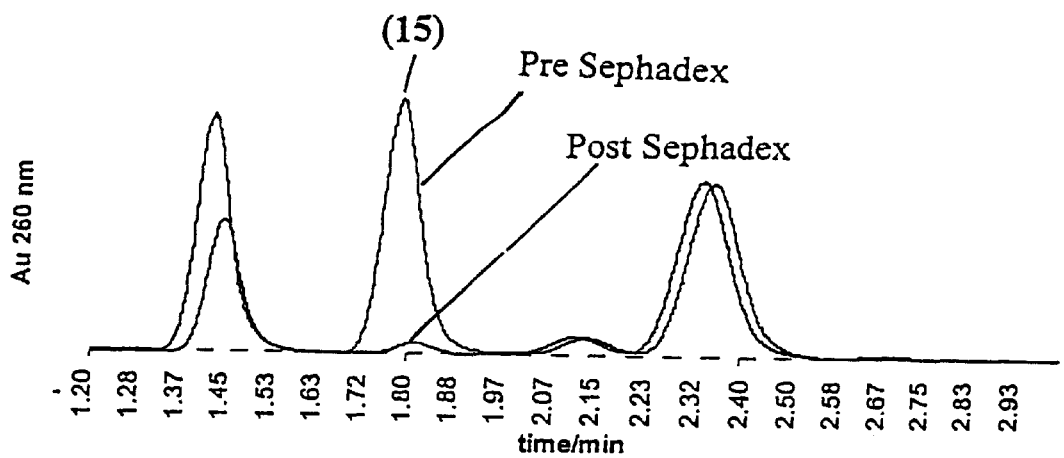
FIG. 3 illustrates the reverse phase HPLC traces of a mixture of oxidized phosphoramidite coupling reaction set forth in Example 1, both prior to and after being passed through a DEAE Sephadex® filter plug.
Figure 4:
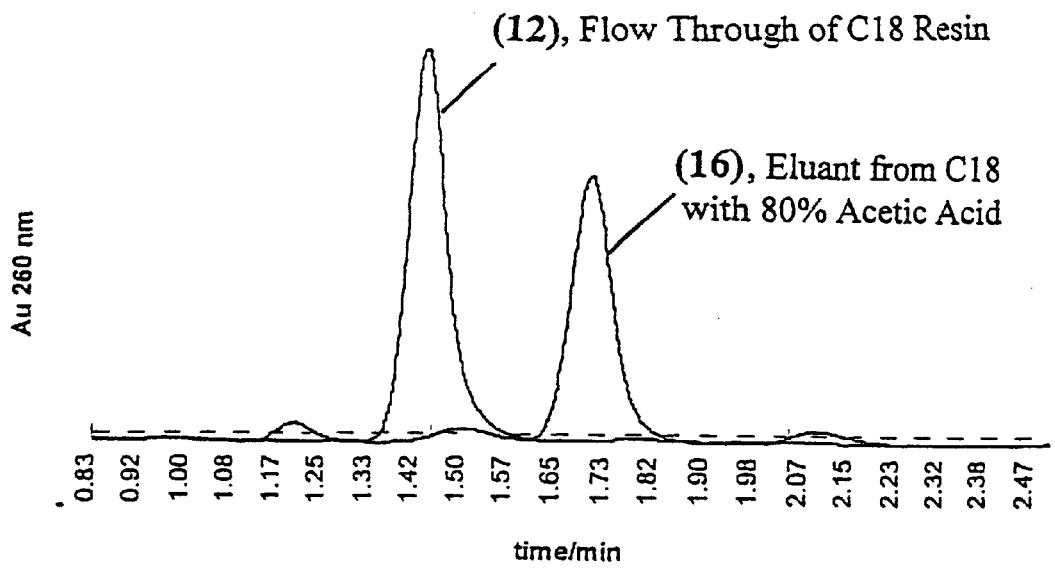
FIG. 4 illustrates the reverse phase HPLC traces of the oxidized phosphoramidite coupling reaction set forth in Example 1, after being eluted through a C18 resin with water/acetonitrile and after treatment with acetic acid and elution with water/acetonitrile.

The oxidized amidite monomer 15 is removed by filtering the reaction mixture through a bed of diethylaminoethylene (DEAE) Sephadex®. HPLC analysis of the filtrate indicates that the oxidized amidite monomer 15 has been retained by the DEAE Sephadex® as shown in FIG. 3. The filtrate, which contains the oxidized dimer product 14 and the unreacted thymidine starting material 12, is concentrated and redissolved in 60% acetonitrile/water and loaded onto a C18 filter plug. The resin is washed with 70% water/acetonitrile followed by 50% water/acetonitrile to fully elute the unreacted thymidine starting material 12. The resin, which now contains only the tritylated dimer product 14 is then washed with water, followed by treatment with 80% acetic acid/water to effect detritylation. The resin is then washed with 50% acetonitrile/water, which elutes the final product 16, while retaining the trityl species (FIG. 4).

SCHEME 4

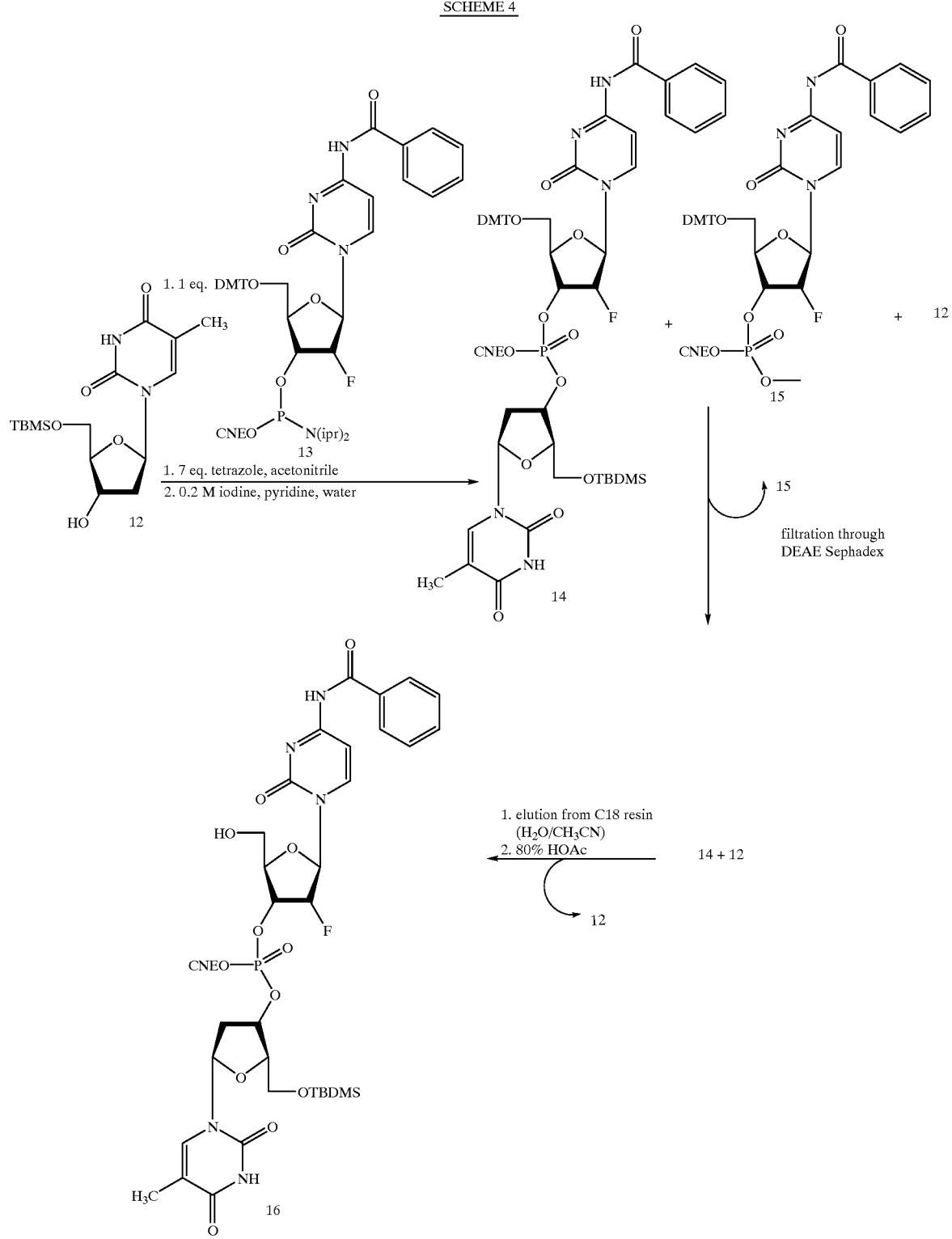

Example 2 (Scheme 5) illustrates the method of this invention, wherein the 5'-protected monomer unit is an H-phosphonate, rather than a phosphoramidite. In this example an H-phosphonate thymidine trimer bearing a 3',3'-internucleotidic linkage at the 3'-terminus (T-T-[3',3']-T trimer) 20 is prepared. The efficiency of the liquid phase coupling reaction was so high, that no unreacted 3'-terminal fragment 19 was detected. Thus, the reverse phase step is used only to cleave and separate the trityl group from the product.

Example 3 (Scheme 6) describes the synthesis of a phosphoramidite monomer containing 5'-O-(4,4'-dioctadecyloxytrityl) (DOT) as the 5'-protecting group (D-E).

Example 4 illustrates the ability to separate the coupling product from the unreacted oligonucleotide starting material (failure sequence) based upon the selective or specific interaction of the 5'-protecting group (D-E) with a particular resin or phase. In this example, the mobility of 4,4'-dioctadecyltriphenylmethanol (DOT) 23 on a C18 reverse phase resin is compared to that of 4-decyloxy-4'-methoxytritanol and dimethoxytritanol (DMT) (see Table 1). The strong interaction of the DOT group with C18 resin in organic solvents, such as methanol ($R_f$=0) and acetonitrile ($R_f$=0) enables the one-step separation of product from starting material by loading the mixture onto C18 resin and washing the unreacted starting material away with an organic solvent. The coupled product can then be eluted from the chamber by cleavage of the trityl protecting group with a haloacetic acid in an organic solvent. The trityl group is retained on the resin.

Example 5 describes the assembly of a hexamer oligonucleotide (5'-HO-T-T-A-C-T-[3',3']-T) in solution using an anion exchange medium to remove the excess monomer and C18 reverse phase resin to selectively capture the 5'-DMT protected product while not retaining the failure sequence. As can be seen in Example 5, each monomer addition is accomplished in two steps. In the first step phosphoramidite coupling chemistry is employed to couple the 5'-protected monomer unit to the starting material. After coupling, the reaction mixture is oxidized in situ to produce unreacted starting material (failure sequence), oxidized amidite monomer, and oxidized product. The oxidized amidite monomer is removed by filtering the reaction mixture through an anion exchange medium, such as, DEAE Sephadex®.

In the second step the filtrate, which contains the oxidized product and the unreacted starting material (failure sequence), is treated with a dilute acid to effect detritylation. Examples of dilute acids which can be used include, but are not limited to, dilute mineral acids, dilute trichloroacetic acid, dilute dichloroacetic acid (DCA), Lewis acids, such as, $ZnBr_2$, nitromethane, tosic acid and perchloric acid. The mixture is then separated by chromatography. Alternatively, the mixture of product and unreacted starting material is first separated using a reverse phase resin followed by detritylation to release the detritylated product from the resin. The analytical data provided in Example 5 shows that the PASS process produces essentially pure oligonucleotide intermediates at every iteration with minimal consumption of cost-limiting monomer.

Example 6 (FIG. 5) illustrates schematically an automated extraction/filtration system 110 designed for use with the method of this invention, to separate the unreacted 5'-protected monomer unit from the remainder of the reaction mixture. As stated above, the method of this invention lends itself to automation and is thus ideally suited for large scale manufacture of oligonucleotides. The automated extraction/filtration system 110 has two centers: an extraction vessel 112 and a chromatography resin filtration chamber 114. The extraction vessel is in fluid communication with the chromatography resin chamber by a tube 118. A first three way valve 120 controls the flow of the contents from the extraction vessel 112 into the chromatography chamber 114. A second valve 122 controls the addition of solvents into chamber 114. A third valve 124 controls the collection of effluent out of chamber 114. All three valves are electronically coupled to a controller 126, that provides signals that actuate all three valves 120, 122, and 124 between their various flow positions.

Extraction vessel 112 is equipped with two inlet ports, 128 and 130, a stirrer 132, and an outlet port 134. The reaction mixture is pumped into the extraction vessel 112 through inlet port 128 and an extraction solvent, such as $CH_2Cl_2$, and an aqueous buffer are pumped into the extraction vessel through inlet port 130. The mixture may be agitated with stirrer 132, after which time the layers are allowed to separate. The first three way valve 120 is then opened and the bottom organic layer flows through outlet port 134, into a conductivity monitor 136 and then through tube 118 into chamber 114. The conductivity monitor is electronically coupled to the controller 126. A rise in conductivity indicates that the organic layer has passed through the conductivity monitor and the aqueous layer has begun to enter. The rise in conductivity is recognized by the controller 126 which sends a signal to the first three-way valve 120 actuating the three-way valve to divert the aqueous layer away from chamber 114.

Chamber 114 is equipped with three inlet ports 138, 140, and 142 and an outlet port 144. The organic layer enters chamber 114 through inlet port 138 and is pushed through the chamber 114 with a pressurized inert gas source, such as argon, which enters the chamber through inlet port 140. The chamber is then washed with solvent, i.e., $CH_2Cl_2$, which enters the chamber through inlet port 142. The addition of solvent is controlled by the controller which selectively actuates the second valve 122. The organic effluent is collected through outlet port 144 by opening of the third valve 124 by the controller 126. The organic effluent contains the product of the reaction, which is the starting material extended by one nucleotide and unreacted oligonucleotide starting material (failure sequence). The unreacted 5'- protected monomer is retained in the chamber 114. After elution of the organic solvent, the chamber 114 is washed with a buffered solution, added through inlet port 140, which elutes the unreacted 5'-protected monomer unit. Chamber 112 is then re-equilibrated with the organic solvent being used to elute the reaction mixture, i.e., $CH_2Cl_2$. The organic effluent is next passed over a reverse phase resin, to separate the product from the unreacted oligonucleotide starting material (failure sequence). (See Example 6).

Example 7 describes the solution phase synthesis of the 15 base oligonucleotide (5'-CTAAACGTAATGG-[3',3']-T-T-3') (SEQ ID NO: 1) using polyethylene glycol of 20,000 molecular weight as a 3' residue modification. This example demonstrates the efficiency of solution phase synthesis and the potential for preparing 3'-modified oligonucleotides in solution which can not be directly prepared using conventional solid phase synthesis. This example outlines the basic steps required for solution phase synthesis without the step wherein the oligonucleotide coupling product is captured on a resin as in a typical PASS cycle. Thus, this example also demonstrates the impact on efficiency and product purity that product capture provides as envisioned in PASS. With such product capture at each monomer addition cycle, cumbersome precipitations from diethyl ether are no longer necessary as in conventional solid phase synthesis. Additionally, because failure sequences are removed at each monomer addition cycle, the anion exchange chromatogram of the product obtained by PASS is expected to only show a single product peak, rather than the multiple peaks present in the chromatogram of FIG. 6.

Example 8 (Schemes 7 and 8) describes the synthesis of various diene modified trityl alcohols including a 5'-di-(3, 5-hexadienoxy)tritylthymidine phosphoramidite monomer (32) and a 5'-di-(2,4-hexadienoxy)tritylthymidine phosphoramidite monomer.

Example 9 (Scheme 9) demonstrates the use of dienes—4,4'-di-3,5-hexadienoxytrityl alcohol (30) and 4,4'-di-2,4-hexadienoxytrityl alcohol (36)—for efficient cycloaddition to maleimides (Reactions 1 and 2 respectively (Scheme 9)). Table 4 sets forth the reaction rates for these two reactions under various conditions. From the data set forth in Table 4, it is clear that modified trityl compound (30) reacts faster under the various reaction conditions. It is also clear that, as expected, both the increase in dienophile equivalents, as well as the addition of water to the reaction mixture increase the reaction rate. It is important to note reaction of greater than 50% of the diene substituents is sufficient for capture of all the trityl alcohol or nucleotide on a maleimide-modified solid phase support, since there are two dienes present on each trityl group. This reduces the time needed for the reaction to take place.

For rate comparison purposes the Diels-Alder reaction was carried out with 5'-O-(4,4'-di-3,5-hexadienoxytrityl)thymidine (5'-(DHDT)thymidine) (31) and with 5'-O-(4,4'-di-3,5-hexadienoxytrityl)thymidine 3'-phosphoramidite (32) under the same reaction conditions given for reaction #93 (Table 4). The results are set forth in Table 5. Again, within 1 hour more than 50% of the diene groups underwent cycloaddition. This suggests that product capture, as envisioned in PASS, can occur within a reasonable time frame to allow rapid and efficient monomer addition cycles. It is widely known that the rate of Diels-Alder cycloadditions can be tailored by using suitably substituted dienes and dienophiles. Thus, the product capture reaction rate can be tailored by employing a suitable set of dienes and dienophiles.

Example 10 describes the preparation of 3'-PEG derivatized oligonucleotides by PASS using the 4,4'-di-3,5-hexadienoxytrityl protecting group for capture of the oligonucleotide product on a substituted maleimide-polystyrene resin. This capture step removes the non-reacted starting oligonucleotide (failure sequence) from the reaction mixture. The latter can optionally be isolated and stored for blending into a subsequent production batch at the same point in the oligonucleotide assembly. A 3'-PEG terminal modification is useful inter alia, for enhancing the pharmacokinetic behavior of therapeutic oligonucleotides in vivo.

Example 11 describes a general reaction scheme for the preparation of non-PEG derivatized oligonucleotides by Diels-Alder product capture using a 5'-O-(4,4'-di-3,5-hexadienoxytrityl)-nucleoside (5'-O-DHDT-nucleoside) 46 as the diene and a maleimide substituted solid support 45 as the dienophile. (Scheme 11). As discussed above, the capture of full length oligonucleotides on a resin or membrane is integral to automating the PASS process. The general design of the capture involves a trityl group or trityl analog being irreversibly bound to a solid support, such as a resin, membrane, or polymer 47. Once bound, the oligonucleotide 49 is released by separating it from the irreversibly bound trityl group 48. An example of this is the Diels-Alder capture of the 5'-O-DHDT-nucleoside. Resin-bound active Diels-Alder dienophiles covalently react with diene trityls and conventional methods of detritylation release the nucleoside from the solid support and bound trityl group. This capture can be employed to prepare non-PEG derivatized oligonucleotides by PASS as described in Example 11 (Scheme 12).

SCHEME 11

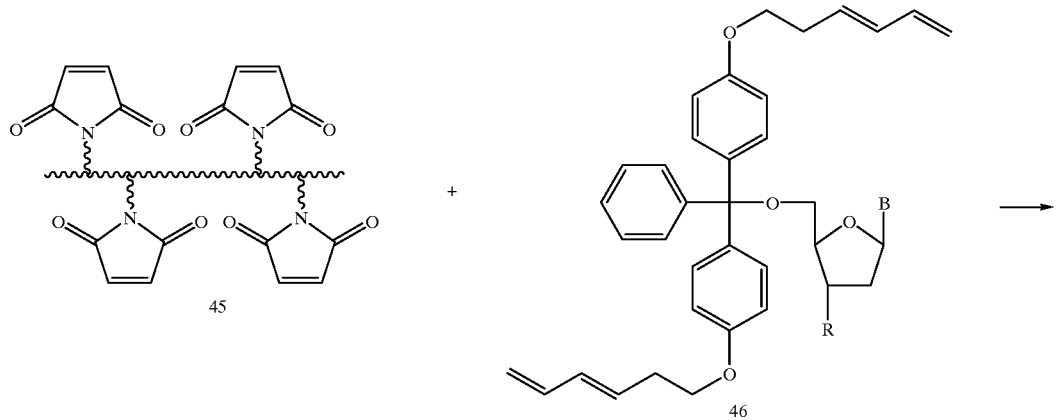

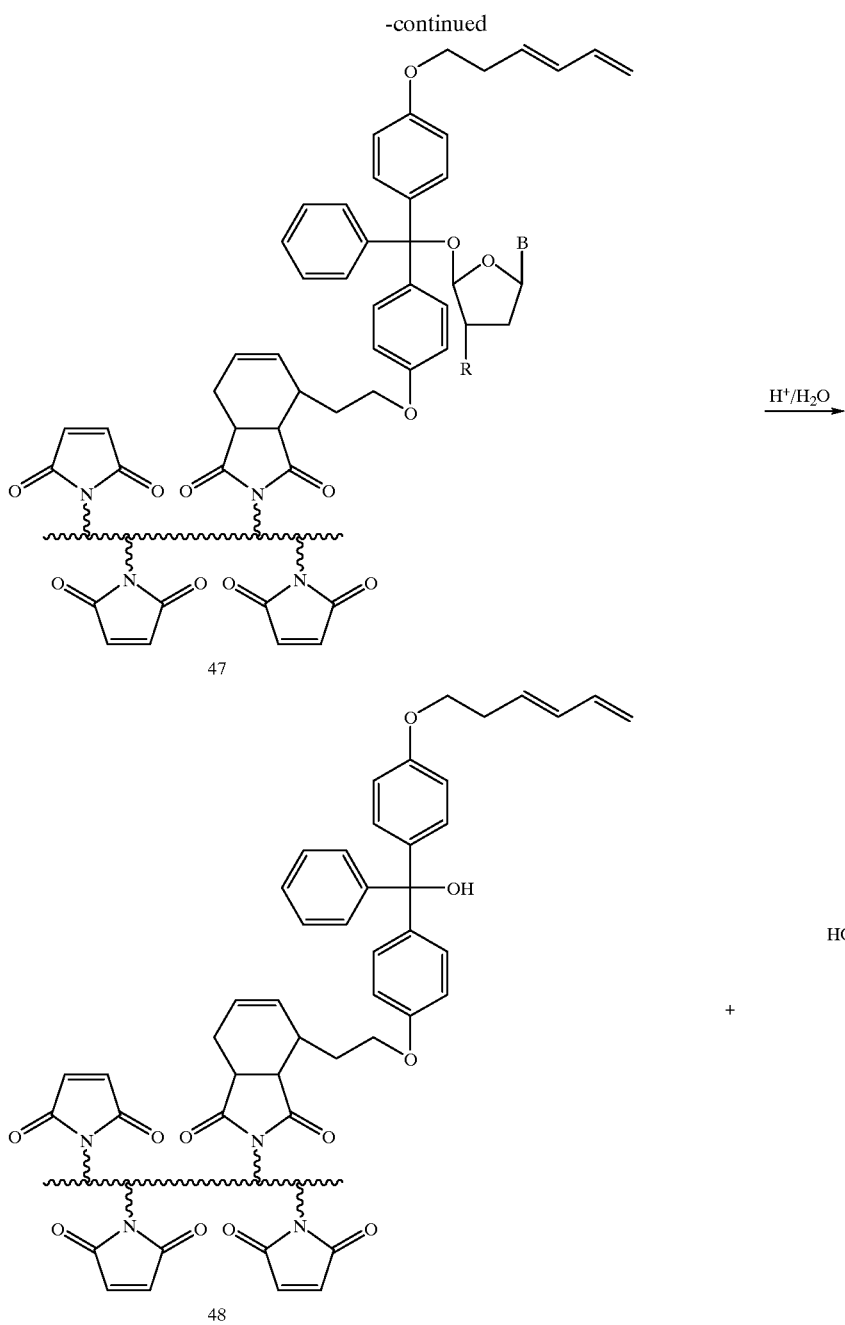

A number of solid supports are envisioned to be suitable for capture and release using the Diels-Alder reaction. Preferred solid supports are inorganic oxides (silica, alumina, zeolites, controlled pore glass (CPG), etc.) that have surface hydroxyl groups that can be readily functionalized. With the possible exception of CPG, these inorganic solid supports often have a much higher loading capacity than commercially available resins. Traditionally, these inorganic oxides have been functionalized by silylating the hydroxyls with a silylating agent that has a more versatile or reactive functional group. (Scheme 13).

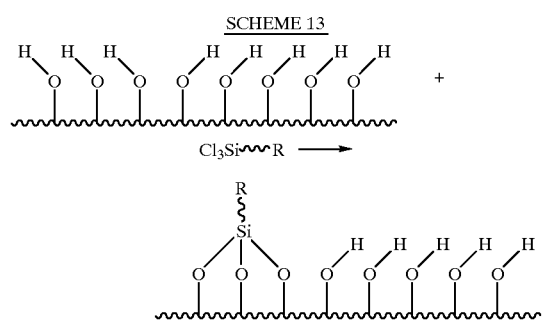

SCHEME 13

-continued

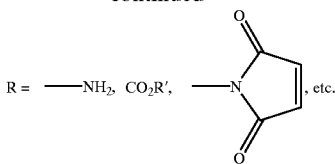

Other methods of covalently linking the reactive dienophile are also envisioned, for example, esterification between a molecule such as 6-maleimido-caproic acid and the surface hydroxyl group. (Scheme 14). Other covalent linkers between the surface and dienophile group may be used, if found to increase the surface loading and/or reactivity of the dienophile.

SCHEME 14

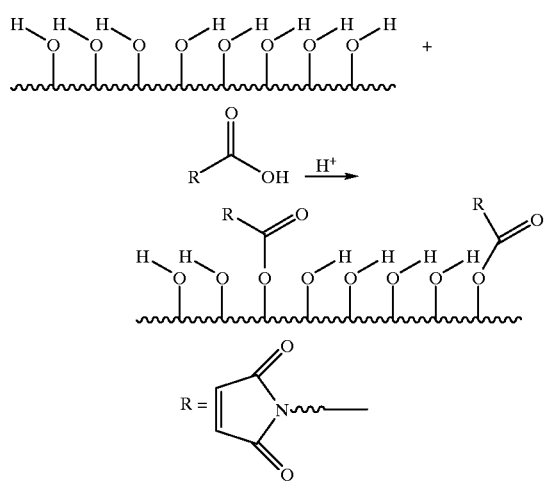

Example 12 (Scheme 15) describes the preparation of a dimer using product capture by Diels-Alder cycloaddition. The rate of capture of the 3',3'-linked 5'-DHDTO-T-T dimer is dependent on the excess of resin bound maleimide groups. Product capture proceeds quantitatively. The captured product is easily and quantitatively released from the resin with 3% dichloroacetic acid in dichloromethane. After neutralization and concentration, pure product is obtained.

Example 13 describes a method for assembly of oligonucleotides from blocks by capturing one of the blocks on a resin using the cycloaddition of a 5'-O-(4,4di-3,5-hexadienoxytrityl) protected oligonucleotide to a dienophile derivatized resin.

Example 14 (FIG. 8) illustrates schematically an automated extraction/filtration system 200 and process designed for the automated preparation of an oligonucleotide bearing a 3'-terminal polyethylene glycol using covalent capture of the monomer addition product at every cycle, as described in Example 10. As discussed above, the PASS process, which consists of a controlled, sequential polymerisztion of nucleoside phosphoramidites, can be performed in automated fashion. Each monomer addition consists of a sequence of chemical processing steps. This sequence remains the same for each monomer addition (cycle). The only variable from cycle to cycle is the nature of the monomer that is added. A typical oligonucleotide consists of 2 to 12 different monomers, which are added typically more than once in a dedicated, programmable sequence.

Figure 8:
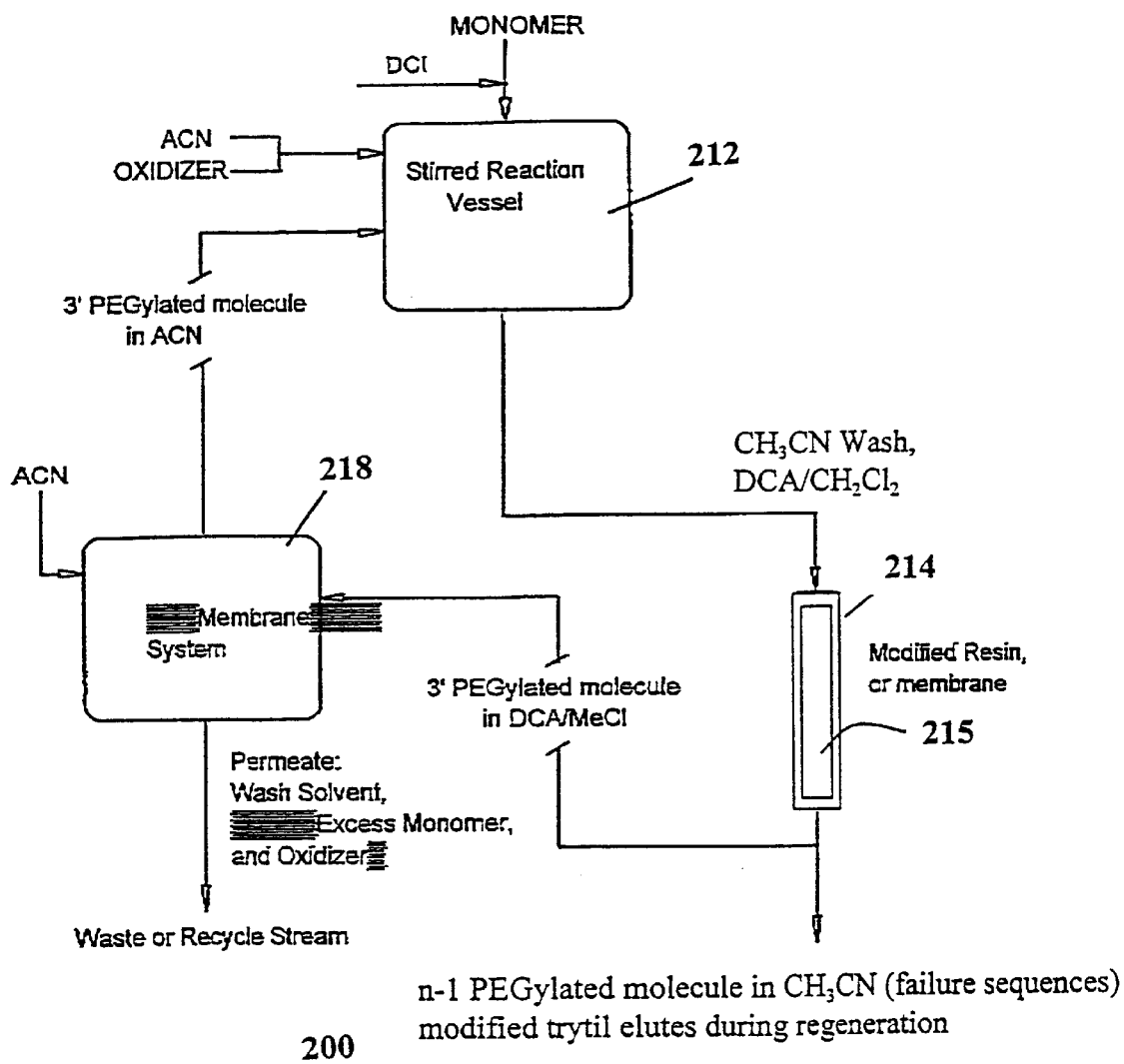
FIG. 8 illustrates schematically an automated extraction and filtration system designed for use with Diels-Alder product capture.

As can be seen in FIG. 8, the automated extraction/filtration system 200 has three centers: a reaction vessel 212, a filtration chamber 214—which contains the dienophile modified solid support 215—and an ultrafiltration membrane system 218.

Example 14 also lists various ultrafiltration membranes compatible with the conditions required for the separation of a product oligonucleotide and excess monomer after release from the capture resin. Membranes are evaluated based on reagent/product adsorption, retention, and reactivity. The membranes set forth in Example 14 were found to be suitable, based on flux rates as affected by solvent, loss of product due to adsorption, and finally by diffuse reluctance FTIR.

Figure 5:
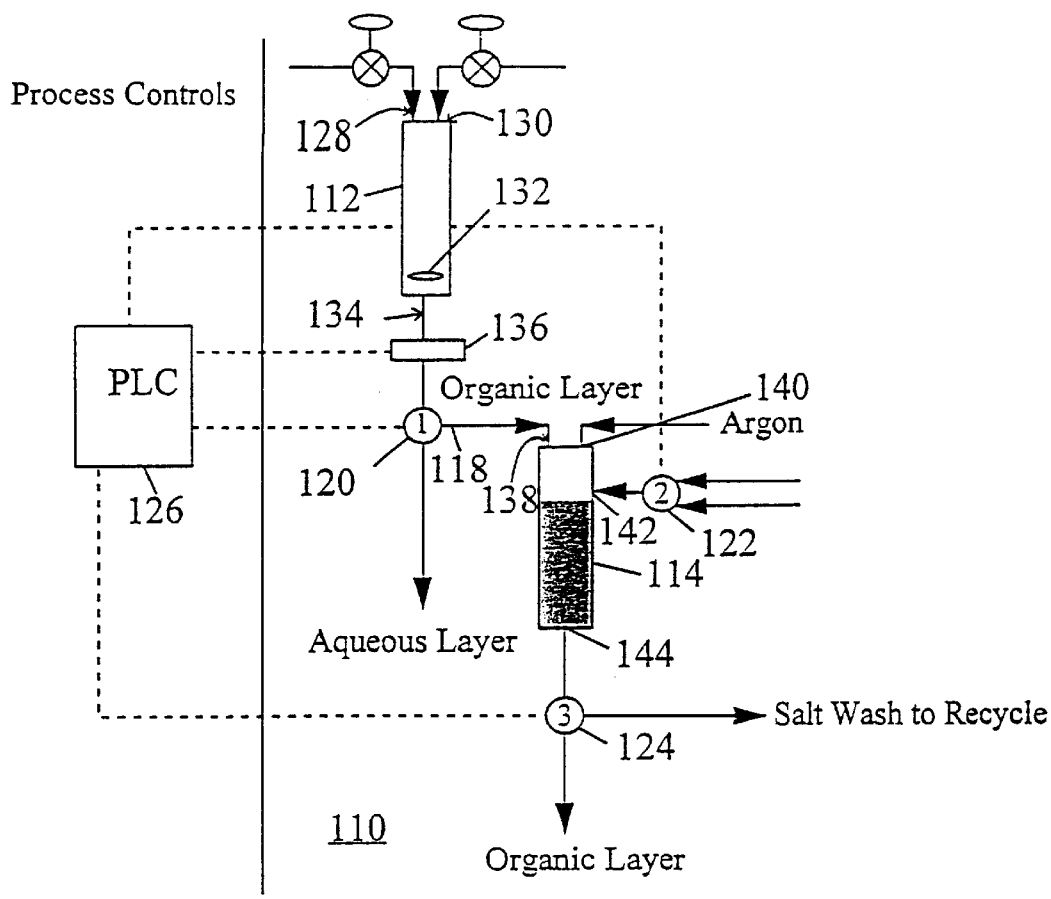
FIG. 5 illustrates schematically an automated extraction and filtration system designed for use with the method of this invention.

For purposes of illustration, the preparation of a 3'-terminal PEG oligonucleotide is described in Example 14, however, this automated method of synthesis can be done with or without a macromolecule attached to the oligonucleotide. In the latter case, the molecular weight cut-off membrane may be replaced by a liquid/liquid extraction step, as depicted in FIG. 5.

Example 15 describes the synthesis of maleimide derivatized trityl groups. As discussed above, an integral part of the PASS process is a method of removing n-1 sequences. One approach, is oligonucleotide synthesis using monomers containing a maleimide-modified trityl group. These trityl groups are susceptible to reaction with diene-modified resins allowing separation of n-1 by simple washing of the resin followed by detritylation to release the full-length oligonucleotide.

Example 16 describes the use of diene-modified capping reagents for the selective removal of failure sequences during solution phase synthesis and conventional solid phase synthesis. Typically, failure sequences are capped with acetic anhydride. The capping reaction with acetic anhydride proceeds rapidly and near quantitatively. Thus, diene modified analogs of acetic anhydride, such as, 3,5-hexadienoic acid anhydride (74) and 3,5-hexadienoxyacetic anhydride (75) (Scheme 18) allows efficient capping of failure sequences and also enables removal of the capped failure sequence by cycloaddition to a dienophile derivatized resin or membrane at each cycle during solution phase synthesis as described in Example 7. The 5'-acetyl capping groups introduced during conventional solid phase synthesis are removed during the ammonia cleavage and deprotection step. In order to utilize reagents 74 or 75 as capping reagents in solid phase synthesis and as subsequent handles for selective removal of the failure sequences, the oligonucleotide must be bound to the support via a linker, such as described in Example 12, which is selectively cleavable under non-basic conditions. Alternatively, a capping reagent can be used which is not susceptible to removal under the typical basic deprotection conditions used at the end of conventional solid phase synthesis.

The hexadienoxysilyl chlorides (76, 77 and 78), allow selective removal of the failure sequences once the crude oligonucleotide is cleaved from the support with ammonia. The silyl ether group is not removed under these conditions. Thus, the hexadienoxysilyl capped failures can be removed from the desired product by reaction with a dienophile derivatized resin or membrane.

SCHEME 18

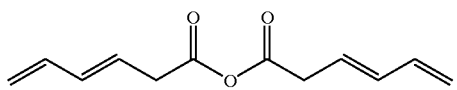

74

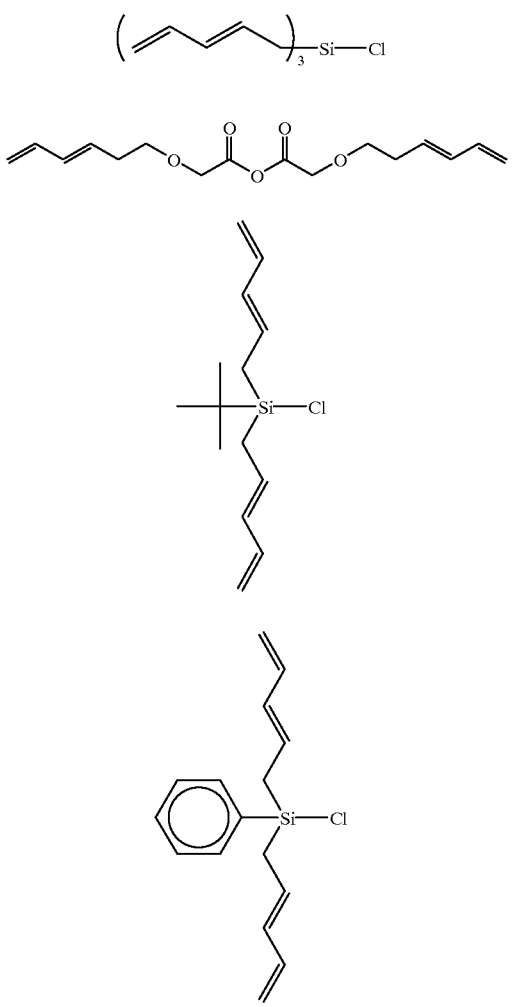

Figure 10:
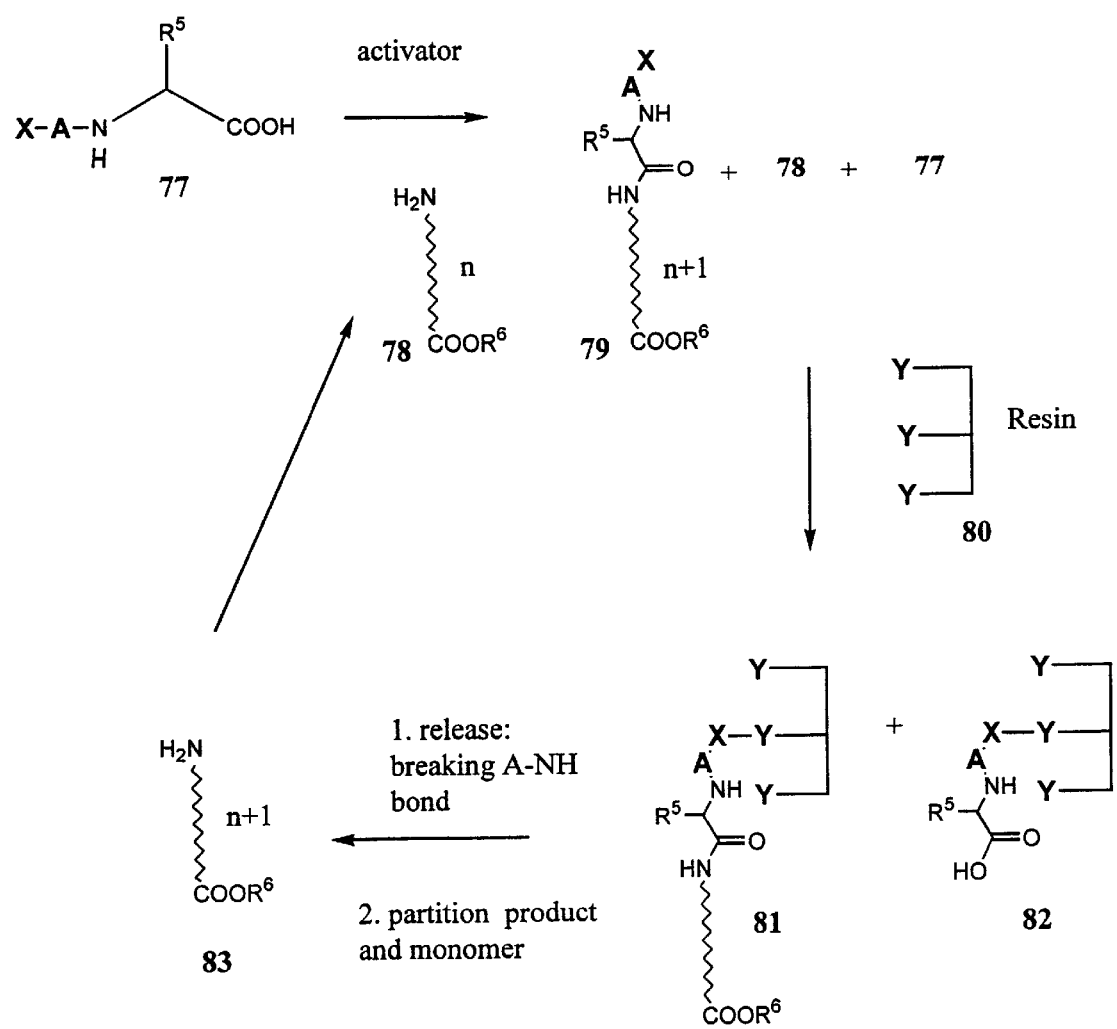
FIG. 10 illustrates the assembly of a peptide using Product Anchored Sequential Synthesis (PASS).

FIG. 10 illustrates generally the method of this invention as applied to the assembly of peptides. With reference to FIG. 10, an N-protected amino acid monomer unit 77, is added to a peptide starting material 78 in solution in the presence of an activator. $R^6$ is a standard carboxy blocking group, a soluble polymer or a diagnostic detector. The N-terminal protecting group A is derivatized with a moiety X, designed to selectively and covalently react with group Y on resin 80. Reaction of 77 with peptide starting material 78, bearing a free N-terminal amino group, by standard coupling methods results in formation of the extended peptide product 79, now carrying the N-terminal protecting group. In addition, the reaction mixture contains the unreacted peptide starting material 78, as well as excess N-protected amino acid monomer 77 and coupling reagents. The peptide product 79, along with the unreacted monomer 77 are selectively captured onto a resin by reaction of group X with substituent Y on the resin to form the solid-support bound products 81 and 82. Release of 81 and 82 from the resin produces the N-deprotected peptide product 83, together with N-deprotected amino acid monomer. The latter, being a free amino acid most likely in betaine form, is easily removed by either precipitation, extraction, or membrane filtration. Alternatively, the amino acid monomer 77 may be removed by these techniques prior to capture of the product on the resin. The extended, deprotected peptide product 83 is then ready to undergo another addition cycle to extend the peptide chain.

In batch mode production, the unreacted peptide starting material 78 (failure sequence) can be re-isolated and used in subsequent cycle at the appropriate monomer addition step. This allows maximal efficiency of amino acid monomer conversion into productive product.

The N-terminal protecting group X-A is designed such that its chemical composition and the X-Y capture reaction are compatible with conventional peptide synthesis steps. Group A can be selected from any of the N-protecting groups known to those of ordinary skill in the art, (see. e.g., Bodansky (1984) in *Principles of Peptide Synthesis* (Springer Berlag, Berlin)), including but not limited to urethanes, such as fmoc and Boc, benzyl groups, acyl groups, or triphenylmethyl groups. The substituent X is designed to react with substituent Y on the resin with high selectivity. It is selected from groups such as dienes, in particular 3,5-hexadienoxy or sorbic amide, dienophiles, in particular maleimide, alkynes, silylether protected diols and disulfides. The corresponding substituent Y is chosen to be a selective covalent reaction partner for substituent X, such as a dienophile, diene, mercaptane, or borate.

In addition to serving as an anchor for selective product capture at each monomer addition step, the introduction of amino acid monomers carrying an N-terminal X-A protecting group at selected addition steps or at the final step of peptide preparation serves to affinity purify the product prior to final deprotection via capture on a Y-derivatized resin. This capture dramatically increases the efficiency of segment condensation and subsequent purification. With capture of the N-terminal segment on the resin, its C-terminal protecting group is removed and washed away without requiring laborious and yield-reducing work-up. The now free C-terminal carboxyl group is activated by a standard method and coupled to the C-terminal segment, bearing a free N-terminal amino group. After successful segment condensation, the reagents are washed away, the product peptide is released from the resin by selective breaking of the N-A bond by standard methods to yield essentially pure, side chain protected peptide.

Example 17 illustrates the preparation and use of N-2,7-di(3,5-hexadienoxyacetyl)fmoc protected amino acid monomers for peptide synthesis by PASS.

Example 18 illustrates the preparation and use of 2,7-di (maleimido)fluorene-9-methylchloroformate for peptide synthesis by PASS.

Example 19 illustrates peptide assembly using hexadienoxy-Boc protected amino acids by PASS.

Example 20 illustrates the preparation of peptide nucleic acids by PASS.

The following examples are provided for illustrative purposes only and are not intended to limit the scope of the invention.

EXAMPLE 1

Preparation of N-4-benzoyl-3'-(5'-tert-butyldimethylsilyl-3'-(2-cyanophosphoryl) thymidyl)-2'-fluorocytidine (16) (Scheme 4)

Figure 2:
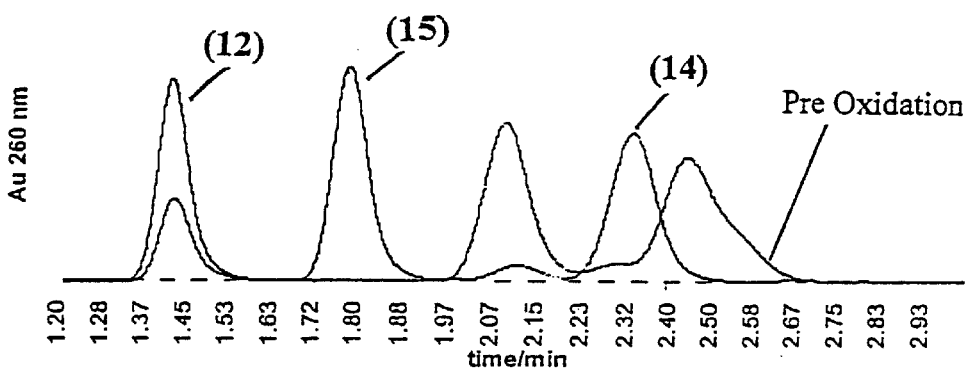
FIG. 2 illustrates the reverse phase HPLC trace of the phosphoramidite coupling reaction set forth in Example 1 after oxidation. The post oxidation trace has been superimposed on the preoxidation trace of FIG. 1.

5'-tert-butyldimethylsilylthymidine 12 (5'-TBDMS-thymidine) (0.15 g, 0.42 mmol) was dissolved in dry acetonitrile (10 mL) under an argon atmosphere. Cytidine amidite 13 was added (0.43 g, 0.50 mmol) followed by tetrazole (6.5 mL, 0.45 M in acetonitrile). After 15 minutes reverse phase HPLC analysis (C18, 4.6×100 mm, Buffer A: 100 mM triethylammonium acetate pH 7.5, Buffer B: acetonitrile, 0 to 80% B over 2.5 minutes) of the reaction mixture showed the presence of dimer (2.4 minutes) as well as unreacted thymidine 12 (1.4 minutes) and hydrolyzed amidite monomer (2.1 minutes) (FIG. 1). The reaction mixture was oxidized in situ (10 mL, 0.2 M iodine in water/pyridine). HPLC analysis after oxidation reveals the presence of pyridine (0.9 minutes), unreacted thymidine 12 (1.4 minutes), oxidized amidite monomer 15 (1.8 minutes), and oxidized dimer 14 (2.3 minutes) (FIG. 2).

After oxidation the reaction mixture was passed with acetonitrile through a bed of DEAE Sephadex® pre-equilibrated with acetonitrile. HPLC analysis of the filtrate indicates retention of the oxidized amidite monomer 15 as shown in FIG. 3. The filtrate was concentrated under reduced pressure and the solid was re-dissolved in 60% acetonitrile/water and loaded onto a C18 chamber pre-equilibrated with 70% water/acetonitrile. The chamber was washed with 70% water/acetonitrile followed by 50% water/acetonitrile to fully elute the unreacted thymidine 12. The chamber was then washed with water and treated with 80% acetic acid/water to effect detritylation. Following detritylation the chamber was washed with 50% acetonitrile/water to elute the final product 16 (m/e 922, product 16 plus triethylamine). HPLC analysis shows elution of the detritylated species 16 at 1.7 minutes (FIG. 4). ESMS (Electrospray Mass Spectrometry) of 16: Calcd 820.27 (M+); Found 922.2 (M+H+TEA). $^{31}$P NMR (121 MHz, CDCl$_3$, H$_3$PO$_4$ external standard) δ −0.73, −1.93. The trityl species was retained on the chamber.

EXAMPLE 2

Preparation of a H-phosphonate thymidine trimer (T-T-[3',3']-T) (20)

Assembly of a H-phosphonate thymidine trimer bearing a 3',3'-internucleotidic linkage at the 3'-terminus was synthesized as outlined in Scheme 5.

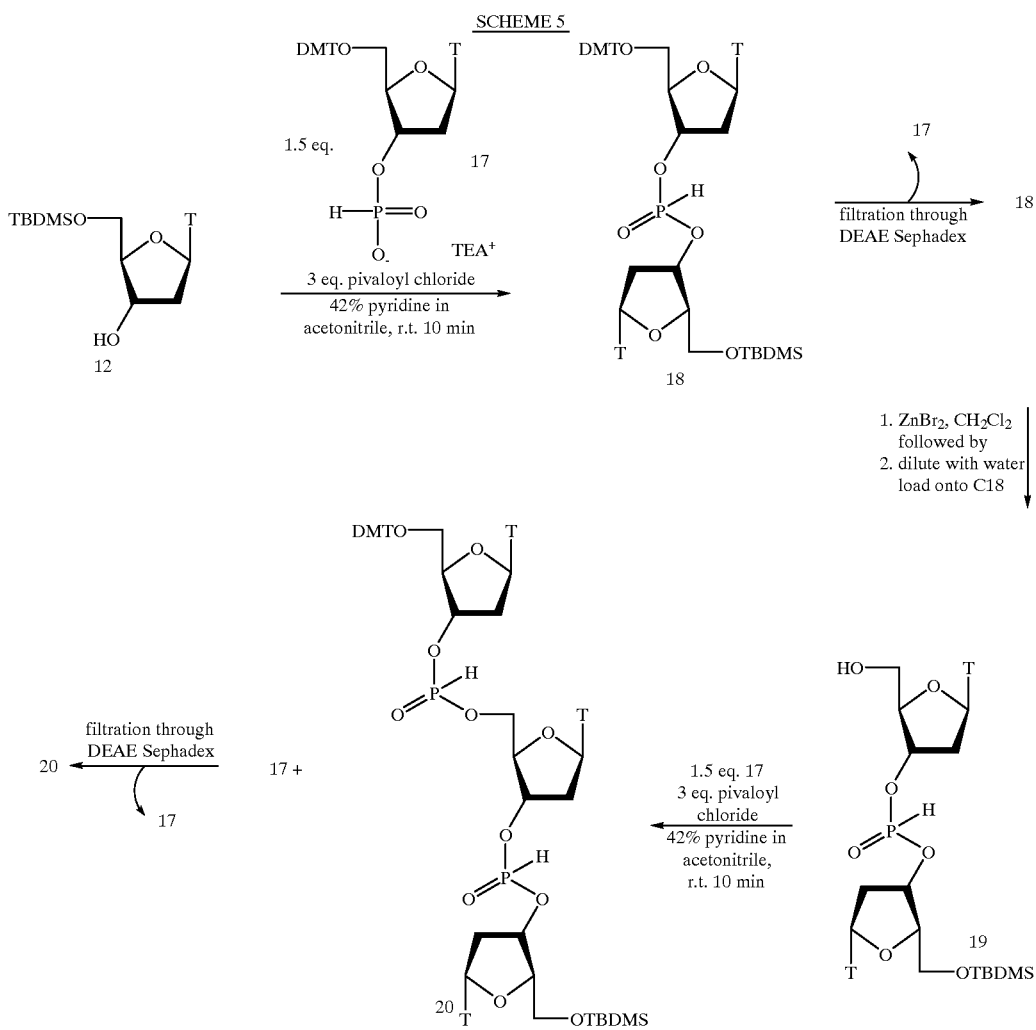

SCHEME 5

Coupling of 12 to 5'-dimethoxytritylthymidine 3'-H-phosphonate 17

To a solution of 17 (0.75 g, 1.05 mmol) in 1:1 acetonitrile:pyridine (42 mL) under argon was added 12 (0.25 g, 0.7 mmol), followed by a solution of pivaloyl chloride (0.26 mL, 2.1 mmol) in 95:5 acetonitrile:pyridine (8.4 mL). The reaction was stirred for 10 minutes, at which time reverse phase HPLC analysis showed complete conversion of 12 to dimer 18. The mixture was then concentrated in vacuo, dissolved in CH$_2$Cl$_2$, and extracted with 0.05 M triethylammonium bicarbonate. The methylene chloride layer was applied to a plug of DEAE Sephadex® on a Buechner funnel. Reverse phase HPLC analysis of the filtrate showed complete removal of the unreacted monomer 17. Dimer 18 was isolated in quantitative yield, by evaporation of the filtrate and its structure was confirmed by NMR and ESMS analysis. Unreacted monomer 17 was recovered from the DEAE Sephadex® plug by washing with 1 M triethylammonium bicarbonate. ESMS of 18: Calcd 946.4 (M+); Found 946.3. $^1$H NMR (300 MHz, CD$_3$CN) δ 9.21 (s, 2H), 7.45–7.24 (m, 11H), 6.94 (d, 1H, J=717.2 Hz), 6.89–6.85 (m, 4H), 6.31–6.19 (m, 2H), 5.22–5.19 (m, 1H), 5.05–5.00 (m, 1H), 4.22–4.19 (m, 1H), 4.11–4.10 (m, 1H), 3.81–3.80 (m, 2H), 3.75 (s, 6H), 3.36–3.35 (m, 2H), 2.52–2.17 (m, 4H), 1.83 (s, 3H), 1.47 (s, 3H), 0.91 (s, 9H), 0.10 (s, 6H). $^{31}$P NMR (121 MHz, CD$_3$CN) δ 14.03 (d), 13.88 (d).

Detritylation of dimer 18

Dimer 18 (0.85 g, 0.9 mmol) was dissolved in methylene chloride saturated with ZnBr$_2$ (10 mL, approximately 0.1 M ZnBr$_2$). After 15 minutes reverse phase HPLC analysis showed complete detritylation. The reaction was quenched with an equal volume of 1 M ammonium acetate. The organic layer was concentrated, the residue dissolved in 1:1 acetonitrile:water and passed over a C18 plug on a Buechner funnel. Evaporation of the filtrate gave 0.29 g (50 % yield) of pure dimer 19. ESMS of 19: Calcd 644.2 (M+); Found 645.3. $^1$H NMR (300 MHz, CDCl$_3$) δ 10.0, 9.85, 9.55, 9.45 (4s, 2H), 7.59–7.45 (m, 2H), 7.01 (d, 1H, J=712.3 Hz), 6.39–6.19 (m, 2H), 5.35–5.23 (m, 1H), 5.14–5.03 (m, 1H), 4.31–4.22 (m, 2H), 3.88–3.79 (m, 4H), 2.67–2.48 (m, 3H), 2.21–2.12 (m, 1H), 1.89–1.88 (2 bs, 6H), 0.90 (s, 9H), 0.11 (s, 6H). $^{31}$P NMR (121 MHz, CDCl$_3$)δ 8.45 (d), 8.30 (d).

Preparation of Trimer 20

To a solution of dimer 19 (0.25 g, 0.39 mmol) in 1:1 pyridine acetonitrile (23 mL) was added 17 (0.41 g, 0.58 mnmol), followed by a solution of pivaloyl chloride (0.14 mL, 1.16 mmol) in 95:5 acetonitrile:pyridine (4.5 mL). The reaction was stirred under an argon atmosphere for 10 minutes, at which point HPLC analysis indicated complete conversion of dimer 19 to trimer 20. The mixture was evaporated to dryness, dissolved in CH$_2$C$_2$, washed with 0.05 M triethylammonium bicarbonate, and the organic layer was applied to a DEAE Sephadex® plug on a Buechner funnel. The filtrate was evaporated to give 20 in quantitative yield. ESMS of 20: Calcd 1234.4 (M+); Found 933.5 (M+H+with loss of DMT). $^1$H NMR (300 MHz, CD$_3$CN) δ 9.34–9.27 (m, 2H), 8.58–8.56 (m, 2H), 8.18–8.11 (m, 1H), 7.76–7.70 (m, 1H), 7.43–7.41 (m, 4H), 7.35–7.23 (m, 13H), 6.88–6.84 (m, 4H), 6.26–6.15 (m, 3H), 5.78–5.71 (m, 1H), 5.22–5.20 (m, 1H) 5.11–5.05 (m, 2H), 4.29–4.26 (m, 2H) 4.24–4.19 (m, 2H), 3.85–3.84 (m, 2H), 3.76 (s, 6H), 3.74–3.72 (m, 1H), 3.38–3.28 (m, 2H), 2.52–2.20 (m, 6H), 1.82 (s, 3H), 1.78 (s, 3H), 1.47–1.44 (m, 3H), 0.90 (s, 9H), 0.11 (s, 6H). $^{31}$P NMR (121 MHz, CD$_3$CN) δ 15.86 (s), 15.08 (s), 14.36 (s).

EXAMPLE 3

Preparation of 5'-O-(4,4'-dioctadecyltriphenylmethyl)thymidine -3'-O-(N,N-diisopropyl-2-cyanoethylphosphoramidite) (26)

Assembly of a phosphoramidite monomer containing 4,4'-dioctadecyltriphenylmethanol (DOT) as the 5'-protecting group (D-E) is illustrated in Scheme 6.

SCHEME 6

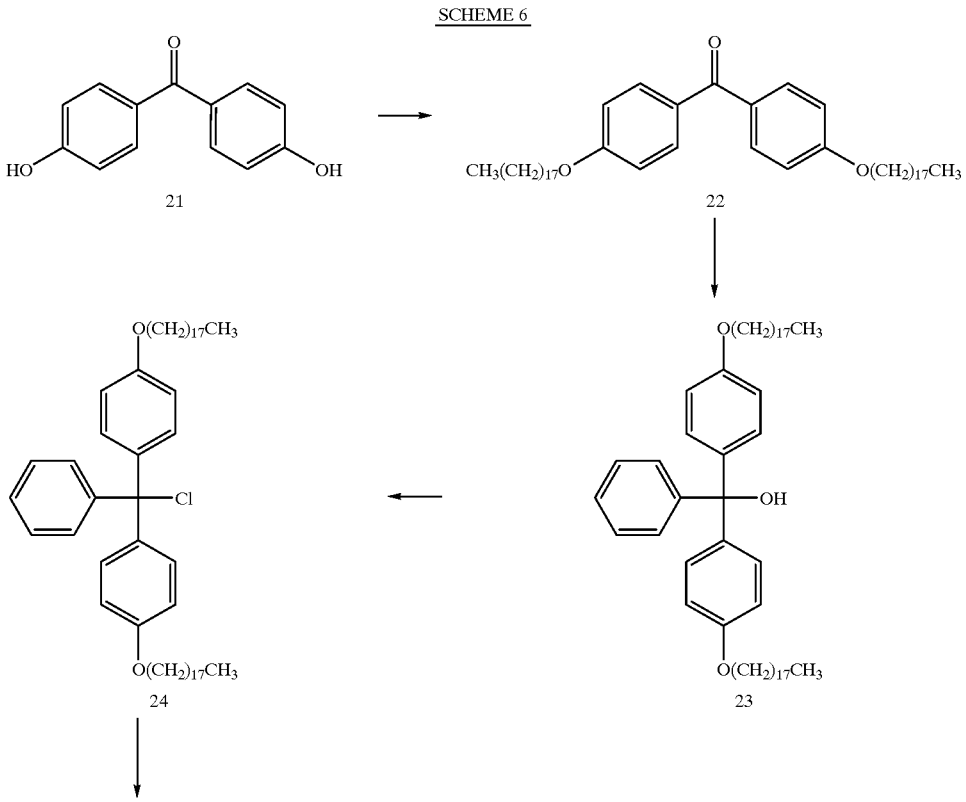

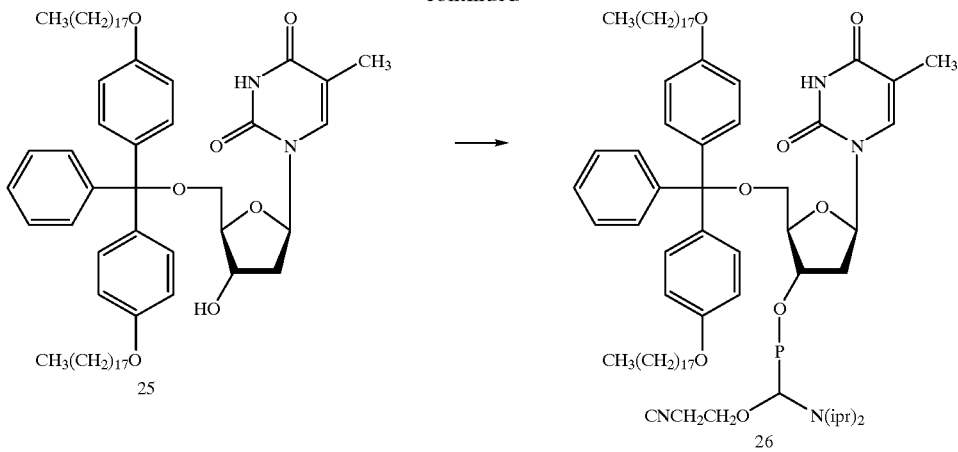

4,4'-Dioctadecyloxy-benzophenone (22)

Sodium metal (0.46 g, 20 mmol) was dissolved in ethanol (50 mL) and 4,4'-dihydroxybenzophenone (1.0 g, 4.67 mmol) was added followed by 1-bromooctadecane (7.8 g, 23.4 mmol) and a catalytic amount of sodium iodide (approximately 30 mg) and the reaction mixture was refluxed for 48 hours. The resulting suspension was cooled and filtered. The solid was washed with dichloromethane followed by hexane and the white solid was dried to afford compound 22 (2.85 g, 84.8% yield). $^1$H NMR (300 MHz, pyridine-$d_5$) δ 7.95 (d, J=8.7 Hz, 4H, aryl), 7.09 (d, J=8.7 Hz, 4H, aryl), 4.05 (t, J=6.6 Hz, 4H, 2×OCH$_2$), 1.80 (tt, J=6.6 and 7.5 Hz, 4H), 1.48 (m, 4H), 1.33 (brS, 60H), 0.87 (t, J=6.6 Hz, 6H, 2×CH$_3$).

4,4'-Dioctadecyltriphenylmethanol (23)

To a suspension of benzophenone 22 (0.3 g, 0.42 mmol) in anhydrous THF (4 mL) was added phenylmagnesium bromide (0.55 mL, 1.0 M solution in THF, 0.55 mmol) and the reaction was refluxed for 3 hours. An additional amount of phenylmagnesium bromide (0.2 mL) was added and the heating was continued for 0.5 hours at which time all of the starting material had dissolved. The reaction was then cooled and 0.5 M HCl was added. The suspension was filtered and the solid washed with water (3×), hexane (2×) and dichloromethane (2×). The organic washes were pooled, dried (MgSO$_4$) and evaporated to afford 23 (0.21 g, 63.6% yield) as a white solid. $^1$H NMR (300 MHz, pyridine-$d_5$) δ 8.13 (brS, 1H, aryl), 7.81 (d, J=7.1 Hz, 2H), 7.7 (d, J=8.8 Hz, 4H), 7.42 ( t, J=7.7 Hz, 2H), 7.34 (t, J=7.1 Hz, 1H), 7.07 (d, J=8.9 Hz, 4H), 3.98 (t, J=6.4 Hz, 4H), 1.77 (tt, J=7.9 and 6.5 Hz, 4H), 1.45 (m, 4H), 1.3 (brS, 60H), 0.87 (t, J=6.9 Hz, 6H).

5'-O-(4,4'-Dioctadecyltriphenylmethyl)thymidine (25)

Compound 23 (2.1 g, 2.63 mmol) was coevaporated twice with toluene then dissolved in toluene (30 mL). Acetyl chloride (11 mL, 154.7 mmol) was added and the reaction was refluxed for 3 hours and then evaporated. The residue was coevaporated twice with toluene to afford crude 24. To 24 was added pyridine (30 mL), DMAP (25 mg) and thymidine (0.45 g, 1.86 mmol) and the reaction was stirred at room temperature overnight. The solvent was evaporated under reduced pressure and the residue was taken up in dichloromethane and washed with 5% sodium bicarbonate. The organic phase was dried (MgSO$_4$) and evaporated and the residue was purified on silica gel (ethyl acetate/2% triethylamine) to afford after evaporation of the appropriate fractions compound 25 (DOT thymidine) (1.6 g, 84% yield) as pale yellow solid. $^1$H NMR (300 MHz, CDCl$_3$) δ 8.44 (brS, 1H, NH), 7.60 (s, 1H, H-6), 7.41–7.20 and 6.82 (m, 13H, DOT), 6.42 (t, J=6.1 Hz, 1H, H-1'), 4.57 (m, 1H, H-3'), 4.05 (m, 1H, H-4'), 3.92 (t, J=6.5 Hz, 4H, 2×OCH$_3$), 3.47 and 3.37 (ABX, 2H, H-5'), 2.38 (m, 2H, H-2'), 2.22 (m, 1H, 3'-OH), 1.75 (m, 4H, DOT), 1.46 ( m, 7H, 5-CH$_3$, DOT), 1.25 (brS, 60H, DOT), 0.87 (t, 6H, 2×CH$_3$).

5'-O-(4,4'-Dioctadecyltriphenylmethyl)thymidine-3'—O—(N,N-diisopropyl-2-cyanoethylphosphoramidite (26)

DOT thymidine 25 was dissolved in dichloromethane (5 mL) and diisopropylethylamine (0.3 mL, 1.75 mmol) and 2-cyanoethyl N,N-diisopropylchlorophosphoramidite (0.15 mL, 0.63 mmol) was added with ice bath cooling. The ice bath was removed and the reaction was stirred at room temperature for 4 hours at which point additional 2-cyanoethyl N,N-diisopropylchlorophosphoramidite (0.1 mL) was added and the reaction was stirred for 16 hours at room temperature. The reaction solution was diluted with dichloromethane and washed with 5% sodium bicarbonate, the organic phase was dried (MgSO$_4$) and evaporated. The residue was purified on silica eluting first with hexanes, followed by 20% ethyl acetate/hexanes all containing 2% triethylamine to afford 26 as resolved diastereomers (fast 0.1 g, slow 0.18 g, 46.7 % yield). 26a (fast diastereomer) $^1$H NMR (300 MHz, CDCl$_3$) δ 8.15 (br, 1H, NH), 7.91 (s, 1H, H-6), 7.63, 7.38–7.21, 6.82 (m, 13H, aryl), 6.39 (t, J=7.4 Hz, H-1'), 4.67 (m, 1H, H-3'), 4.18 (m, 1H, H-4'), 3.92 (t, J=6.5 Hz, 2×OCH$_3$), 3.63 (m, 4H), 3.51 and 3.33 (ABX, 2H, H-5'), 2.42 and 2.26 (m, 4H, H-2', CH$_2$CN), 1.73 (m, 4H), 1.41 (m, 4H), 1.25 (s, 60H), 1.16 (dd, J=2.7, 6.9 Hz, 12H), 0.87 (t, J=6.9 Hz, 6H). $^{31}$P NMR (121 MHz, CDCl$_3$) δ 150.64. 26b (slower diastereomer) $^1$H NMR (300 MHz, CDCl$_3$) δ 8.25 (br, 1H, NH), 7.91 (s, 1H, H-5), 7.41 and 7.31–7.20 and 6.81 (m, 13H, aryl), 6.42 (dd, J=8 Hz, H-1'), 4.67 (m, 1H, H-3'), 4.14 (m, 1H, H-4'), 3.92 (t, J=6.5 Hz, 4H, 2×OCH$_2$), 3.82 and 3.76 (m, 2H), 3.54 (m, 2H), 3.47 and 3.31 (ABX, 2H, H-5'), 2.62 (t, J=6.3 Hz, 2H, CH$_2$CN), 2.54 and 2.34 (m, 2H, H-2'), 1.76 (m, 4H), 1.25 (m, 60H), 1.16 and 1.05 (d, J=6.9 Hz, 12H, isopropyl CH$_3$), 0.87 (t, J=6.6 Hz, 6H). $^{31}$P NMR (121 MHz, CDCl$_3$) δ 150.23.

EXAMPLE 4

Resolution of alkyl substituted trityl groups on reverse phase resin

The alcohols of 4,4'-dioctadecyltriphenylmethanol (DOT), 4-decyloxy-4'-methoxytritanol, and dimethoxytritanol (DMT) were spotted onto a C18 reverse phase TLC plate and the plate was developed in three different solvents (Table 1). As can be seen in Table 1, there is a strong interaction of the DOT group with the C18 resin in organic solvents, such as methanol ($R_f$=0) and acetonitrile ($R_f$=0). This interaction enables the one-step separation of the coupled product from starting material based upon the affinity or interaction of the trityl protecting group for C18 reverse phase resin.

EXAMPLE 5

Preparation of 5'-HO-T-T-A-C-T-[3',3'-]-T-3' PASS using hydrophobic affinity for product capture

Preparation of 5'-HO-T-[3',3']-T

5'-TBDPS-thymidine 12 (0.99 g, 2.07 mmol) was co-evaporated with dry methylene chloride and dissolved in 10 mL of dry methylene chloride. Thymidine amidite (2.0 g, 2.69 mmol) was added followed by tetrazole 0.5 M in acetonitrile (21 mL, 10.5 mmol) and the reaction was stirred under argon. After 90 minutes, a solution of iodine/water/pyridine (0.2 M) was added until the dark brown color persisted, followed by 5% NaHSO$_3$ until the color returned to yellow. The concentrated reaction was partitioned (CH$_2$Cl$_2$/water) and the organic layer was dried with MgSO$_4$ and evaporated to dryness. The solid residue was dissolved in methanol/minimal methylene chloride and pipetted onto a 75 g bed of DEAE Sephadex® equilibrated with water then methanol. The DEAE Sephadex® was washed with 300 mL methanol and the combined methanol washes were concentrated to afford 2.42 g of a white foam.
Detritylation: The white foam was dissolved in 50 mL of 3% DCA and stirred at room temperature for 35 minutes, and then poured over 80 mL of silica gel equilibrated with methylene chloride. The gel was washed with 150 mL of 3% DCA, followed by solutions from 100% methylene chloride through 6% methanol in methylene chloride. Appropriate fractions were combined and concentrated to give 1.58 g of detritylated dimer (5'-HO-T-[3',3']-T) in 90% yield for the two step process.

Preparation of the 5'-HO-C-T[3',3']-T

The 5'-HO-T-[3',3']-T dimer (1.47 g, 1.76 mmol) was dried under high vacuum overnight, and then co-evaporated with dry CH$_2$Cl$_2$ and dissolved in 8.5 mL of dry CH$_2$Cl$_2$. Cytidine amidite (1.90 g, 2.28 mmol) was added followed by tetrazole (0.5 M) in acetonitrile (17.6 mL, 8.78 mmol) and the reaction was stirred under argon. After 50 minutes, a 0.5 M iodine solution was added, followed by 5% NaHSO$_3$, changing the color from brown to yellow as described above. The concentrated reaction was partitioned (CH$_2$Cl$_2$/water) and the organic layer was dried (MgSO$_4$) and evaporated to dryness. The solid residue was dissolved in methanol/minimal methylene chloride and pipetted onto a 75 g bed of DEAE Sephadex® pre-equilibrated with water and then methanol. The DEAE Sephadex® was washed slowly with methylene chloride and methanol and the combined washes were concentrated to afford 2.53 g of a yellow foam.
Detritylation: The foam was stirred in 50 mL of 3% DCA at room temperature. After 2 hours, the reaction mixture was pipetted onto an 80 mL bed of silica gel pre-equilibrated with methylene chloride. The mixture was eluted with 3% DCA, followed by solutions from 100% CH$_2$Cl$_2$ through 6% methanol in CH$_2$Cl$_2$. The appropriate fractions were combined and concentrated to give 1.43 g of the detritylated trimer (5'-HO-C-T-[3',3']-T), 64% yield for the two step process.

Preparation of 5'-HO-A-C-T-[3',3']-T

The detritylated trimer 5'-HO-C-T-[3',3']-T (1.43 g, 1.1 mmol) was dried under high vacuum overnight, coevaporated with dry methylene chloride and dissolved in 6 mL of dry methylene chloride. Adenine amidite (1.24 g, 1.45 mmol) was added, followed by 0.5 M tetrazole in acetonitrile (11 mL, 5.57 mmol) and the reaction was stirred under argon. After approximately 60 minutes, a 0.5 M iodine solution was added until the dark color persisted. The mixture was then stirred for 1 hour and concentrated. The gum was partitioned (CH$_2$Cl$_2$/water) and the combined organic layer was dried (MgSO$_4$) and concentrated to yield 2.46 g of a yellow solid. The detritylation was carried out without DEAE Sephadex® purification.
Detritylation: The foam was stirred in 50 mL 3% DCA at room temperature, then pipetted onto a silica bed (approximately 120 mL) equilibrated with methylene chloride. The reaction mixture was eluted with 3% DCA then 100% methylene chloride through 10% methanol in methylene chloride. The appropriate fractions were combined and concentrated to give 1.41 g of the detritylated tetramer (5'-HO-A-C-T-[3',3']-T), 72% overall yield for the two step process.

Preparation of 5'-HO-T-A-C-T-[3',3']-T

The detritylated tetramer 5'-HO-A-C-T-[3',3']-T (1.41 g, 0.8 mmol) was dried on high vacuum, then co-evaporated with dry methylene chloride and dissolved in 4.5 mL dry methylene chloride. Thymidine amidite (0.78 g, 1.05 mmol) was added followed by tetrazole (0.5 M) in acetonitrile (8 mL, 4.02 mmol) and the reaction stirred under argon. After 2 hours, a 0.5 M iodine solution was added until the dark color persisted. The reaction was then concentrated and the gum was partitioned (CH$_2$Cl$_2$/water) and the combined organic layers were dried (MgSO$_4$) and concentrated to yield 2.1 g of a yellow foam, which was analyzed by mass spectrometry and reverse phase HPLC prior to elution through DEAE Sephadex®. Reverse phase HPLC analysis of the crude reaction mixture after oxidation showed the presence of pentamer, as well as, unreacted tetramer (failure sequence) and hydrolyzed amidite monomer. ESMS (M-1) 803.74×3.

The yellow foam was dissolved in minimal methylene chloride and loaded onto a DEAE Sephadex® bed equilibrated with water and then methanol. The Sephadex® was washed with methanol, methylene chloride and then acetonitrile. The appropriate fractions were combined and concentrated to give 1.48 g of material.
Detritylation: The material was stirred in 40 mL 3% DCA at room temperature, and then pipetted onto a silica bed equilibrated with methylene chloride. It was eluted with 3% DCA, followed by solutions of 100% methylene chloride through 20% methanol in methylene chloride. The appropriate fractions were combined and concentrated to give 0.98 g of the detritylated pentamer (5'-HO-T-A-C-T-[3',3']-T), 64% overall yield for the two-step process. The $^{31}$P NMR and its integration, are consistent with the product.

Preparation of 5'-HO-T-T-A-C-T-[3',3']-T

The detritylated pentamer 5'-HO-T-A-C-T-[3',3']-T (0.96 g, 0.46 mmol) was dried under high vacuum, then co-evaporated with dry methylene chloride and dissolved in 5 mL of dry methylene chloride. Thymidine amidite (0.44 g, 0.59 mmol) was added followed by tetrazole (0.5 M) in acetonitrile (4.5 mL, 2.27 mmol) and the reaction was stirred under argon. Since the solution was not homogenous, 2 mL of acetonitrile was added. After 2 hours, an additional 0.15 g of monomer was added and the reaction was stirred overnight. A 0.5 M iodine solution was added, followed by 5% $NaHSO_3$, changing the color from brown to yellow. The concentrated reaction was partitioned ($CH_2Cl_2$/water) and the organic layer was dried ($MgSO_4$) and concentrated to yield 1.61 g of a yellow solid which was analyzed by MS. ESMS (M-1) 1384.01×2.

The crude reaction mixture (1.48 g) was absorbed onto C18 resin and loaded onto a bed of C18 resin (approximately 125 g) which had been equilibrated with acetonitrile, followed by 70% water/acetonitrile. The resin was first washed with 1:1 water:acetonitrile to elute the monomer, followed by acetonitrile and methylene chloride to elute the hexamer. The appropriate fractions were combined and concentrated to give 0.83 g, (66% yield) of a solid.

Detritylation. The solid was stirred in 20 mL of 3% DCA at room temperature. Trihexylsilane (2 mL) was added and stirring was continued. Upon addition of hexane a solid formed which was washed with hexane/ether to give 0.5 g of pink solid. The $^{31}P$ NMR and its integration, are consistent with the product.

Dowex Cl-form can be used to remove residual DCA from a solid sample. For example, a T-A phosphoramidite dimer was found by NMR to contain approximately 1.2 equivalents of DCA following detritylation and hexane precipitation. A sample of this dimer (0.3 g) was dissolved in acetonitrile (5 mL) and loaded onto a column of Dowex Cl-form (15 g) which had been pre-equilibrated with acetonitrile. The liquid was eluted dropwise and the column was then washed with 35 mL of acetonitrile and concentrated to yield 0.26 g of a white foam. A sample checked by NMR shows approximately 95% reduction of acid.

EXAMPLE 6

Automation of PASS using hydrophobic affinity to capture the product

After the coupling reaction, e.g., the reaction of 12 with 17 in Example 2 (Scheme 5), the reaction mixture is pumped into extraction vessel 112, through inlet port 128 (FIG. 5). Triethylammonium bicarbonate buffer (TBK) (0.05 M) and $CH_2Cl_2$ are added to the extraction vessel through inlet port 130, and the mixture is stirred. The layers are allowed to separate. After separation, valve 120 opens and the methylene chloride layer passes through conductivity meter 136, and onto a DEAE Sephadex® plug 114. A rise in conductivity indicates that the $CH_2Cl_2$ has completely passed through the conductivity meter and the aqueous layer has now entered the meter. At this time, valve 120 automatically switches to divert the aqueous layer away from the DEAE Sephadex® plug. The organic layer is pushed through the DEAE Sephadex® plug with argon which enters the chamber through inlet port 140. The DEAE Sephadex® plug is then washed with $CH_2Cl_2$, which is added through inlet port 142, controlled by valve 122. The $CH_2Cl_2$ effluent, which contains the oligonucleotide product and unreacted oligonucleotide starting material (failure sequence), is collected through outlet port 144, controlled by valve 124. Upon complete elution of $CH_2Cl_2$, the unreacted phosphoramidite monomer, which has been retained on the Sephadex® plug, is eluted with the 1 M TBK. The Sephadex® plug is then re-equilibrated with $CH_2Cl_2$.

The $CH_2Cl_2$ eluent, is then passed through a reverse phase resin to separate the coupled product from the failure sequence. The coupled product, which has a DMT group attached to its 5'-end, is retained on the resin, and the failure sequence is eluted from the chamber. The resin is then washed with, acidic dichloroacetic acid (3% in $CH_2Cl_2$), which cleaves the DMT protecting group and releases the coupled product from the chamber. The coupled product is eluted into a pH buffered solution to prevent decomposition due to excessive exposure to acid. The eluent is concentrated and the coupled product used as the starting material in the next reaction cycle.

EXAMPLE 7

Preparation of a 3'-PEG anchored 15mer DNA by solution phase synthesis

An oligonucleotide of sequence 5'-CTAAACGTAATGG-[3',3']-T-T-T-3'(SEQ ID NO:1) was prepared by liquid phase synthesis, using polyethylene glycol (PEG) of molecular weight 20,000 as the 3'-terminal modification. Polyethylene glycol allows facile precipitation of the growing oligonucleotide chain during the individual steps. This example outlines the basic steps required for solution phase synthesis without the incorporation of the capture of the oligonucleotide coupling product onto a resin as in a typical PASS cycle. Thus, this example demonstrates the impact on efficiency and product purity, that product capture provides as envisioned in PASS. With such product capture at each monomer addition cycle, the cumbersome precipitations from diethyl ether are no longer necessary. In addition, because failure sequences are removed at each monomer addition cycle, the anion exchange chromatogram of the product obtained by PASS is expected to only show a single product peak, rather than the multiple peaks seen in FIG. 6.

This example provides the general procedures followed for each monomer addition cycle for the preparation of a 3'-PEG anchored oligonucleotide by solution phase synthesis without the incorporation of product capture as a means to separate product from failure sequence. All of the following reactions were performed in a one-neck flask with a self-sealing septum at room temperature. Disposable plastic syringes were used.

Detritylation: 5'-DMT-nucleoside 3'-O-PEG (5.0 g) (20 k, loading: 45 μmol/g) was dissolved in 50 mL of a mixture of dichloroacetic acid (DCA) and trihexylsilane (6.4 mL, 80 equivalents) in $CH_2Cl_2$. After 9 minutes the detritylated 5'-HO-nucleoside 3'-O-PEG was precipitated with ether (2×), washed, filtered and dried under vacuum.

Coupling reaction: The 5'-HO-nucleoside 3'-O-PEG was coevaporated 3 times with 20 mL of anhydrous acetonitrile and dried under high vacuum for 30 minutes. The flask was flushed with argon and closed to the outer atmosphere. Through the septa was injected: 50 mL of anhydrous acetonitrile to dissolve the 5'-HO-nucleoside 3'-O-PEG, 4.5 mL (0.1 M, 2.0 equivalents) of amidite in anhydrous acetonitrile and 1.4 mL (1.0 M, 6.0 equivalents) of DCI in acetonitrile. The solution was stirred under argon for 25 minutes, then precipitated with ether and dried by coevaporation with 20 mL of anhydrous acetonitrile.

Oxidation: The precipitate was dissolved in 50 mL of anhydrous acetonitrile, and 8 mL (0.1 M) of iodobenzene diacetate in acetonitrile was injected and the reaction mixture was stirred for 8 minutes.

Capping reaction: Acetic anhydride (6 mL), 2,6-lutidine (6 mL) and N-methylimidazole (6 mL) were simultaneously injected to the above solution and the reaction mixture was stirred for another 5 minutes. The capped oligonucleotide-PEG polymer was precipitated from ether as described above in the detritylation procedure.

Crystallization: The capped oligonucleotide-PEG polymer was purified by crystallization from 500 mL of absolute ethanol (100 mL/g) at 60° C.

Figure 6:
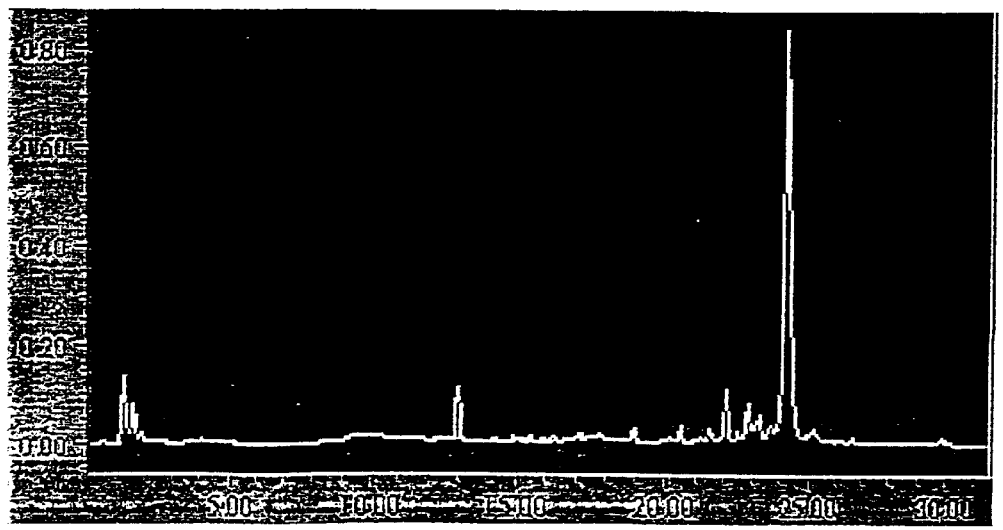
FIG. 6 illustrates the anion exchange HPLC trace of the 15 base oligonucleotide prepared in Example 7 using 3'-PEG anchored solution phase synthesis.

The monomer addition cycle protocol is summarized in Table 2. The stepwise coupling efficiency for the preparation of the 3'-terminal 10 base fragment (10mer) (CGTAATGG-[3',3']-T-T) of oligonucleotide (SEQ ID NO:2), is shown in Table 3. The anion exchange HPLC chromatogram of the crude 15mer (5'-CTAAACGTAATGG-[3',3']-T-T-3' (SEQ ID NO:1) after cleavage from the PEG and deprotection is shown in FIG. 6.

EXAMPLE 8

Preparation of diene modified trityl alcohols

Example 8 (Schemes 7 and 8) describes the synthesis of various diene modified trityl alcohols including a 5'-O-(4, 4'-di-3,5-hexadienoxytrityl) thymidine 3'-phosphoramidite monomer 32.

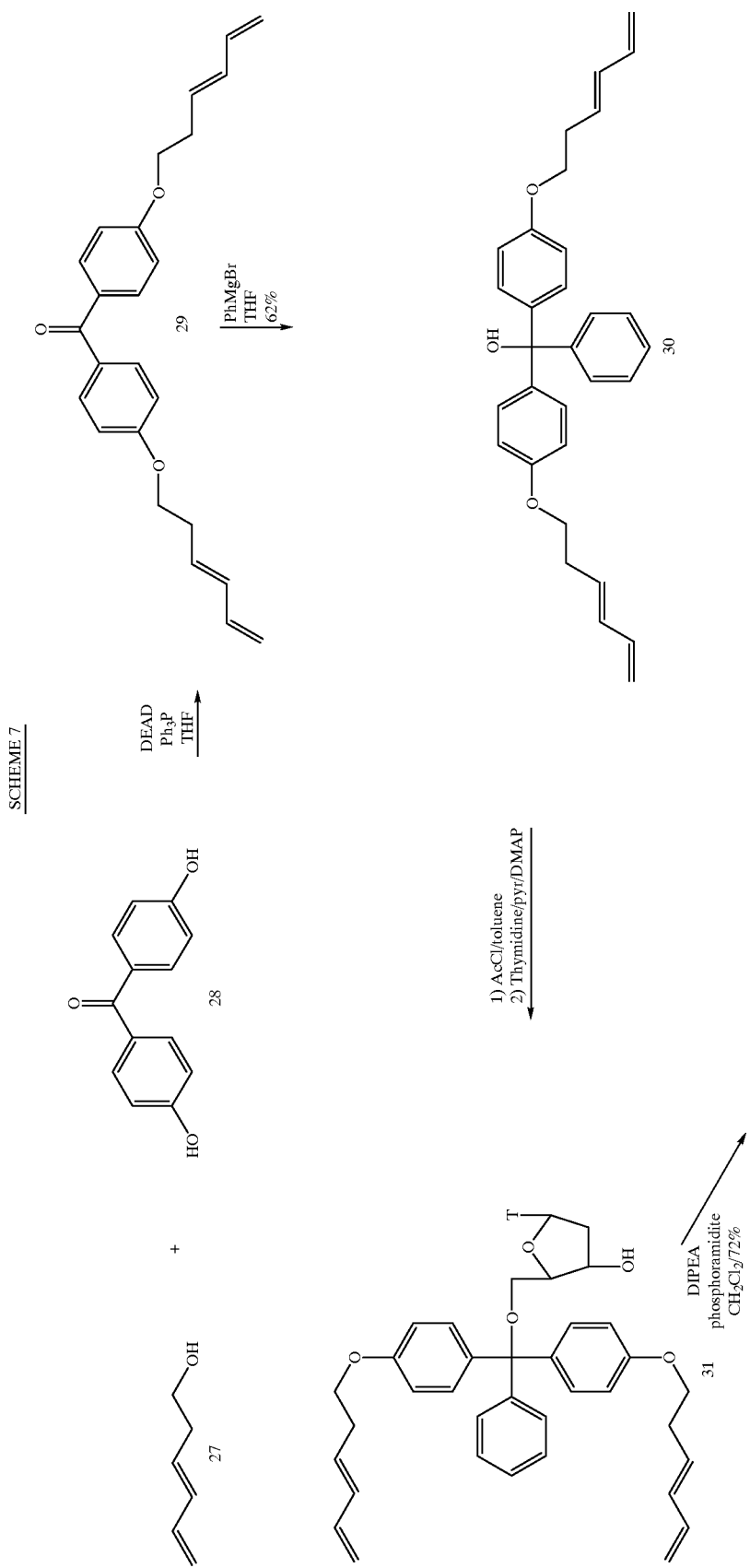

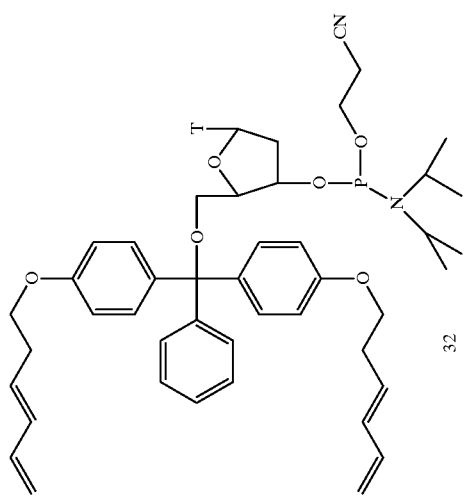

Preparation of 4,4'-di-3,5-hexadienoxybenzophenone (29)

To a solution of 3,5-hexadienol (27) (13.7 g, 140 mmol) (Martin et al. (1980) J. Am. Chem Soc. 102:5274–5279) in anhydrous THF (335 mL) was added 4,4'-dihydroxybenzophenone (28) (10.0 g, 46.7 mmol) and triphenylphosphine (36.7 g, 140 mmol) followed by the slow addition of diethylazodicarbonate (DEAD) (22.0 mL, 140 mmol). The reaction mixture was stirred under argon overnight and then evaporated to dryness under vacuum. A precipitation from dichloromethane-hexane was carried out to remove residual reagents. The filtrate was concentrated in vacuo and purified by column chromatography (silica gel; hexanes/$CH_2Cl_2$, 3/2) to afford an impure product which was triturated ($Et_2O$/hexane, 1/1) to give 7.12 grams of compound 29. Further purification of the filtrate by column chromatography (silica gel; hexane/$CH_2Cl_2$, 3/2) afforded an additional 5.96 grams of 29 to give a total of 13.08 g (75%) of compound 29 as a white solid. $^1$H NMR (300 MHz, DMSO-$d_6$) δ 2.50–2.64 (m, 4H), 4.16 (t, J=6.5 Hz, 4H), 5.05 (d, J=10.1 Hz, 2H), 5.18 (d, J=15.7 Hz, 2H), 5.77–5.92 (m, 2H), 6.17–6.47 (m, 4H), 7.10 (d, J=8.6 Hz, 4H), 7.72 (d, J=8.7 Hz, 4H).

Preparation of 4,4'-di-3,5-hexadienoxytrityl alcohol (30)

Compound 29 (5.96 g, 15.91 mmol) was dissolved in anhydrous THF (133 mL) with slight heating. Phenylmagnesium bromide (32 mL of a 1.0 M solution in THF, 32 mmol) was added to the solution and the mixture was stirred at room temperature under argon for 5 hours and evaporated to dryness under vacuum. The residue was redissolved in dichloromethane and washed with a saturated solution of ammonium chloride, followed by water. The organic phase was dried ($MgSO_4$), concentrated in vacuo, and purified by column chromatography (silica gel; hexane/$CH_2Cl_2$, 1/9) to yield 4.45 grams (62%) of compound 30 as a yellow oil. $^1$H NMR (300 MHz, DMSO-$d_6$)δ 2.45–2.56 (m, 4H), 3.98 (t, J=6.6 Hz, 4H), 5.01 (dd, J=1.5, 9.9 Hz, 2H), 5.14 (dd, J=1.5, 16.5 Hz, 2H), 5.73–5.87 (m, 2H), 6.12–6.41 (m, 4H), 6.25 (s, 1H), 6.84 (d, J=6.9 Hz, 4H), 7.06 (d, J=7.8 Hz, 4H), 7.15–7.33 (m, 5H).

Preparation of 5'-O-(4,4'-di-3,5-hexadienoxytrityl) thymidine (31)

Compound 30 (3.5 grams, 7.73 mmol) was coevaporated with toluene (2×) and then dissolved in anhydrous toluene (85 mL). Acetyl chloride (33 mL, 464 mmol) was added to the solution and the reaction mixture was heated to reflux and stirred under argon. After 4 hours the reaction mixture was concentrated in vacuo and the crude product was coevaporated with pyridine and then dissolved in anhydrous pyridine (42 mL). Thymidine (1.5 grams, 6.18 mmol), which had been coevaporated with pyridine and dissolved in anhydrous pyridine (42 mL), was then added to the solution containing the crude product. A catalytic amount of dimethylaminopyrimidine (DMAP) was added and the reaction mixture was stirred under argon overnight and the solvent was evaporated. The residue was redissolved in dichloromethane and washed with a 5% aqueous solution of sodium bicarbonate followed by water. The organic phase was dried ($MgSO_4$), evaporated and purified by column chromatography (silica gel; EtOAc/hexane, 1/1) to afford 3.53 grams (84%) of compound 31 as an off-white solid. $^1$H NMR (300 MHz, CDCl$_3$) δ 1.47 (s, 3H), 2.22–2.46 (m, 2H), 2.50–2.63 (m, 4H), 3.35–3.58 (m, 2H), 3.85–4.09 (m, 5H), 4.51–4.60 (m, 1H), 5.02 (dd, J=1.5, 10.4 Hz, 2H), 5.14 (dd, J=1.5, 17.3 Hz, 2H), 5.68–5.83 (m, 2H), 6.12–6.45 (m, 5H), 6.82 (d, J=9.0 Hz, 4H), 7.18–7.46 (m, 9H), 7.58 (s, 1H), 8.44 (s, 1H); Anal. Calcd for $C_{41}H_{44}N_2O_7 \cdot 2H_2O$ (712.8384): C, 69.08; H, 6.79; H, 3.93. Found: C, 69.34; H, 6.44; N, 3.91.

Preparation of 5'-O-(4,4'-di-3,5-hexadienoxytrityl) thymidine 3'-phosphoramidite (32)

Compound 31 (3.0 grams, 4.43 mmol) was dissolved in anhydrous dichloromethane and diisopropylethylamine (2.7 mL; 15.5 mmol) was added. The solution was cooled to 0° C. and 2-cyanoethyl-N,N-diisopropylchlorophosphoramidite (2.0 mL, 8.86 mmol) was added. The reaction mixture was allowed to warm to room temperature with stirring under argon. After 4 hours the solution was diluted with dichloromethane and washed with a 5% aqueous solution of sodium bicarbonate (2×). The organic phase was dried ($MgSO_4$), concentrated in vacuo, and purified by column chromatography (silica gel; EtOAc/hexane, 3/7) to afford 2.8 grams (72%) of compound 32 as a fluffy white solid. $^1$H NMR (300 MHz, CDCl$_3$) δ 1.01–1.20 (m, 12H), 1.41 (s, 3H), 2.25–2.67 (m, 8H), 3.26–4.22 (m, 11H), 4.60–4.65 (m, 1H), 5.02 (dd, J=1.5, 10.4 Hz, 2H), 5.14 (dd, J=1.5, 17.3 Hz, 2H), 5.69–5.84 (m, 2H), 6.11–6.48 (m, 5H), 6.82 (dd, J=3.2, 8.9 Hz, 4H), 7.16–7.43 (m, 9H), 7.62 (d, J=15.2 Hz, 1H), 8.05 (bs, 1H); $^{31}$P NMR (300 MHz, DMSO-$d_6$) 152.9, 152.4; Anal. Calcd for $C_{50}H_{61}N_4O_8P_1$(877.0276): C, 68.48; H, 7.01; N, 6.39. Found: C, 68.48; H, 7.22; N, 6.33.

SCHEME 8

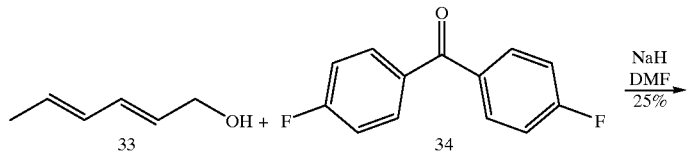

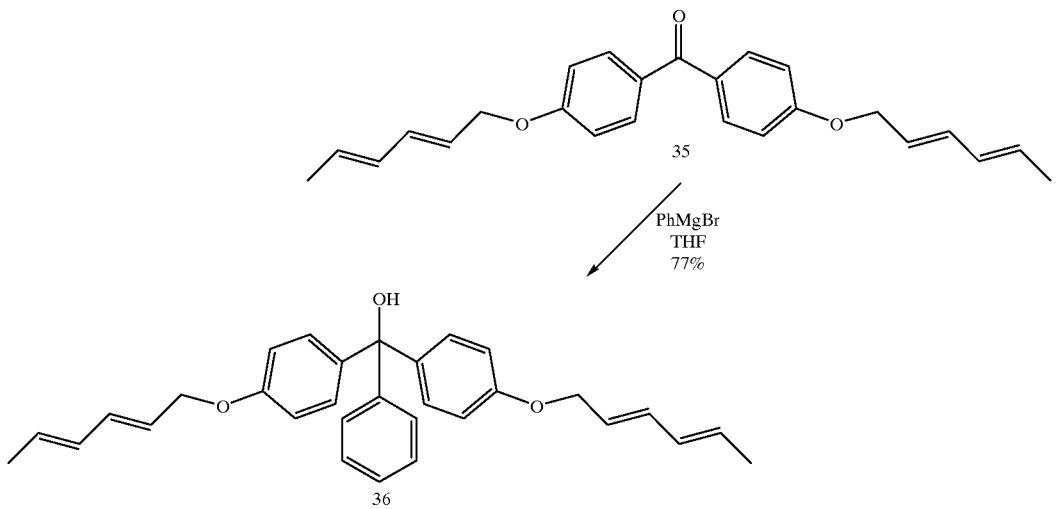

Preparation of 4,4'-di-2,4-hexadienoxybenzophenone (35)

4,4'-Difluorobenzophenone (34) (4.8 grams, 22 mmol) was dissolved in anhydrous DMF (1 liter). NaH (95%; 5.6 grams, 220 mmol) was added and the solution was cooled to 0° C. 2,4-Hexadienol (5.8 mL, 51 mmol) was slowly added to the solution and the reaction mixture was allowed to warm to room temperature with stirring under argon overnight. The reaction mixture was concentrated in vacuo, dissolved in dichloromethane, and washed with water. The organic phase was dried (MgSO$_4$) and concentrated and purified by column chromatography (silica gel; hexane/CH$_2$Cl$_2$, 1/3) to afford 2.07 grams (25%) of compound 35 as a white solid. $^1$H NMR (300 MHz, DMSO-d$_6$) δ 1.73 (d, J=6.6 Hz, 6H), 4.68 (d, J=6.0 Hz, 4H), 5.69–5.84 (m, 4H), 6.05–6.19 (m, 2H), 6.31–6.45 (m, 2H), 7.08 (d, J=9.0 Hz, 4), 7.68 (d, J=10.2 Hz, 4).

Preparation of 4,4'-di-2,4-hexadienoxytrityl alcohol (36)

Compound 35 (2.0 grams) was dissolved in THF (45 mL) and phenylmagnesium bromide (1.0 M solution in THF; 10.6 mL, 10.6 mmol) was added to the solution. The reaction mixture was stirred at room temperature for 3 hours, and evaporated to dryness under vacuum. The residue was redissolved in dichloromethane and washed with a saturated solution of ammonium chloride, followed by water. The organic phase was dried (MgSO$_4$), concentrated in vacuo and purified column chromatography (silica gel; hexane/CH$_2$Cl$_2$, 1/9) to afford 1.84 grams (77%) of compound 36 as a pale yellow solid. $^1$H NMR (300 MHz, DMSO-d$_6$) δ 1.73 (d, J=6.9 Hz, 6H), 4.54 (d, J=6.0 Hz, 4H), 5.68–5.80 (m, 4H), 6.02, 6.11 (m, 2H), 6.20–6.37 (m, 2H), 6.85 (d, J=6.9 Hz, 4H), 7.05 (d, J=7.0 Hz, 4H), 7.14–7.32 (m, 5H); Anal. Calcd for C$_{31}$H$_{32}$O$_3$ (452.5920): C, 82.27; H, 7.13; Found: C, 82.30; H, 7.11.

The 5'-di-(2,4-hexadienoxy)tritylthymidine phosphoramidite monomer can be prepared from compound 36 using the same procedure described above for the preparation of the 5'-O-(4,4'-di-3,5-hexadienoxytrityl)thymidine phosphoramidite (32).

EXAMPLE 9

Diels-Alder cycloaddition of diene substituted trityl alcohols with N-ethylmaleimide Example 9 (Scheme 9) describes the Diels-Alder reaction of diene substituted trityl alcohols—4,4'-di-3,5-hexadienoxytrityl alcohol (30) and 4,4'-di-2,4-hexadienoxytrityl alcohol (36)—with N-ethyl maleimide (Reactions 1 and 2 respectively). Table 4 sets forth the reaction rates for these two reactions under various reaction conditions.

SCHEME 9

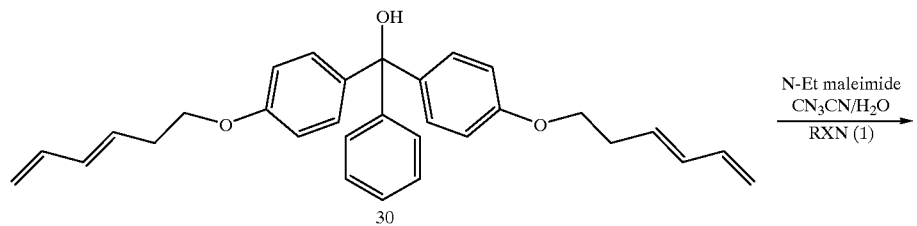

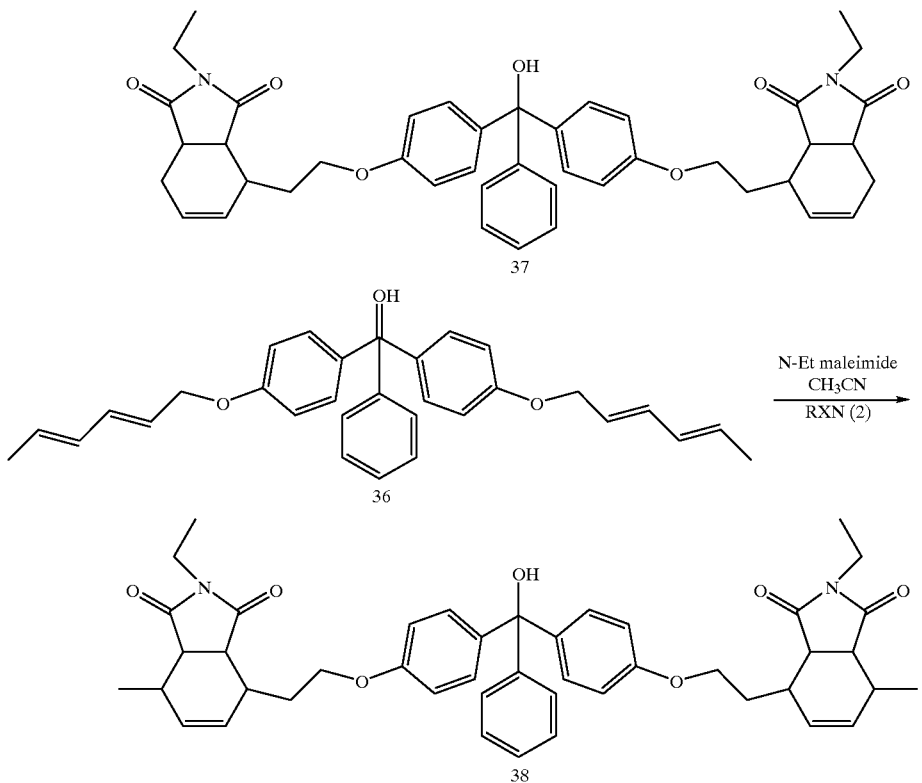

Diels-Alder reaction of 3,5-hexadienoxytrityl alcohol (30)—Reaction 1

Compound 30 (50 mg, 0.11 mmol) was dissolved in acetonitrile (0.75 mL) and water (0.75 mL). N-ethyl maleimide (N-Et maleimide) (138 mg, 1.1 mmol) was added and the reaction mixture was stirred at room temperature. After 3 hours $^1$H NMR analysis of the crude reaction mixture showed that the reaction had gone to completion. The reaction mixture was concentrated and loaded onto a silica gel plug pre-equilibrated with dichloromethane. The excess N-ethyl maleimide was washed off with dichloromethane and the product was eluted with 10% MeOH/CH$_2$Cl$_2$. The solvent was concentrated under reduced pressure to afford 38 mg (59%) of compound 37. $^1$H NMR (300 MHz, DMSO-d$^6$) δ 0.97 (t, J=7.2 Hz, 6H), 2.02–2.19 (m, 4H), 2.20–2.34 (m, 2H), 2.42–2.53 (m, 4H), 3.13–3.24 (m, 4H), 3.28–3.39 (m, 4H), 4.11 (t, J=6.3 Hz, 4H), 5.70–5.86 (m, 4H), 6.22 (s, 1H), 6.87 (d, J=9.0 Hz, 4H), 7.07 (d, J=9.0 Hz, 4H), 7.15–7.24 (m, 5H).

Diels-Alder reaction of 2,4-hexadienoxytrityl alcohol (36)—Reaction 2

Compound 36 (60 mg, 0.13 mmol) was dissolved in acetonitrile (2.0 mL). N-ethyl maleimide (166 mg, 1.3 mmol) was added and the reaction mixture was stirred at room temperature. After 24 hours $^1$H NMR analysis of the crude reaction mixture showed the reaction had gone to completion. The reaction mixture was concentrated and loaded onto a silica gel plug pre-equilibrated with dichloromethane. The excess N-ethyl maleimide was washed off with dichloromethane and the product was eluted with 10% MeOH/CH$_2$Cl$_2$ and concentrated under reduced pressure to yield 50 mg (54%) of compound 38. $^1$H NMR (300 MHz, DMSO-d$_6$) δ 0.95 (t, J=7.1 Hz, 6H), 1.32 (d, J=7.2 Hz, 6H), 2.48 (bs, 2H), 2.74 (bs, 2H), 3.05–3.46 (m, 8H), 4.26 (t, J=8.4 Hz, 2H), 4.50 (t, 8.4 Hz, 2H), 5.67–5.86 (m, 4H), 6.27 (s, 1H), 6.88 (d, J=8.7 Hz, 4H), 7.11 (d, J=8.7 Hz, 4H), 7.16–7.35 (m, 5H); Anal. Calcd for C$_{43}$H$_{46}$N$_2$O$_7$.2H$_2$O (738.8762): C, 69.90; H, 6.82; N, 3.79. Found: C, 71.16; H, 6.71; N, 3.92.

EXAMPLE 10

Preparation of 3'-PEG-linked oligonucleotides using product capture by Diels-Alder cycloaddition Example 10 (Scheme 10) provide the general procedures to be followed for each monomer addition cycle, for the preparation of a 3'-PEG anchored oligonucleotide by solution phase synthesis using the Diels-Alder cycloaddition reaction for the covalent capture of the oligonucleotide product.

SCHEME 10

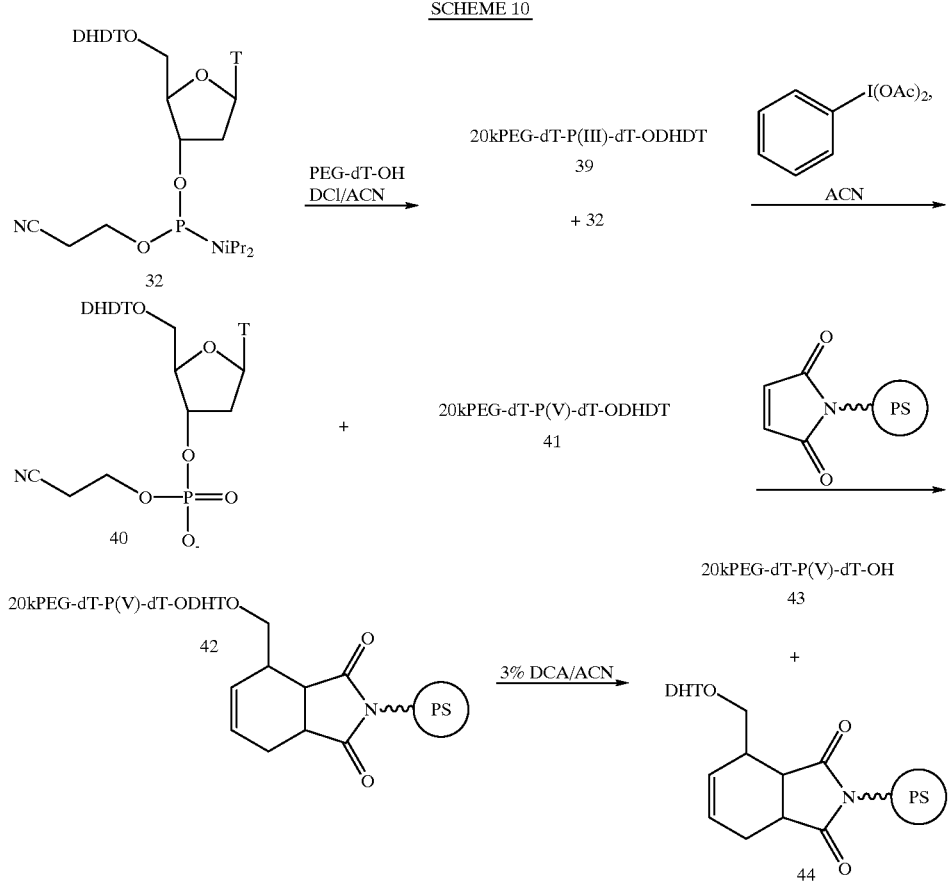

Coupling Reaction: PEG-dT-OH (20 k, 2.36 g, 0.11 mmol, loading: 46 μmol/g) was dissolved in 20 mL of dry acetonitrile ($CH_3CN$) under an atmosphere of dry argon. To this solution was added 5'-O-(4,4'-di-3,5-hexadienoxytrityl) thymidine 3'-phosphoramidite (32) (140 mg, 0.16 mmol), followed by DCI in $CH_3CN$ (0.65 mL, 1.0 M, 6.0 equivalents). The reaction was stirred under an atmosphere of dry argon for 25 minutes, after which 350 mL of dry $Et_2O$ was added to precipitate out the 20 k-PEG containing material. The solids were filtered and washed with $Et_2O$ (2×100 mL) and dried under vacuum for 1 hour to yield 2.3 g of a white solid (98% mass yield).

Oxidation: The white solid, which contains coupled product 39, unreacted phosphoramidite 32 and unreacted PEG-dT-OH, is redissolved in 20 mL $CH_2Cl_2$ and oxidized with iodobenzene diacetate in $CH_3CN$ (8.5 mL, 0.1 M, 0.27 g). After stirring for 8 minutes, the reaction mixture contains unreacted PEG-dT-OH, oxidized amidite monomer 40 and the oxidized oligomer 41. The reaction mixture is then treated with 350 mL of dry $Et_2O$ to precipitate the 20 k-PEG containing material and the solids are filtered and washed with 2×100 mL $Et_2O$. After drying under vacuum for 1 hour, a white solid is isolated which contain the unreacted PEG-dT-OH and the oligomer 41.

Diels-Alder Cycloaddition: The solids are redissolved in 20 mL of 50% $H_2O/CH_3CN$ and loaded onto 1.2 g (10 equivalents based on a maleimide loading of 0.4 mmol maleimide/g resin) of maleimide-functionalized polystyrene, which has been prewetted with 5 mL of 50% $H_2O/CH_3CN$. The reaction is warmed to 45° C. for 1 hour under an atmosphere of argon. It is expected that reverse-phase HPLC analysis of the supernatant liquid will reveal that the 5'-protected oligomer 41 has been completely consumed. The maleimide-derivatized polystyrene 42 can then be filtered and washed with 10 mL of 50% $H_2O/CH_3CN$, to yield 3.5 g of 3'-PEG-5'-DHDT Diels-Alder conjugate oligomer (42) as a solid resin.

Detrylation/Oligonucleotide Release: It is anticipated that the 3.5 g of Diels-Alder conjugate resin 42 (loading: 75 μmol/g) can be suspended in 20 mL of $CH_2Cl_2$. To this suspension is added a mixture of DCA and trihexylsilane (6.4 mL, 80 equivalents) in $CH_2Cl_2$. After 9 minutes the polystyrene-maleimide resin (44) is removed via filtration. The PEG-nucleoside (43) is then precipitated twice with $Et_2O$ (500 mL), washed, filtered and dried under vacuum. The resultant PEG-nucleoside is deprotected at the 5'-position and is ready for the next coupling reaction of the sequence.

EXAMPLE 11

Preparation of non-PEG derivatized oligonucleotides by Diels-Alder product capture Scheme 12 illustrates a general reaction scheme for the preparation of a non-PEG derivatized oligonucleotide by Diels-Alder product capture using a 5'-O-(4,4-di-3,5-hexadienoxy trityl)nucleoside (5'-O-DHDT-nucleoside) as the diene and a maleimide substituted solid support as the dienophile. Briefly, the Diels-Alder capture PASS cycle is performed in the following manner: A 3'-blocked oligomer is coupled in the usual fashion with a 5'-O-(4,4'-hexadienoxytrityl)nucleoside 3'-phosphoramidite. The 3'-blocking group is a lipid or polysaccharide, or a more traditional solution-phase blocking group such as acetyl, pyranyl, or silyl group, such as tert-butyldiphenylsilyl ether.
SCHEME 12
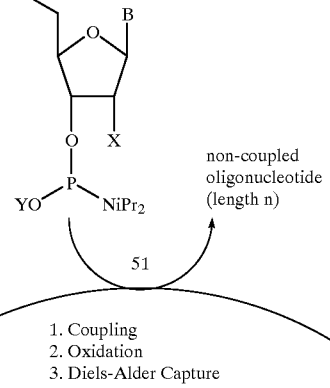
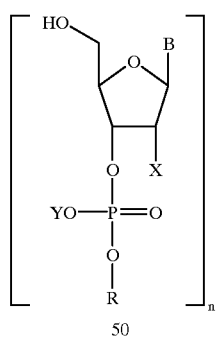
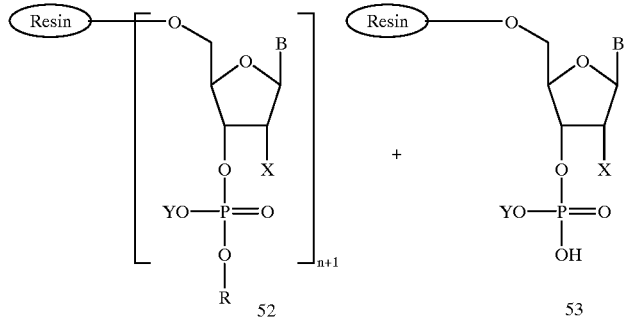

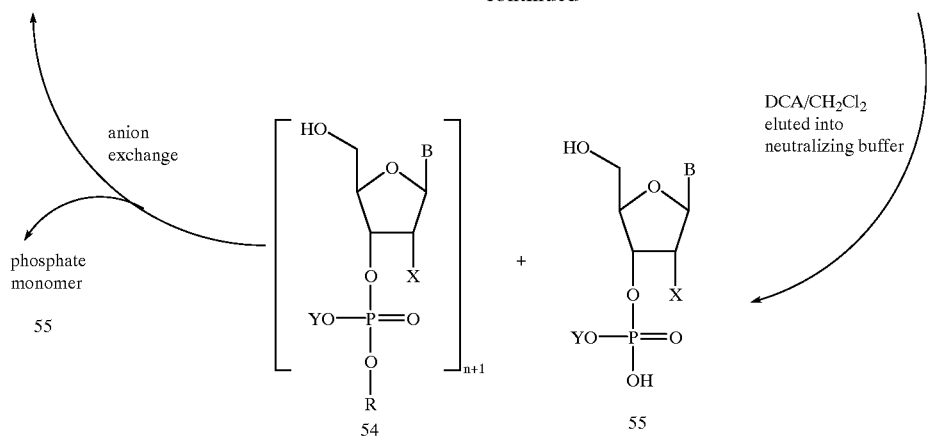

DHDT: 4,4'-di-3,5-hexadienoxytrityl
Resin: Maleimide-derivatized solid support (CPG, silica, cellulose, HLP, etc)
X: any suitably protected 2'-substituent
Y: phosphate protecting group
B: suitable protected, modified, or derivatized nucleobase
R: oligonucleotide or 3'-blocking group Coupling/Oxidation/Capture Sequence. In $CH_3CN$, the appropriate 3'-blocked oligonucleotide of length n (50) is coupled with 2.0 equivalents of the amidite monomer 51 by treatment with a 1.0 M solution of DCI in $CH_3CN$. The coupling reaction takes less than 25 minutes and is monitored by TLC. Upon completion of the coupling reaction, the solution is treated directly with 8.0 equivalents of iodobenzene diacetate as a 0.1 M solution in $CH_3CN$. The oxidation sequence is complete within 8 minutes and the crude reaction mixture is applied directly to the solid support bearing the dienophile. Polystyrene, bearing a maleimide dienophile is the preferred solid support. The Diels-Alder cycloaddition reaction is accelerated by utilizing a solvent of 1:1 $CH_3CN:H_2O$. The oligonucleotide, now covalently bound to the solid support 52, is easily separated from the unreacted starting oligonucleotide 50 (failure sequence) and reagents via simple filtration and washing of the resin beads. The amidite monomer 51 which also has a 5'-DHDT group is also bound to the resin (53).

Detritylation/Release Sequence. The washed and dried resin, bearing the covalently bound oligonucleotide (52), as well as, unreacted monomer phosphate (53), is washed with a solution of 3% $DCA/CH_2Cl_2$, eluting into a neutralizing buffer to prevent acid-mediated decomposition of the oligonucleotide chain. The released oligomer (54) and monomer phosphate (55) are separated from one another via aqueous extraction. The product oligonucleotide in the organic phase is dried and exchanged into acetonitrile by ultrafiltration.

EXAMPLE 12

Preparation of a Dimer using Product capture by Diels-Alder cycloaddition

SCHEME 15

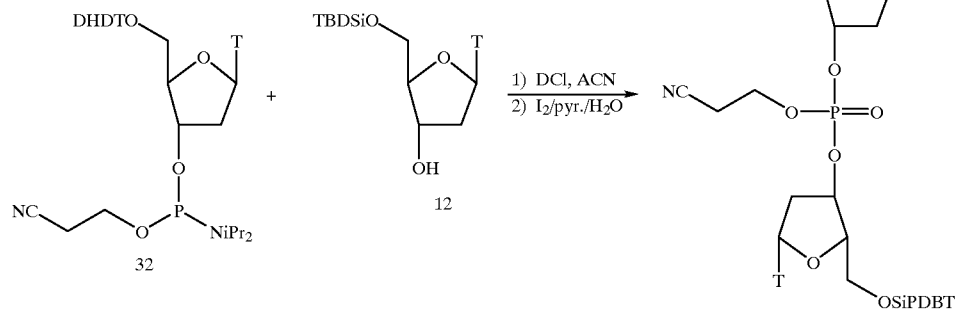

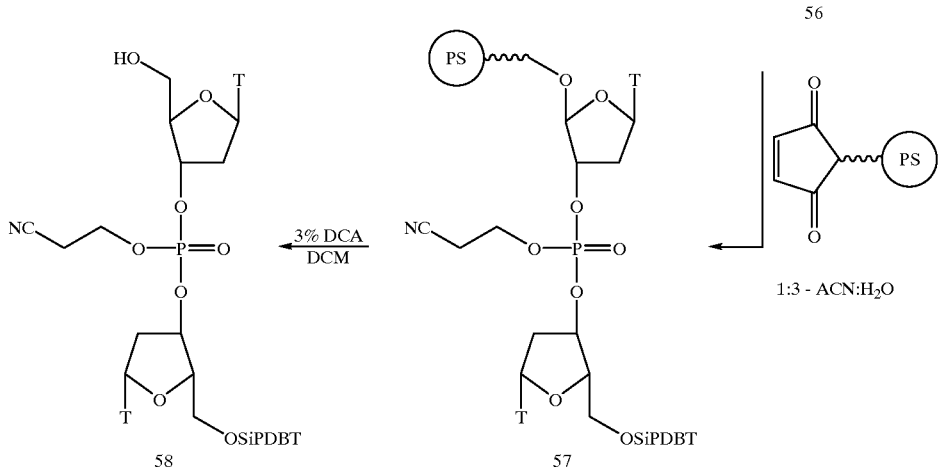

Preparation of 5'-DHDTO-T-[3', 3']-T-OSiPDBT-5' (56)

5'-TBDPSiO-dT-3'-OH (12) (0.21 g, 0.43 mmol) was dissolved in 10 mL acetonitrile. 5'-DHDTO-dT phosphoramidite (32) (0.5 g, 0.52 mmol) was added to this solution followed by 3.0 mL of 1.0 M DCI in acetonitrile (3.0 mmol). This solution was stirred under argon for 20 minutes, at which time 11 mL of a solution of 0.2 M $I_2$ in pyridine/water was added. The oxidation reaction was allowed to proceed for 5 minutes and was filtered (4×) through DEAE Sephadex® to remove most of the yellow color. A yellow solid 56 (0.23 g) was isolated.

Figure 7:
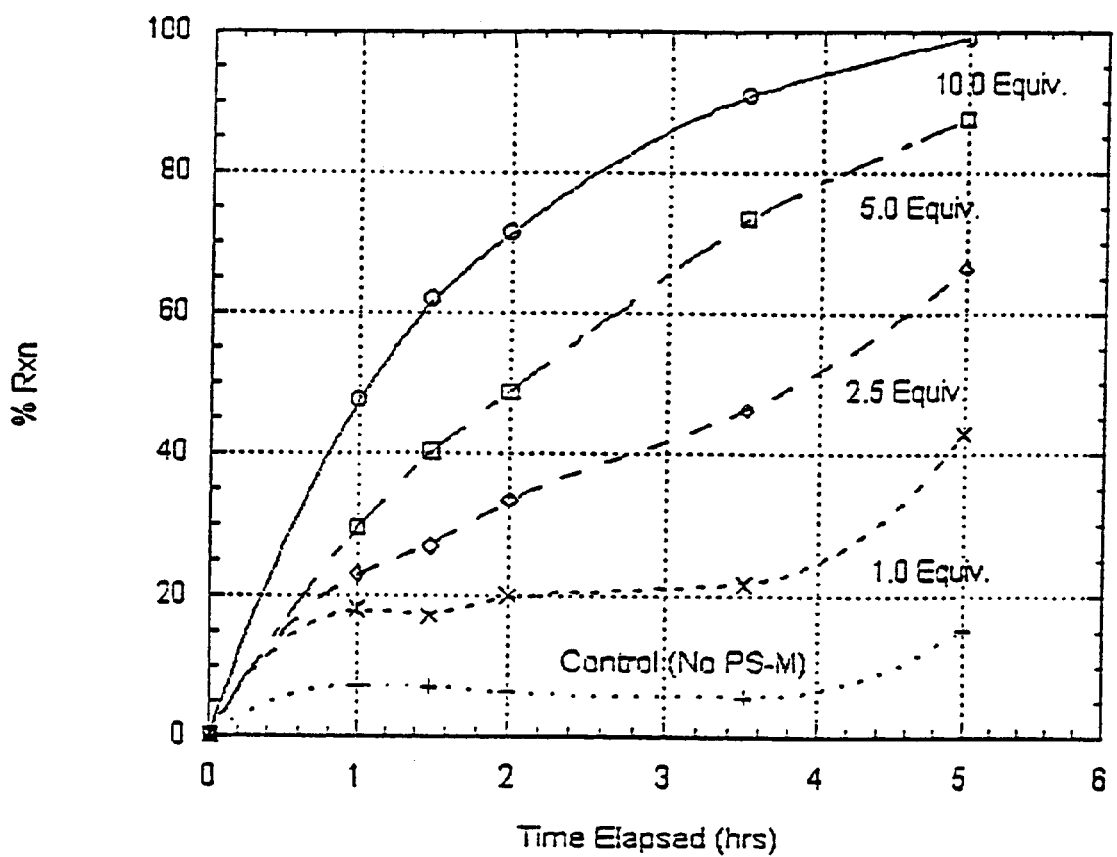
FIG. 7 illustrates graphically the Diels-Alder capture data for the reaction of 5'-DHDTO-T-[3',3']-T-OSiPDBT-5' with polystyrene maleimide resins containing 1.0 eq, 2.5 eq, 5 eq and 10 eq of maleimide.

Product Capture: The Diels-Alder capture reaction was performed with variation in the amount of polystyrene supported maleimide (PS-M) used, as follows: 10 eq, 5 eq, 2.5 eq, 1 eq. The procedure below for all of the reactions was as follows. The [3',3']-dT-dT-OTDHD dimer (11 μmol) (56) was dissolved in 400 μL of acetonitrile. This solution was added to a suspension of PS-M in 1.0 mL of 3/1 $CH_3CN$/water and then warmed to 65° C. The course of the reaction was monitored by TLC (2/1 EtOAc/hexanes), by the disappearance of the reactant at $R_f$=0.15, and via HPLC analysis (C18, 4.6×100 mm, Buffer A: 100 mM triethylammonium acetate pH 7.5, Buffer B: acetonitrile, 0 to 80% B over 2.5 minutes). The % reaction was determined by comparison to the initial ratio of dimerized material (2.65 min) to unreacted 5'-TBDPSiO-dT-3'-OH monomer (12) (1.71 min). (See FIG. 7). It is interesting to note that the lines drawn for 2.5 equiv., 1.0 equiv., and control (No PS-M) all show reaction (disappearance of dimer) occurring after 4 hours. The reaction is not a Diels-Alder capture, but is rather decomposition of the dimer via what is believed to be hydrolysis. A new material at 1.47 minutes and 2.30 minutes appears in the HPLC traces. This material may be 5'-TBDPSiO-dT-3'-phosphate (1.47 minutes) and 5'-DHDTO-dT-3'-phosphate. Since 5'-TBDPSiO-dT-3'-OH is also expected to be produced in the course of the hydrolysis reaction, the relative rates of Diels-Alder capture cannot be directly obtained from these traces as the internal standard is not appropriate in the cases where hydrolysis is evident. Hydrolysis can be corrected for by adjusting to the amount of 5'-TBDPSiO-dT-3'-phosphate evident in the later traces. This process is not significant in the case of 5.0 equiv. and 10.0 equivalents.

Release/Detritylization: 286 mg of PS-M derivatized with 11 μmol of the [3',3'] dimer 57 was suspended in 0.25 mL dichloromethane. To this solution was added 2.6 mL of 3% DCA in dichloromethane. The PS-M immediately turned bright orange. The suspension was agitated for 5 minutes, whereupon the dichloromethane solution was removed via filtration from the PS-M. The solution obtained was immediately filtered through a pad of Dowex-Cl⁻ ion exchange resin with dichloromethane. The filtrate was then concentrated to yield 12 mg of a white, glassy solid (contains some residual solvent and aliphatic impurities). $^1$H NMR and $^{31}$P-NMR are consistent with the desired product compound 58.

EXAMPLE 13

Preparation of an oligonucleotide from two blocks using fragment anchoring by Diels-Alder cycloadditon The PASS oligonucleotide synthesis scheme allows facile and efficient preparation of oligonucleotide blocks, which can be coupled to each other in a modified PASS cycle as illustrated in Scheme 16. Briefly, the oligonucleotide block 59, prepared by PASS monomer addition cycles as outlined above, is reacted with a maleimide resin to give the resin anchored oligonucleotide block 61. The 3'-terminal PEG is removed from this block by reductive cleavage of linker L with titanium trichloride, yielding resin bound fragment 63, which has a free 3'-terminus. Phosphitylation of 63 with N,N-diisopropyl-2-cyanoethyl-chlorophosphine results in the 3'-terminal phosphoramidite 64. Compound 64 is then coupled to oligonucleotide block 62, obtained from detritylation of oligonucleotide block 60 after capture on a maleimide resin and subsequent detritylation. The coupling reaction is followed by oxidation of the phosphite triester linkage to the corresponding phosphate triester, followed by release of the product oligonucleotide from the resin with dichloroacetic acid, giving oligonucleotide fragment 60.

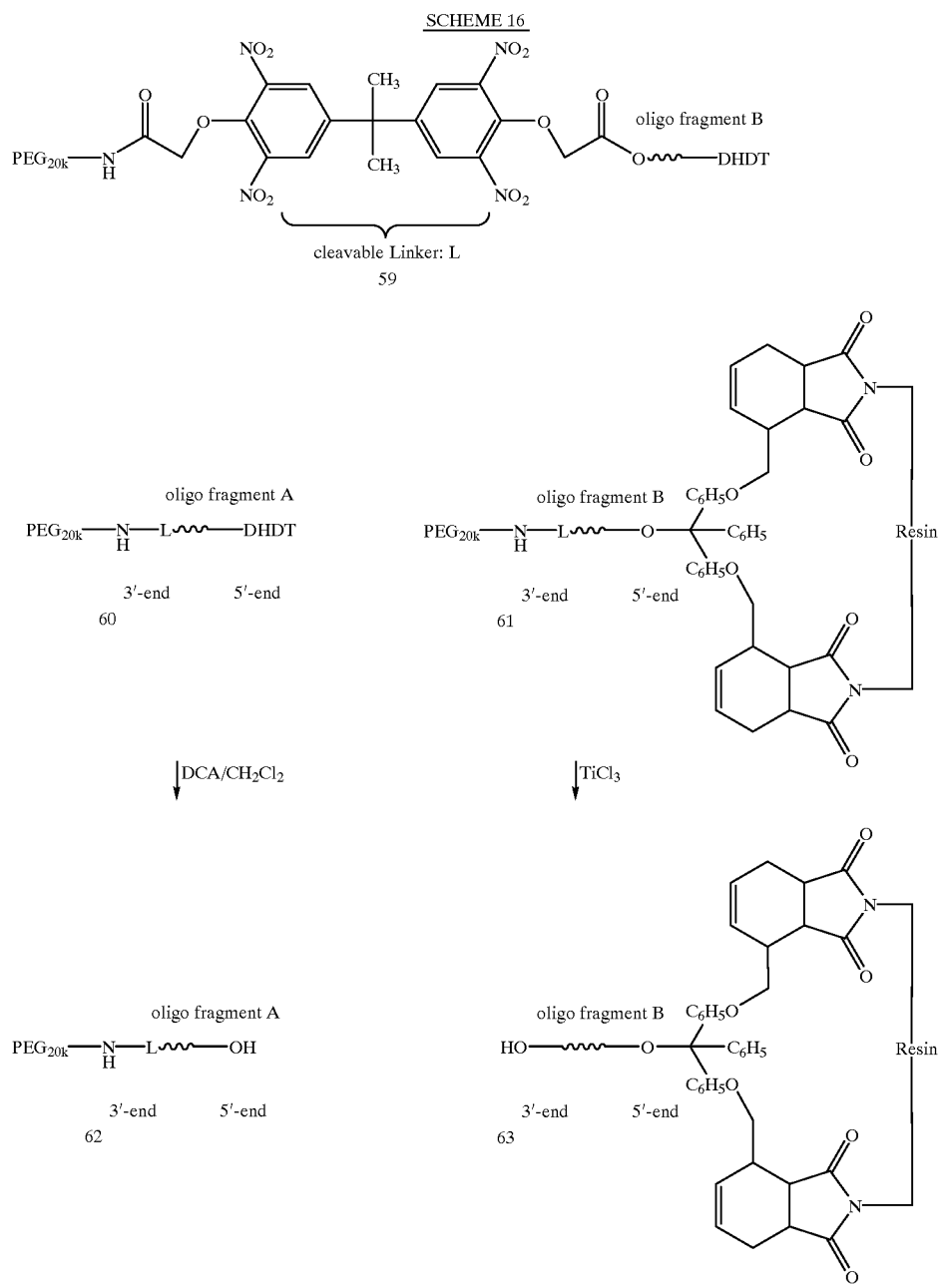

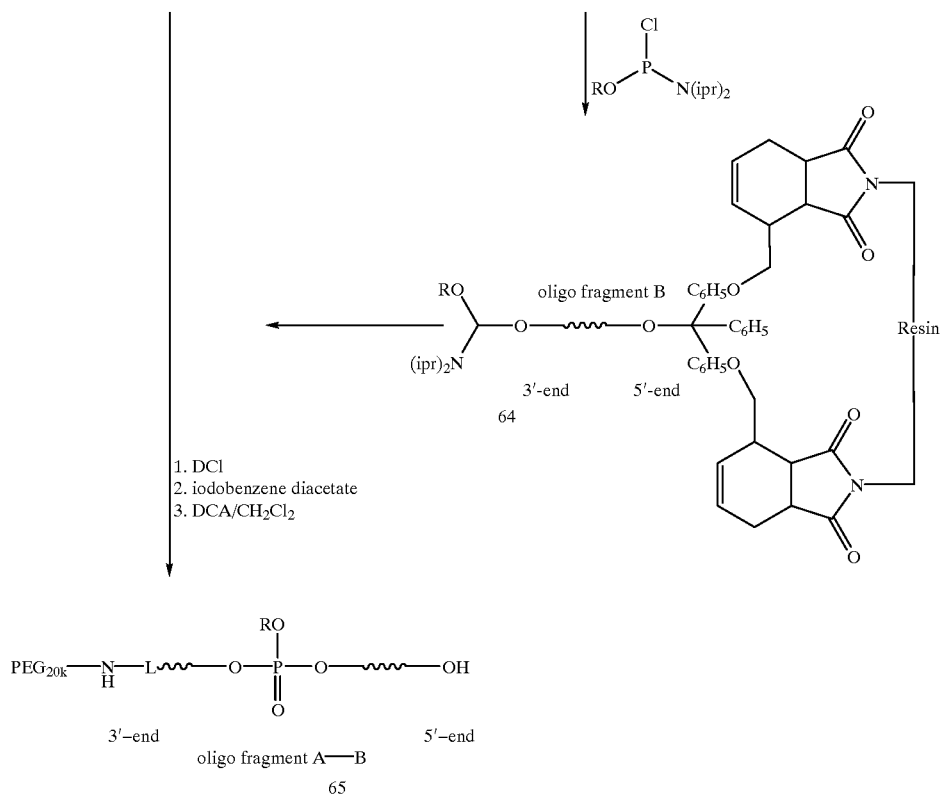

EXAMPLE 14

Automation of PASS using Diels-Alder product capture for preparation of oligonucleotides The coupling reagents are added to reaction vessel 212 and reaction is allowed to proceed as described in Example 10. Upon completion of the coupling reaction, the reaction mixture is circulated through the diene or dienophile modified resin or membrane (hereafter referred to as the support), which is contained in vessel 214, to covalently capture the oligonucleotide. The time required for the capture step can be controlled by monitoring the disappearance of the coupling product from solution either by an HPLC or in line UV assay (not shown). The support is then rinsed to elute all failure sequences not containing the diene or dienophile. Oxidation can be accomplished either after the oligonucleotide is attached to the support or in solution prior to attachment to the dienophile support. The oxidation solution must be thoroughly removed from the resin prior to detritylation. This removal is conveniently controlled by in-line conductance monitoring (not shown). The support is then rinsed with DCA/CH$_2$Cl$_2$ to remove the growing oligomer and captured excess monomer from the resin, thus allowing the only species in the solution to be the 5'-deprotected oligonucleotide and monomer in a DCA/CH$_2$Cl$_2$ mixture. This mixture is then brought into contact with a membrane separator (218) to remove the DCA and the excess monomer, in addition to a solvent exchange to acetonitrile. Alternatively, the monomer may be separated by precipitation or extraction. The only species remaining in solution is the macromolecule attached oligomer in acetonitrile. This solution is now ready for the next coupling reaction.

The removal of all n-1 species with use of the dienophile support, thus eliminates the use of a capping step, and the solution is ready to be oxidized and or circulated through the dienophile support. The dienophile support can contain a cleavable linker between the dienophile moiety and the resin or membrane, such as an amide bond. This cleavable linker allows facile regeneration of the dienophile support. Linkers such as these are well known to those skilled in the art.

Membrane Evaluation

Recovery of Pegylated Deoxythymidine after Exposure to a Polypropylene Ultrafiltration Membrane: Acetonitrile Solvent System. A solution of 2.74 mM 20 k PEG-deoxythymidine (PEG-dT) was made by dissolving 1.49 grams of 46 µmol dT/gram PEG-dT in 25 ml of acetonitrile. Aliquots (2 mL) of the solution were then exposed to areas of 5.73 square centimeters of the working surface of a polypropylene ultrafiltration membrane (3M®) for periods of 0.25, 1 and 4 hours in 50 mL Falcon® tubes. The starting solution was rinsed from the Falcon® tubes and membranes with two 25 mL washes of acetonitrile. The wash solvent was assayed for PEG-dT spectrophotometrically by absorbance at 260 nm and balanced relative to the absorbance of the starting PEG-dT. A control to measure losses to the tube and glassware was performed by exposing a Falcon® tube without a membrane to 2 mL of the starting solution for 4 hours and assaying for PEG-dT at 260 nm. Results are shown in Table 6.

Recovery of Pegylated Deoxythymidine after Exposure to a Polypropylene Ultrafiltration Membrane: Methylene Chloride Solvent System. A solution of 2.72 mM 20 k PEG-deoxythymidine (PEG-dT) was made by dissolving 1.48 grams of 46 µmol dT/gram PEG-dT in 25 mL of methylene chloride. Aliquots (2 mL) of the solution were then exposed to areas of 5.73 square centimeters of the working surface of a polypropylene ultrafiltration membrane (3M®) for periods of 0.25, 1 and 4 hours in 50 mL Falcon® tubes. The starting solution was rinsed from the Falcon® tubes and membranes with two 25 mL washes of methylene chloride. The wash solvent was assayed for PEG-dT spectrophotometrically by absorbance at 260 nm and balanced relative to the absorbance of the starting PEG-dT. A control to measure losses to the tube and glassware was performed by exposing a Falcon® tube without a membrane to 2 mL of the starting solution for 4 hours and assaying for PEG-dT at 260 nm. Results are shown in Table 7.

Recovery of Pegylated Deoxythymidine after Exposure to a Regenerated Cellulose Ultrafiltration Membrane: Acetonitrile Solvent System. A solution of 2.85 mM 20 k PEG-deoxythymidine (PEG-dT) was made by dissolving 1.55 grams of 46 μmol dT/gram PEG-dT in 25 mL of acetonitrile. Aliquots (2 mL) of solution were exposed to areas of 5.73 square centimeters of the working surface of a polypropylene ultrafiltration membrane (Millipore$^a$, 10KPLGC) for periods of 0.25, 1, 4 and 24 hours in 50 mL Falcon® tubes. The starting solution was rinsed from the Falcon® tubes and membranes with a 25 mL wash of acetonitrile. The membrane was soaked in 25 mL of acetonitrile for six days and then washed with an additional 25 mL of acetonitrile. The wash solvents were assayed for PEG-dT spectrophotometrically by absorbance at 260 nm and balanced relative to the absorbance of the starting PEG-dT. A control to measure losses to the tube and glassware was performed by exposing a Falcon® tube without a membrane to 2 mL of the starting solution for 4 hours and assaying for PEG-dT at 260 mn. Results are shown in Table 8.

Figure 9:
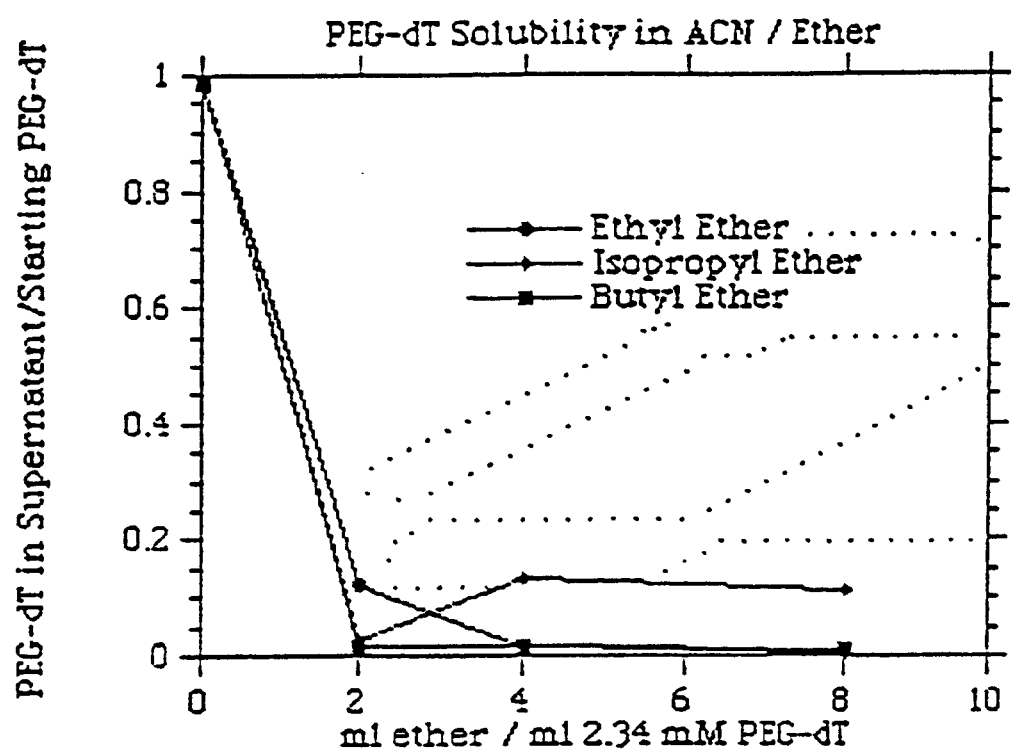
FIG. 9 illustrates graphically the precipitation and centrifugation of PEG-precipitated by ethyl ether, isopropyl ether and N-butyl ether.

Centrifugation of Pegylated Deoxythymidine in Acetonitrile/Ether: Diethyl Ether, Diisopropyl Ether and N-Butyl Ethers Compared. A solution of 2.34 mM 20k PEG-deoxythymidine (PEG-dT) was made by dissolving 0.4855 grams of 46 mol/gram PEG-dT in 10 ml of acetonitrile. Aliquots of 0.5, 0.25 and 0.125 mL were precipitated by addition of 1 mL of either diethyl ether, diisopropyl ether or N-butyl ether. The precipitates were centrifuged at approximately 4,400 times gravity for 2 minutes. The PEG-dT content of the supernatants was determined spectrophotometrically and balanced relative to the starting-PEG-dT. A control to show losses to handling was performed by centrifuging and assaying 1.5 mL of the starting solution by the above method. The results are summarized in FIG. 9.

Compatibility by Flux and FTIR evaluations. Polyvinylidienedifluroride (PVDF) and polypropylene membranes were evaluated by soaking them in the following solvent systems: acetonitrile, methylene chloride, the Coupling/Capping/Oxidation (c/c/0) solution in acetonitrile, and the mixture of 3% DCA in methylene chloride. Pieces of the membranes 1½" in diameter were submersed in the solutions, allowed to soak for 24 hours, placed into a membrane holder for flux evaluation of the initial solution, and then rinsed with acetonitrile for further acetonitrile flux evaluations. Thus, the membrane sample was rinsed of any excess reagent that may have remained on the membrane after soaking in solution. The acetonitrile flux rates after exposure to the various solvents are listed in Table 9. As can be seen, there are only minor changes in the flux rate in (mL/min/cm$^2$) between the PVDF and the polypropylene membranes.

In a retention study, the regenerated cellulose membrane was determined to have retained some of the PEG, as measured by FTIR. The silicone, ceramic, polyolefin and HDPE membranes are under investigation.

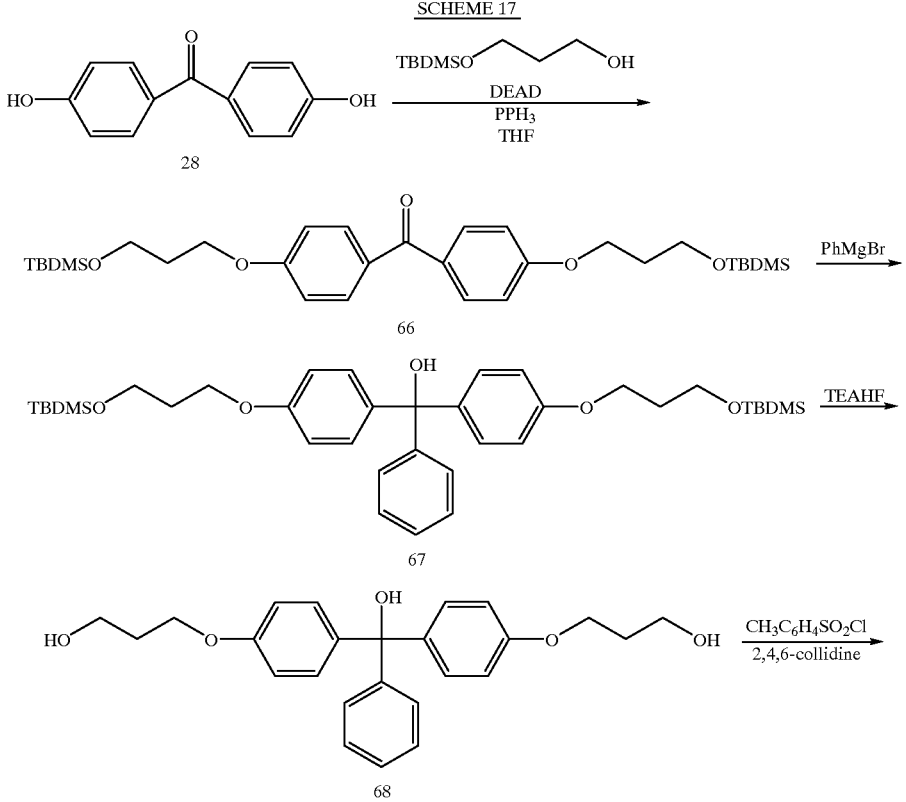

SCHEME 17

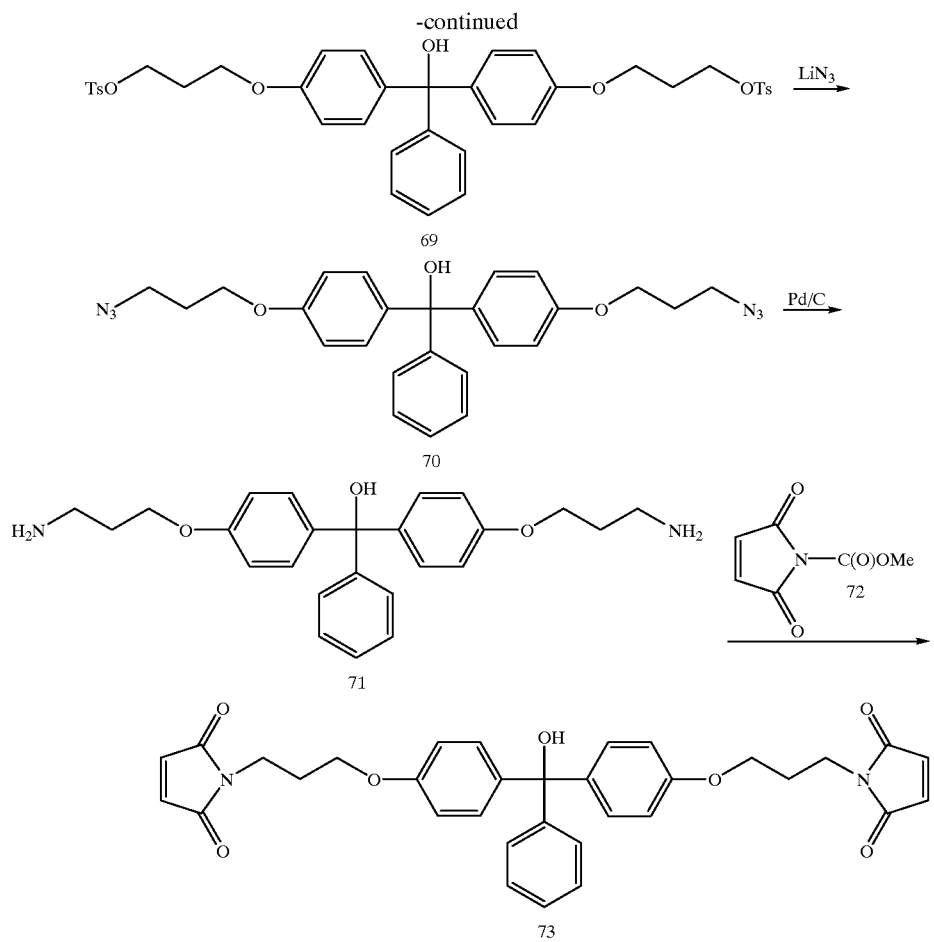

Preparation of 4,4'-di-(3-t-butyldimethylsilyloxypropoxy)-benzophenone (66)

4,4'-dihydroxybenzophenone (28) (10 g, 46.7 mmol) was reacted under Mitsunobu conditions with t-butyldimethylsilyloxy-3-propanol (40 g crude, approx. 150 mmol), DEAD (22.1 mL, 140.0 mmol) and triphenylphosphine (36.7 g, 140.0 mmol) in dry tetrahydrofuran at 0° C. The reaction was allowed to warm to room temperature under argon. After 24 hours the reaction was concentrated and the salts precipitated with hexane/ether and filtered. The remaining material was purified by column chromatography column chromatography (silica gel; gradient of hexane to 85% hexane/ethyl acetate) to afford to afford 14 g of the desired product compound 66 in 54% yield. $^1$H NMR (300 MHz, CDCl$_3$) δ 7.92 (d, 4H), 7.68 (d, 4H), 4.13 (t, 4H), 3.76 (t, 4H), 1.96–1.88 (m, 4H), 0.85 (s, 18H), 0.02 (s, 12H).

Preparation of 4,4'-di-(3-t-butyldimethylsilyloxypropoxy)-triphenylmethanol (67)

The protected benzophenone 66 (5.7 g, 10.2 mmol) was dissolved in 40 mL dry THF and phenylmagnesium bromide (20.5 mL, 20.4 mmol) was added. The reaction was stirred under argon at room temperature for 2 hours, concentrated, partitioned between dichloromethane and saturated ammonium chloride, and washed with water. The organic layer was dried (MgSO$_4$) and concentrated to yield 6.5 g of a yellow gum, compound 67, in quantitative yield and used directly in the next step. $^1$H NMR (300 MHz, CDCl$_3$) δ 7.27–7.17, 7.05, 6.82 (m, 13H), 6.23 (s, 1H), 3.99 (t, 4H), 3.73 (t, 4H), 1.91–1.83 (m, 4H), 0.84 (s, 18H), 0.02 (s, 12H).

Preparation of 4,4'-di-(3-hydroxypropoxy)-triphenylmethanol (68)

The trityl compound 67 (6.37 g, 10 mmol) was deprotected by treatment with triethylamine hydrofluoride (3.64 g, 30 mmol) in acetonitrile at room temperature for 16 hours. The reaction was concentrated and purified by column chromatography (silica, gradient: 1:1 hexane:ethyl acetate to ethyl acetate:5% methanol all with 1% triethylamine) affording 2.8 g of the desired product 68 as a yellow gum in 69% yield. $^1$H NMR (300 MHz, CDCl$_3$) δ 7.30–7.18, 7.06, 6.83 (m, 13H), 6.22 (s, 1H), 4.55 (t, 2H), 4.07–3.98 (m, 4H), 3.57–3.52 (m, 4H), 1.88–1.80 (m, 4H).

Preparation of 4,4'-di-(3-p-toluenesulfonoxypropoxy)-triphenylmethanol (69)

A solution of tosyl chloride (1.43 g, 7.49 mmol) and 2,4,6-collidine (1 mL, 7.49 mmol) in acetonitrile was added to compound 68 (1.39 g, 3.4 mmol) in 15 mL acetonitrile. The reaction was stirred at room temperature under argon for 2.5 days and then concentrated. The residue was purified by column chromatography (silica, 60% ethyl acetate in hexane with 1% triethylamine) to give 0.6 g of the tosylated compound 69 in 25% yield. $^1$H NMR (300 MHz, CDCl$_3$) δ 7.76 (d, 4H), 7.38 (d, 4H), 7.32–7.06, 7.01, 6.73 (m, 13H), 6.26 (s, 1H), 4.17 (t, 4H), 3.88 (t, 4H), 2.33 (s, 6H), 2.04–1.96 (m, 4H).

Preparation of 4,4'-di-(3-azidopropoxy)-triphenylmethanol (70)

To a solution of 69 (0.6 g, 0.84 mmol) in 15 mL of dry DMF was added lithium azide (0.12 g, 2.51 mmol). The reaction was stirred under argon at room temperature overnight, concentrated and purified by column chromatography (silica, 60% ethyl acetate in hexane with 1% triethylamine) to yield 0.38 g (100%) of compound 70 as a yellow gum. $^1$H NMR (300 MHz, CDCl$_3$) δ 7.34–7.17, 7.07, 6.85 (m, 13H), 6.25 (s, 1H), 3.99 (t, 4H), 3.50 (t, 4H), 2.00–1.77 (m, 4H).

Preparation of 4,4'-di-(3-aminopropoxy)-triphenylmethanol (71)

The azide (70) (0.25 g, 0.55 mmol) was warmed with activated charcoal in methanol, filtered and concentrated. The residue was again dissolved in 50 mL of methanol and 55 mg 5% palladium on carbon was added. The flask was evacuated and a hydrogen filled balloon added. After 1 hour at room temperature the catalyst was filtered. The reaction was concentrated and used directly in the next step.

Preparation of 4,4'-di-(3-maleimidopropoxy)-triphenylmethanol (73)

The crude residue 71 was dissolved in 50 mL 1:1 acetonitrile:water and stirred in ice bath. Methoxy carbonyl maleimide reagent (72) (0.16 g, 0.98 mmol) was added and over 2 hours the pH was observed to drop from 10.1 to 5. The pH was then adjusted to 2 with 1 M sulfuric acid and the reaction concentrated. The residue was partitioned between ethyl acetate and brine. The organic layer was concentrated, re-dissolved in 1:1 acetonitrile:water and stirred with 10 mL 5% sodium bicarbonate. After 17 minutes the reaction was acidified to pH 3 with 1 M sulfuric acid. Ethyl acetate (20 mL) was added and the solution was partitioned and the aqueous layer back extracted with ethyl acetate. The combined organic layers were concentrated and purified by column chromatography (silica, ethyl acetate and hexane mixtures) to give 0.104 g of product 73 in 36% yield. $^1$H NMR (300 MHz, CDCl$_3$) δ 7.30–7.18, 7.04, 7.68 (m, 13H), 7.02 (s, 4H), 6.24 (s, 1H), 3.92 (t, 4H), 3.57 (t, 4H), 1.99–1.89 (m, 4H). MS (MS+566). Anal. Calcd. for C$_{33}$H$_{30}$N$_2$O$_7$: C, 69.95; H, 5.34; N, 4.94. Found: C, 69.74; H, 5.67; N, 4.78.

EXAMPLE 16

Selective removal of failure sequences during non-PASS oligonucleotide synthesis by capping with a diene-modified capping reagent and subsequent capture of such species on a dienophile resin or membrane Preparation of 3,5-hexadienoic acid anhydride (74), 3,5-hexadienoxyacetic anhydride (75) and trihexadienoxysilyl chloride (76)

Compounds 74, 75, and 76 are prepared by standard methods known in the field. Compound 74 can be prepared from the 3,5-hexadienol by oxidation to the corresponding hexadienoic acid and subsequent dehydration. Compound 75 is obtained from reaction of iodoacetic anhydride with 3,5-hexadienol and compound 76 is a product of the reaction of silicon tetrachloride with 3,5-hexadienol. In addition to these methods of synthesis, compounds 74, 75, and 76 can be prepared by a variety of other methods.

Use of compound 75 as capping reagent and subsequent failure removal during 3'-PEG anchored solution phase synthesis A solution phase synthesis is performed as described in Example 7 with the exception that the capping reagent is altered and that a failure subtraction step is added. During the capping step equal amounts of 3,5-hexadienoxyacetic anhydride (75), 2,6-lutidine, and N-methylimidazole are simultaneously injected into the solution and stirred. Maleimide-derivatized polystyrene resin is added to the reaction mixture and stirring is continued. The resin is filtered off and the polymer is precipitated from ether as described in the detritylation procedure of Example 7.

Use of compound 76 as capping reagent and failure removal during conventional solid phase synthesis Conventional solid phase synthesis of DNA, RNA, and modified oligonucleotides is carried out according to the specifications given by the solid phase synthesizer manufacturer with the exception that tri(3,5-hexadienoxy)silyl chloride 76 is substituted for acetic anhydride in the capping reagent. Upon cleavage and deprotection of the oligonucleotide from the support the crude oligonucleotide is taken up in water/acetonitrile and maleimide-derivatized polystyrene is added to the solution. Upon complete reaction, the resin-bound failure sequences are filtered off and the product oligonucleotide is further purified if required.

EXAMPLE 17

Use of N-2,7-di(3,5-hexadienoxyacetyl)fmoc protected amino acid monomers for peptide synthesis by PASS Preparation of N-2,7-di(3,5-hexadienoxyacetyl)fmoc protected amino acid monomers (86)

SCHEME 19

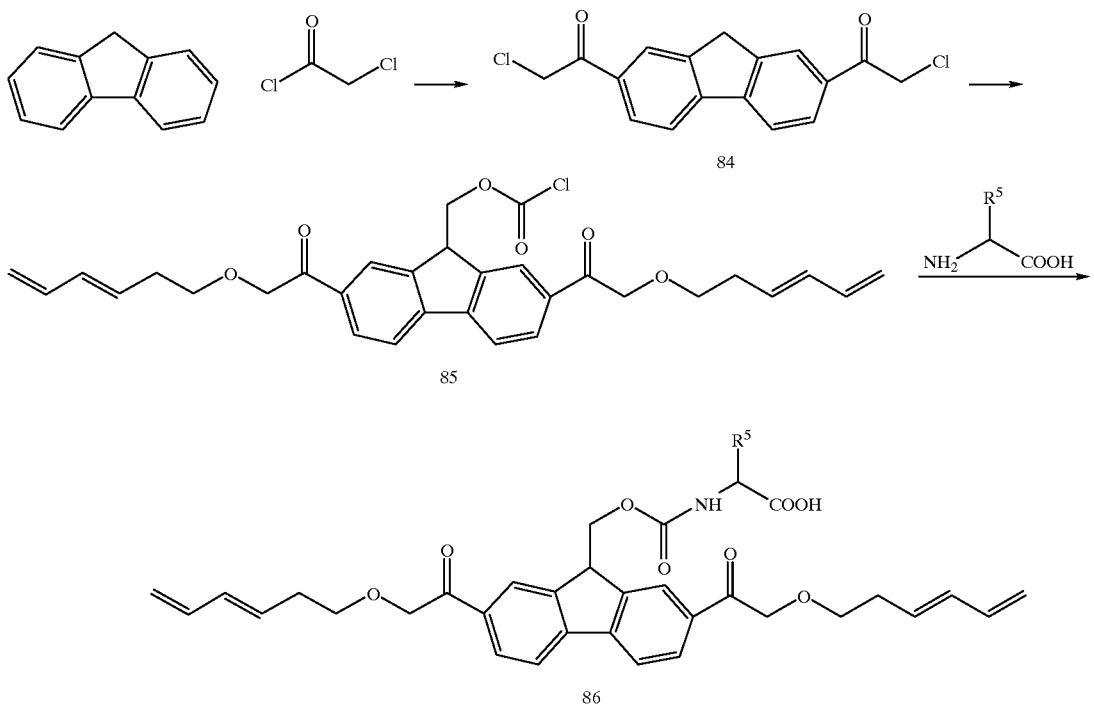

Scheme 19 outlines the synthesis of 2,7-di(3,5-hexadienoxyacetyl)fmoc protected amino acids 86. Briefly, Friedel-Crafts acylation of fluorene with chloroacetyl chloride gives the 2,7-chloroacetylfluorene derivative compound 84. (Leiserson and Weissberger (1955) Org. Synth III, 183). Nucleophilic substitution of the dichloride with 3,5-hexadienoxide yields 2,7-(3,5-hexadieneoxyacetyl)fluorene, which is converted to the 9-methylchloroformate derivative 85 by addition to formaldehyde and subsequent condensation with phosgene. (Bodansky and Bodansky (1984) in *The Practice of Peptide Synthesis* (Springer Verlag, Berlin). The hexadienoxyacetyl-fmoc chloroformate 85 is then condensed with the N-terminal amino group of a side-chain protected amino acid in standard fashion to yield the 2,7-di (3,5-hexadienoxyacetyl)fmoc protected amino acid 86. (Bodansky and Bodansky (1984) in *The Practice of Peptide Synthesis* (Springer Verlag, Berlin).

Peptide assembly with 2,7-di(3,5-hexadienoxyacetyl)fmoc protected amino acids by PASS Scheme 20 illustrates peptide assembly by PASS using 2,7-di(3,5-hexadienoxyacetyl)fmoc protected amino acids.

SCHEME 20

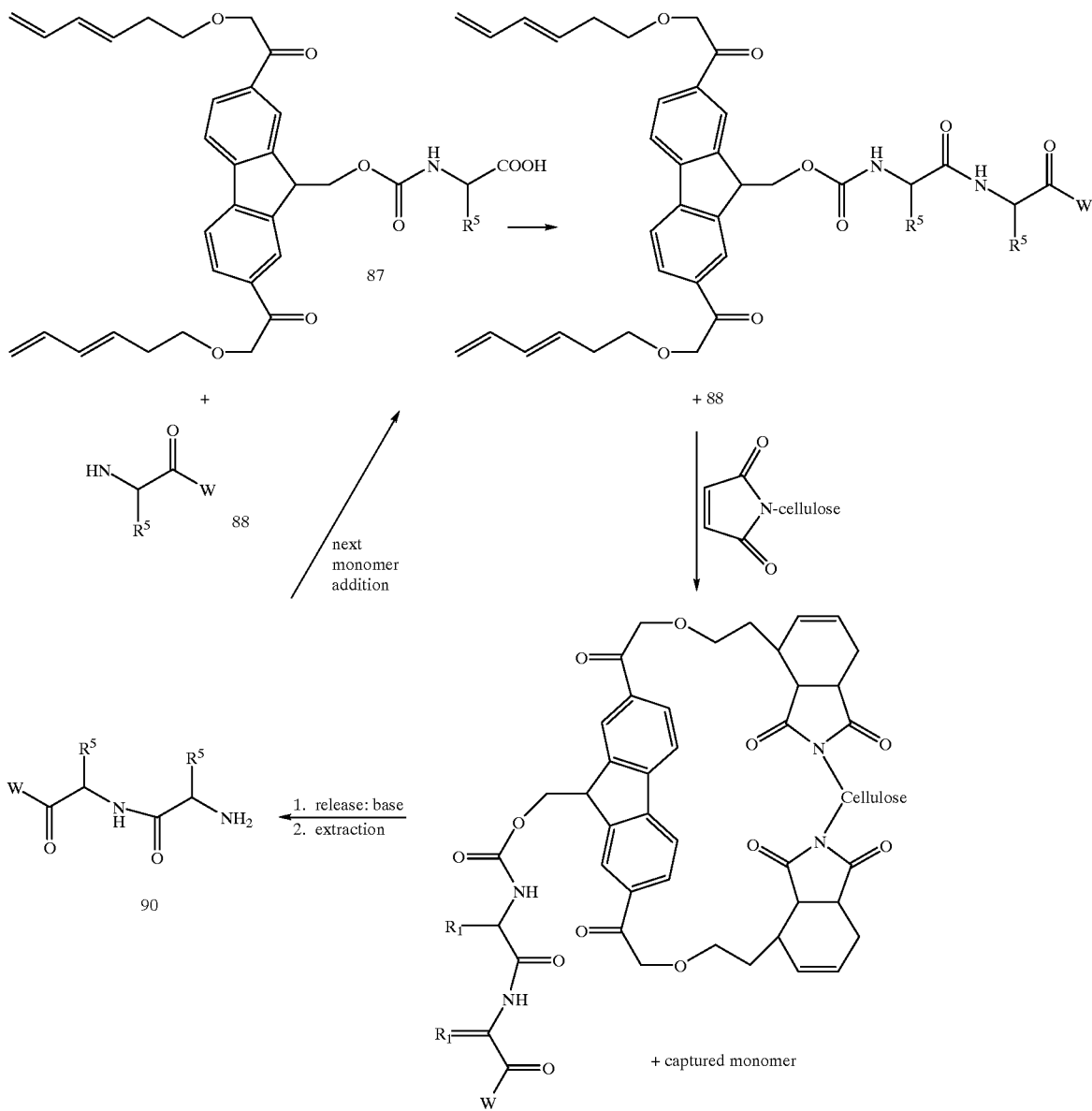

The hexadienoxy-fmoc protected amino acid monomer 87 is added to an extended peptide chain 88, where W is a peptide protected at the C-terminus with standard protecting groups, a blocking group, a soluble polymer or a diagnostic detector, each of which can be prepared by standard methods, to give product 89, together with unreacted 88 and excess amino acid monomer 87. (Bodansky and Bodansky (1984) in *The Practice of Peptide Synthesis* (Springer Verlag, Berlin).

From this mixture product 89 and excess monomer 87 are captured by Diels Alder cylcloaddition on maleimide derivatized cellulose. After washing away 88, the product is released from the resin by basic reagents typically used to remove the fmoc protecting group. The product 90 is separated from unprotected released excess monomer by extraction and 90 is then ready to undergo the next monomer addition to extend the peptide chain.

EXAMPLE 18

Preparation and use of 2,7-di(maleimido)fluorene-9-methylchloroformate for peptide synthesis by PASS

SCHEME 21

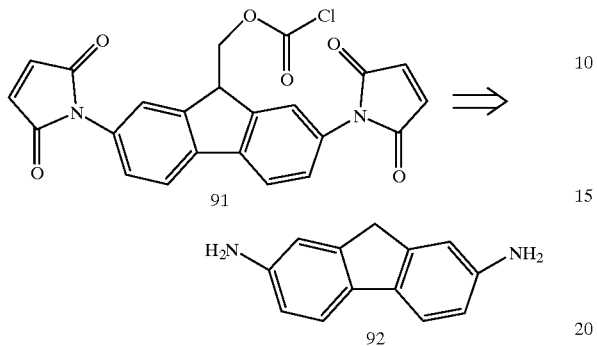

2,7-di(maleimido)fluorene-9-methylchloroformate 91 (Scheme 21) is prepared from the diaminofluorene 92 by condensation with maleic anhydride followed by conversion to the 9-chloroformate derivative 91 using standard methods. This protecting group can be used in a PASS peptide synthesis cycle analogous to Example 17, wherein the resin is hexadiene substituted cellulose, rather than maleimide derivatized cellulose.

EXAMPLE 19

Peptide assembly using hexadienoxy-Boc protected amino acids by PASS

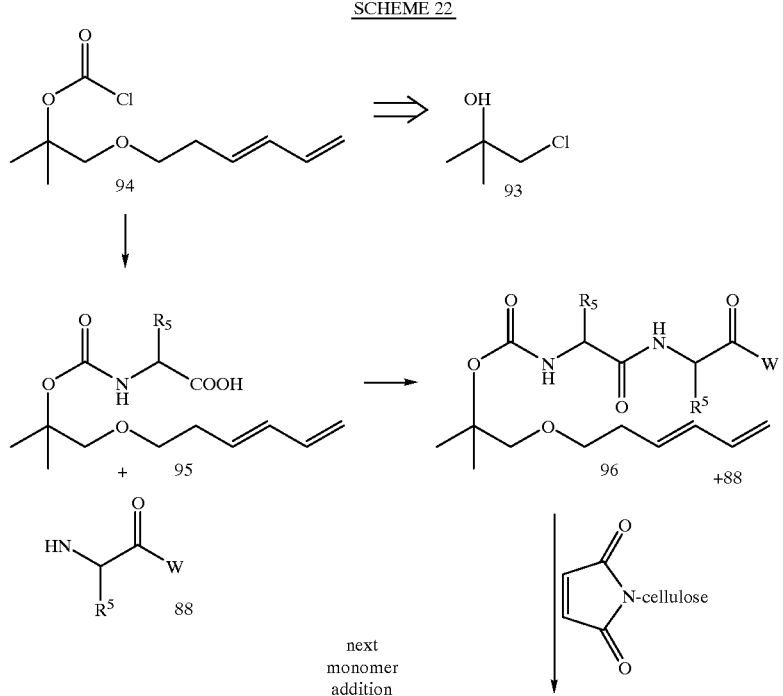

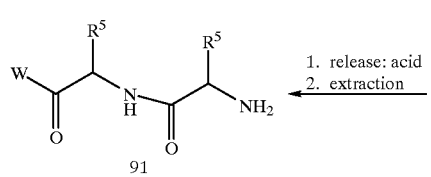 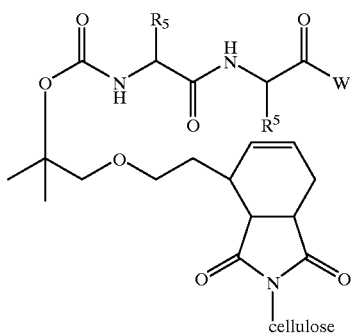

+ captured monomer

The hexadienoxy-Boc protecting group 94 is prepared from 93 by reaction with 3,5-hexadienol (Scheme 22). Protecting group 94 is then condensed with the N-terminal amino group of a side-chain protected amino acid using standard procedures to yield the hexadienoxy-Boc protected amino acid monomer 95. (Bodansky and Bodansky (1984) in *The Practice of Peptide Synthesis* (Springer Verlag, Berlin). Compound 95 can be employed in a PASS synthesis of a peptide analogous to Example 17. As illustrated in Scheme 22, the coupled product 96 is anchored by cycloaddition of the hexadieneoxy-Boc protecting group with maleimide derivatized cellulose and is released using standard acid treatment for Boc removal.

EXAMPLE 20

Peptide Nucleic Acid Preparation by PASS

The PASS synthesis of peptide nucleic acids (PNAs) proceeds analogous to the cycle described in Example 17, with the difference that the hexadienoxy-fmoc protected monomer is a PNA monomer 98 (Scheme 23).

SCHEME 23

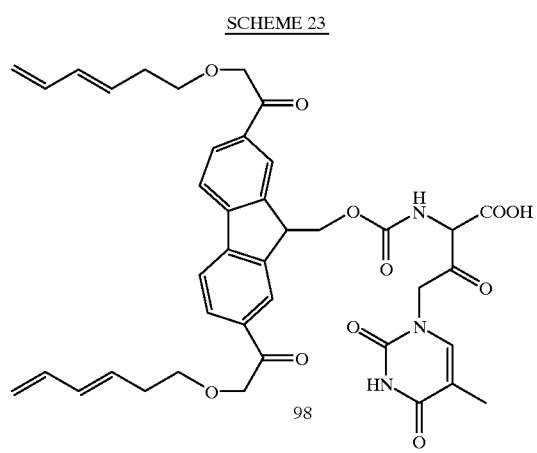

TABLE 1

Mobility ($R_f$) of Alkyl Substituted Tritanols on C18 Reverse Phase.

| Solvent | DOT | 4-decyloxy-4'-methoxytritanol | DMT |
|---|---|---|---|
| acetonitrile | 0 | 0.52 | 0.77 |
| methanol | 0 | 0.49 | 0.71 |
| 80% acetic acid | 0 | 0.02 | 0.45 |

TABLE 2

Monomer addition cycle protocol.

| Step | Procedure | Agent/Solvent | Quantity[1] (mL) | Time (min.) |
|---|---|---|---|---|
| 1. | detritylation | 2.5% DCA in $CH_2Cl_2$ trihexylsilane | 50 6.4 | 9 |
| 2. | precipitate (twice) | $CH_2Cl_2$/$Et_2O$ | | |
| 3. | coupling | Amidite DCI $CH_3CN$ | 4.5 mL (2.0 eq) 1.4 mL (6.0 eq) 50 mL | 25 |
| 4. | precipitate | $Et_2O$ | | |
| 5. | oxidation | iodobenzene diacetate | 8 50 | 8 |
| | capping | $CH_3CN$ capping soln.[2] | 6/6/6 | 5 |
| 6. | precipitate (twice) | $Et_2O$/$CH_2Cl_2$ | | |
| 7. | crystallization | EtOH | 500 | |

[1]Quantities are for 5.0 g of starting PEG-nucleoside (loading, 45 μmol/g).
[2]Capping solution: acetic anhydride, 2,6-lutidine, N-methylimidazole.

TABLE 3

Coupling Efficiency (%) for 10 mer of Oligonucleotide

| cycle | ester linker | amide linker |
|---|---|---|
| 1 | 99.6 | 99.2 |
| 2 | 162 | 123 |
| 3 | 99.4 | 98.2 |
| 4 | 99.5 | 99.3 |
| 5 | 99.1 | 99.2 |
| 6 | 99.5 | 99.0 |
| 7 | 97.1 | 97.3 |
| 8 | 98.1 | 97.8 |
| 9 | 97.3 | 97.6 |

TABLE 4

Rates of Cycloaddition of Diene-substituted Tritanols with N-Ethylmaleimide.*

| | Reaction Conditions | | | Completion of Reaction (%) | |
|---|---|---|---|---|---|
| Reaction # | N-ethyl-maleimide (eq.) | $CH_3CN/H_2O$ %/% | Time (hours) | Rxn 1 (30)→(37) | Rxn 2 (36)→(38) |
| 1 | 2 | 100/0 | 3 | 29 | 20 |
| | | | 5 | 36 | 28 |
| | | | 24 | 65 | 57 |
| 2 | 10 | 100/0 | 1 | 52 | 34 |
| | | | 3 | 71 | 51 |
| | | | 5 | 82 | 72 |
| 3 | 10 | 50/50 | 1 | 84 | 68 |
| | | | 3 | 100 | 93 |
| | | | 5 | N/A | 100 |

*Reactions were carried out at room temperature in deuterated solvents. The % completion was determined by $^1H$ NMR analysis of an aliquot taken directly from the crude reaction mixture. All reactions were carried out at a concentration of 0.07 M unless otherwise noted.

TABLE 5

Rates of Cycloaddition of Thymidine Substituted Tritanols with N-Ethylmaleimide.

| Time | % Completion |
|---|---|
| 5'-(DHDT)thymidine (31) | |
| 1 hour | 78 |
| 3 hours | 100 |
| 5'-(DHDT)thymidine 3'-phosphoramidite (32) | |
| 1 hour | 63 |
| 3 hours | 96 |
| 5 hours | 100 |

TABLE 6

Recovery of 20k-PEG-dT from an Ultrafiltration Membrane Using an Acetonitrile Solvent System.

| | First Wash (μmol PEG-dT) | Second Wash (μmol PEG-dT) | PEG-dT Recovered (%) |
|---|---|---|---|
| Control | 5.41 | | 98.7% |
| 0.25 hour | 5.30 | 0.12 | 98.9% |
| 1 hour | 5.31 | 0.07 | 98.2% |
| 4 hour | 5.28 | 0.13 | 98.7% |

TABLE 7

Recovery of 20k-PEG-dT from an Ultrafiltration Membrane Using Methylene Chloride.

| | First Wash (μmol PEG-dT) | Second Wash (μmol PEG-dT) | PEG-dT Recovered (%) |
|---|---|---|---|
| Control | 5.52 | | 101.4% |
| 0.25 hour | 5.19 | 0.13 | 97.7% |
| 1 hour | 5.32 | 0.11 | 99.7% |
| 4 hour | 5.33 | 0.08 | 99.3% |

TABLE 8

Recovery of 20k-PEG-dT from a Regenerated Ultrafiltration Membrane Using Acetonitrile.

| | First Wash (μmol PEG-dT) | Soak & Second Wash (μmol PEG-dT) | PEG-dT Recovered (%) |
|---|---|---|---|
| Control | 5.62 | | 98.7% |
| 0.25 hour | 4.80 | 0.90 | 100.0% |
| 1 hour | 4.45 | 1.20 | 99.1% |
| 4 hour | 4.40 | 1.20 | 98.3% |
| 24 hour | 4.17 | 1.40 | 97.7% |

TABLE 9

Flux Data to Membranes Exposed to Synthesis Solvents.

| Membrane | $CH_3CN$ only | $CH_3CN$ rinse of c/c/o/T exposed | $DCA/CH_2Cl_2$ | $CH_3CN$ rinse of $DCA/CH_2Cl_2$ |
|---|---|---|---|---|
| PVDF | 0.75 | 0.83 | 0.94 | 0.8 |
| polypropylene | 7.19 | 7.45 | 8.76 | 8.51 |

We claim:

1. A method for the solution phase synthesis of peptides comprising:

a) reacting an N-terminal protected amino acid monomer unit having the following formula:

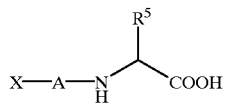

wherein $R^5$ is selected from H or a protected known amino acid side chain;

A is an amino protecting group(s); and

X is selected from the group consisting of a diene, dienophile, alkyne and disulfide, with a peptide starting material to form a reaction mixture containing a peptide product; and b) partitioning the peptide product from the unreacted peptide starting material, unreacted N-terminal protected amino acid monomer unit, side-products and reagents based on the presence of the N-terminal protecting group.

2. The method of claim 1 further comprising:

c) repeating steps a) and b) in successive cycles a select number of times to yield the desired product.

3. The method of claim 1 wherein A is selected from the group consisting of a urethane, benzyl, acyl and triphenylmethyl.

4. The method of claim 3 wherein said urethane is 9-fluorenylmethyl carbonyl (Fmoc) or tert-butoxycarbonyl (Boc).

5. A method for the solution phase synthesis of peptides comprising:

a) reacting an N-terminal protected amino acid monomer unit with a peptide starting material to form a reaction mixture containing a peptide product; and b) partitioning the pentide product from the unreacted peptide starting material, unreacted N-terminal protected amino acid monomer unit, side-products and reagents based on the presence of the N-terminal protecting group, wherein the partitioning is performed by eluting the reaction mixture through a solid support, wherein said solid support covalently reacts with said N-terminal protecting group.

6. The method of claim 5 wherein said covalent reaction is a Diels-Alder reaction.

7. The method of claim 5 wherein said solid support is selected from the group consisting of a resin, membrane and polymer.

8. The method of claim 5 wherein said solid support is selected from the group consisting of a hydrophobic reversed phase resin, a thiopropyl sepharose resin, a mercurated resin, an agarose adipic acid hydrazide resin, an avidin resin, an ultrafiltration membrane, Tentagel™, polyethylene glycol and an inorganic oxide, selected from the group consisting of silica gel, alumina, controlled pore glass and zeolite.

9. The method of claim 8 wherein the hydrophobic reversed phase resin is selected from the group consisting of a C2 to a C18 polystyrene resin.

10. A method for the solution phase synthesis of peptides comprising:

a) reacting an N-terminal protected amino acid monomer unit with a peptide starting material to form a reaction mixture containing a peptide product; and b) partitioning the peptide product from the unreacted peptide starting material, unreacted N-terminal protected amino acid monomer unit, side-products and reagents based on the presence of the N-terminal protecting group, wherein the partitioning is performed by eluting the reaction mixture through a solid support, wherein said solid support is derivatized with a group selected from a diene, dienophile, mercaptane and borate.

11. The method of claim 10 wherein said diene is selected from the group consisting of 3,5-hexadiene.

12. The method of claim 10 wherein said dienophile is maleimide.

13. The product formed by the method of claim 1.

14. The method of claim 1 wherein said diene is 3,5-hexadienoxy or sorbic amide.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 15  nucleotides
      (B) TYPE: nucleic acid
      (C) STRANDEDNESS: single
      (D) TOPOLOGY: linear (ix) FEATURE:
      (D) OTHER INFORMATION: The bond between G at position 13 and

```
                T at position 14 is a [3',3'] linkage.

(xi) SEQUENCE DESCRIPTION: SEQ ID NO:1:

CTAAACGTAA TGGTT                                                15

(2) INFORMATION FOR SEQ ID NO:2:

(i) SEQUENCE CHARACTERISTICS:
        (A) LENGTH: 10  nucleotides
        (B) TYPE: nucleic acid
        (C) STRANDEDNESS: single
        (D) TOPOLOGY: linear (ix) FEATURE:
        (D) OTHER INFORMATION: The bond between G at position 8 and
            T at position 9 is a [3',3'] linkage.

(xi) SEQUENCE DESCRIPTION: SEQ ID NO:2:

CGTAATGGTT                                                      10
```